US012665091B2

(12) United States Patent
Zhang et al.

(10) Patent No.: US 12,665,091 B2
(45) Date of Patent: Jun. 23, 2026

(54) DEEP LEARNING APPROACH IDENTIFIED PATHOLOGICAL ABNORMALITIES PREDICTIVE OF GRAFT LOSS IN KIDNEY TRANSPLANT

(71) Applicant: Icahn School of Medicine at Mount Sinai, New York, NY (US)

(72) Inventors: Weijia Zhang, New York, NY (US); Barbara Murphy, New York, NY (US); Fadi El Salem, New York, NY (US); Zhengzi Yi, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 428 days.

(21) Appl. No.: 18/557,118

(22) PCT Filed: Apr. 26, 2022

(86) PCT No.: PCT/US2022/026387
§ 371 (c)(1),
(2) Date: Oct. 25, 2023

(87) PCT Pub. No.: WO2022/232172
PCT Pub. Date: Nov. 3, 2022

(65) Prior Publication Data
US 2024/0387050 A1 Nov. 21, 2024

Related U.S. Application Data

(60) Provisional application No. 63/179,999, filed on Apr. 26, 2021.

(51) Int. Cl.
G06T 7/00 (2017.01)
G16H 30/40 (2018.01)
(Continued)

(52) U.S. Cl.
CPC .......... *G16H 50/30* (2018.01); *G06T 7/0012* (2013.01); *G16H 30/40* (2018.01); *G16H 50/70* (2018.01); *G06T 2207/30084* (2013.01)

(58) Field of Classification Search
None
See application file for complete search history.

(56) References Cited

U.S. PATENT DOCUMENTS

2019/0295252 A1 9/2019 Fuchs et al.
2020/0310098 A1 10/2020 Ince et al.
(Continued)

FOREIGN PATENT DOCUMENTS

WO WO 2020/178526 A1 9/2020
WO WO-2023043944 A1 * 3/2023 ............. G16H 10/40

OTHER PUBLICATIONS

Agresti, An Introduction to Categorical Data Analysis, 1996, Chapter 5, pp. 103-144, John Wiley & Son.
(Continued)

*Primary Examiner* — Thomas D Lee

(57) ABSTRACT

Systems and methods for identifying risk of kidney graft failure in a subject are provided. An image of a graft biopsy is obtained, the image representing at least a subset of a plurality of morphological classes including a tissue compartment and inflammation class. The image is inputted into a trained model that identifies, as output, for each morphological class in at least the subset, corresponding objects in the image that fall within the morphological class. For each morphological class, corresponding digital features are generated comprising a first subset of individual feature scores obtained using the objects for the morphological class and a second subset of composite feature scores obtained by combining individual feature scores. Digital features for (Continued)

each morphological class are compared to a reference criterion, thus determining risk of kidney graft failure.

22 Claims, 33 Drawing Sheets

(51) Int. Cl.
    *G16H 50/30*         (2018.01)
    *G16H 50/70*         (2018.01)

(56)           References Cited

U.S. PATENT DOCUMENTS

| | | | |
|---|---|---|---|
| 2021/0158524 A1 | 5/2021 | Madabhushi et al. | |
| 2022/0068480 A1* | 3/2022 | Manzi | G06T 7/0012 |
| 2022/0378379 A1* | 12/2022 | Zimmerman | A61B 5/7275 |
| 2023/0054069 A1* | 2/2023 | Tangri | G06N 5/01 |
| 2024/0071621 A1* | 2/2024 | Kim | G16H 50/30 |

OTHER PUBLICATIONS

Boser et al., 1992, "A training algorithm for optimal margin classifiers," in Proceedings of the 5th Annual ACM Workshop on Computational Learning Theory, ACM Press, Pittsburgh, Pa., pp. 142-152.
Breiman, 1999, "Random Forests—Random Features," Technical Report 567, Statistics Department, U.C. Berkeley, Sep. 1999.
Clayton et al., "Relationship between eGFR decline and hard outcomes after kidney transplants," J Am Soc Nephrol. 2016; 27:3440-3446.
Duda and Hart, Pattern Classification and Scene Analysis, 1973, John Wiley & Son.
Faddoul et al., "Analysis of biomarkers within the initial 2 years posttransplant and 5-year kidney transplant outcomes: results from clinical trials in Organ Transplantation-17," Transplantation. 2018; 102:673-680.
Fernandes et al., 2017, "Transfer Learning with Partial Observability Applied to Cervical Cancer Screening," Pattern Recognition and Image Analysis: 8th Iberian Conference Proceedings, 243-250.
Furness and Taub, "Convergence of European Renal Transplant Pathology Assessment Procedures (CERTAP) Project. International variation in the interpretation of renal transplant biopsies: report of the CERTPAP project," Kidney Int. 2001; 60:1998-2012.
Hastie et al., 2001, The Elements of Statistical Learning, Springer-Verlag, New York, Chapter 9.
Hunsicker, "A survival advantage for renal transplantation," N Engl J Med. 1999; 341:1762-1763.
Krizhevsky et al., 2012, "Imagenet classification with deep convolutional neural networks," in Advances in Neural Information Processing Systems 2, Pereira, Burges, Bottou, Weinberger, eds., pp. 1097-1105.
Larochelle et al., 2009, "Exploring strategies for training deep neural networks," J Mach Learn Res 10, pp. 1-40.
McLachlan et al., Bioinformatics 18(3):413-422, 2002.
Ng et al., 2002, "On discriminative vs. generative classifiers: A comparison of logistic regression and naive Bayes," Advances in Neural Information Processing Systems, 14.
Parajuli et al., "Histopathological characteristics and causes of kidney graft failure in the current era of immunosuppression," World J Transplant. 2019; 9:123-133.
Rumelhart et al., "Learning Representations by Back-propagating Errors" Nature, v. 323, p. 533, Oct. 9, 1986.
Schliep et al., 2003, Bioinformatics 19(1):1255-1263.
Uchida, 2013, "Image processing and recognition for biological images," Develop. Growth Differ. 55, 523-549.
Vincent et al., 2010, "Stacked denoising autoencoders: Learning useful representations in a deep network with a local denoising criterion," J Mach Learn Res, vol. 11, pp. 3371-3408.
Yi et al., "Deep learning identified pathological abnormalities predictive of graft loss in kidney transplant biopsies," Kidney International (2022) 101, 288-298.
Zeiler, 2012 "ADADELTA: An Adaptive Learning Rate Method," ARXIV:1212.5701.

* cited by examiner

(A)

214

Input the first image into a trained model, where the trained model comprises at least 10,000 parameters.

216

The trained model comprises a convolutional neural network comprising one or more filters, a respective kernel size, and a respective stride.

218

The trained model comprises a plurality of component models, comprising:
        a compartment detection model trained to identify one or more first corresponding objects in the first image that fall within a first morphological class in the plurality of morphological classes,
        an inflammation detection model trained to identify one or more second corresponding objects in the first image that fall within a second morphological class in the plurality of morphological classes, and
        a tissue segmentation model trained to identity one or more third corresponding objects in the first image that fall within a third morphological class in the plurality of morphological classes.

220

Each respective component model in the plurality of component models is selected from the group consisting of a pixel-level prediction algorithm and an instance-level object detection algorithm.

222

Identify, as output from the trained model, for each respective morphological class in the at least the subset of morphological classes, a corresponding one or more objects in the first image that fall within the respective morphological class, where the subset of morphological classes includes the first tissue compartment class or the inflammatory mediator class.

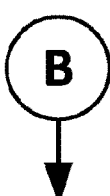

Generate, for each respective morphological class in the at least the subset of morphological classes, a corresponding plurality of digital features comprising:

(i) a first corresponding subset of individual feature scores, where each respective individual feature score is obtained using the corresponding one or more objects for the respective morphological class, and (ii) a second corresponding subset of composite feature scores, where each respective composite feature score is obtained by combining two or more individual feature scores in the first corresponding subset of individual feature scores.

A respective individual feature score in the first corresponding subset of individual feature scores is selected from the group consisting of: a size of an area of the substrate, a number of objects in a corresponding plurality of objects for a respective morphological class within an area of the substrate, and a percentage of a corresponding plurality of objects for a respective morphological class over an area of the substrate.

The generating the corresponding plurality of digital features for a respective morphological class further comprises:

(i) identifying, in the first image, a first region of interest as having a first condition for the respective morphological class, and (ii) assigning the first condition to one or more individual feature scores, in the first corresponding subset of individual feature scores, where the first condition is selected from the group consisting of abnormal and normal.

The identifying the first region of interest as having the first condition comprises:

determining a corresponding set of object density statistics for the first region of interest, where each respective object density statistic in the corresponding set of object density statistics is obtained using the corresponding one or more objects for the respective morphological class, and, when each respective object density statistic in the set of object density statistics satisfies a corresponding threshold criterion, classifying the first region of interest as having the first condition.

Figure 2D:
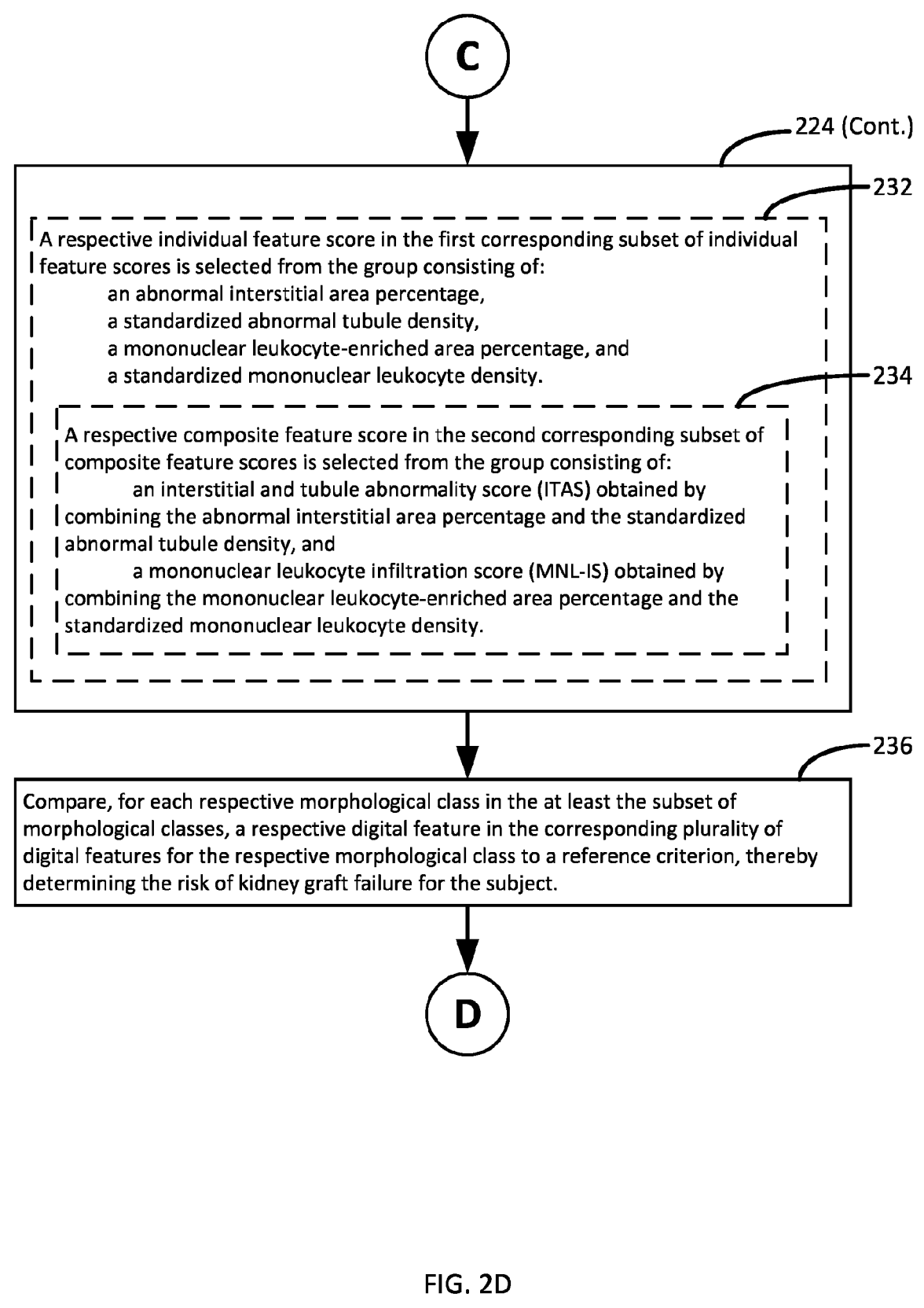

A respective individual feature score in the first corresponding subset of individual feature scores is selected from the group consisting of:
    an abnormal interstitial area percentage,
    a standardized abnormal tubule density,
    a mononuclear leukocyte-enriched area percentage, and
    a standardized mononuclear leukocyte density.

234

A respective composite feature score in the second corresponding subset of composite feature scores is selected from the group consisting of:
    an interstitial and tubule abnormality score (ITAS) obtained by combining the abnormal interstitial area percentage and the standardized abnormal tubule density, and
    a mononuclear leukocyte infiltration score (MNL-IS) obtained by combining the mononuclear leukocyte-enriched area percentage and the standardized mononuclear leukocyte density.

236

Compare, for each respective morphological class in the at least the subset of morphological classes, a respective digital feature in the corresponding plurality of digital features for the respective morphological class to a reference criterion, thereby determining the risk of kidney graft failure for the subject.

D 236 (Cont.)

238

Generate a composite class score by combining at least a first composite feature
score for a corresponding first morphological class and a second composite feature
score for a corresponding second morphological class different from the first
morphological class.
        The comparing, for each respective morphological class in the at least the
subset of morphological classes, a respective digital feature in the corresponding
plurality of digital features for the respective morphological class to a reference
criterion, further comprises comparing the composite class score to the reference
criterion.

240

The kidney graft failure is death-censored graft loss, acute cellular rejection, or
decline of estimated glomerular filtration rate (eGFR).

242

Use the respective digital feature to categorize the first image into a risk category,
based on the comparison with the reference criterion, where the risk category is
one of three nonoverlapping stratified risk categories selected from the group
consisting of low risk, medium risk, or high risk.

244

Determine a correlation between the respective digital feature and a reference
measure of kidney damage.

246

The first image is of a pre-implantation kidney graft biopsy, and the risk of kidney
graft failure is predictive for a period of no more than 1 year post-transplantation.

248

The first image is of a post-transplantation kidney graft biopsy, and the risk of kidney
graft failure is predictive for a period of 1 year or more post-transplantation.

250

The trained model is obtained by a procedure comprising:
  (a) obtaining, in electronic format, a training dataset comprising: for each respective training sample in a plurality of training samples:
    (i) a corresponding training image of a training kidney graft biopsy on a substrate, where the corresponding training image represents at least a second subset of morphological classes in a plurality of morphological classes comprising at least the first tissue compartment class and the inflammatory mediator class, and where the corresponding training image comprises at least 10,000 pixels;
    (ii) a corresponding measured indication that localizes one or more objects in the corresponding training image that fall within each respective morphological class in the at least the second subset of morphological classes, where:
        for each respective training sample in a first subset of the plurality of training samples, the corresponding training image is of a kidney graft biopsy obtained pre-implantation,
        for each respective training sample in a second subset of the plurality of training samples, the corresponding training image is of a kidney graft biopsy obtained post-transplantation, and
        the plurality of training samples collectively represents each respective morphological class in the plurality of morphological classes;
  (b) training an untrained or partially trained model comprising at least 10,000 parameters by a procedure comprising, for each corresponding training image of each corresponding training sample in the plurality of training samples:
    (i) inputting the respective image as input to the untrained or partially trained model thereby obtaining a corresponding calculated indication that localizes one or more objects in the corresponding image that fall within each respective morphological class in the at least the second subset of morphological classes, and
    (ii) using at least a difference between the corresponding calculated indication and the corresponding measured indication to update all or a subset of the at least 10,000 parameters, thereby forming the trained model, where the trained model is configured to identify, for each respective morphological class in the plurality of morphological classes, a corresponding one or more objects that fall within the respective morphological class.

252

Each respective training sample in the plurality of training samples comprises, for each respective morphological class in the plurality of morphological classes, a corresponding measured indication that localizes one or more objects in the corresponding image that fall within the respective morphological class.

FIG. 2F

Input image

Banff ci = 1
Banff ct = 1
Banff ti = 2 i Original WSI

Output image ii Full compartment prediction

Abnormal interstitial area percentage = 0.158
Abnormal tubules density = 6.706
MNL-enriched area percentage = 0.286
MNL density = 5.562

Background
MNL
Glomerulus
Normal tubule
Abnormal tubule

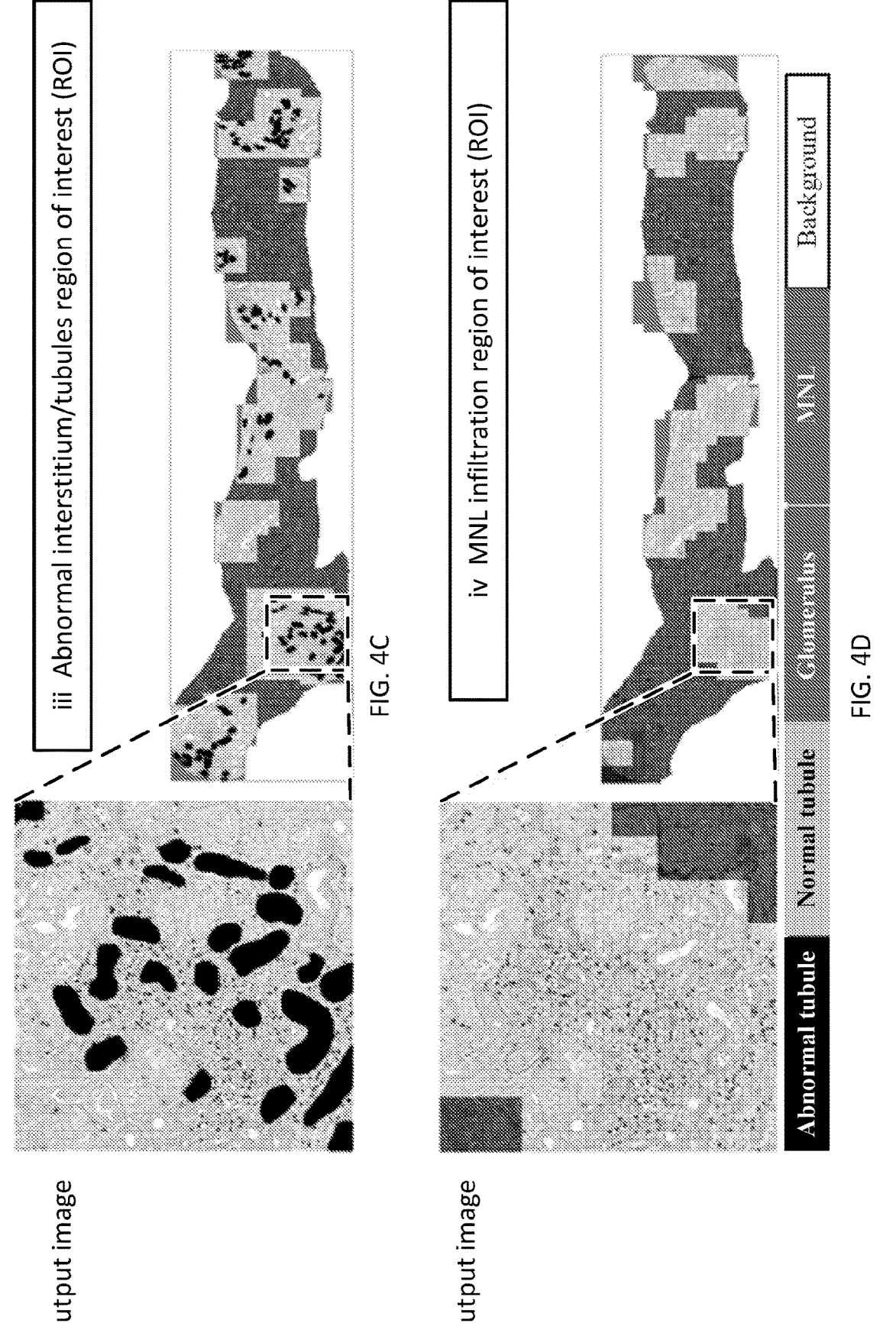

| | Baseline | 1 yr | 2 yr | 3 yr | 4 yr | 5 yr | 6 yr | 7 yr |
|---|---|---|---|---|---|---|---|---|
| High | 25 | 21 | 19 | 18 | 16 | 13 | 4 | 0 |
| Medium | 86 | 78 | 75 | 71 | 62 | 48 | 22 | 3 |
| Low | 206 | 194 | 186 | 179 | 161 | 133 | 72 | 9 |

DEEP LEARNING APPROACH IDENTIFIED PATHOLOGICAL ABNORMALITIES PREDICTIVE OF GRAFT LOSS IN KIDNEY TRANSPLANT

CROSS REFERENCE TO RELATED APPLICATIONS

This patent application claims priority to U.S. Provisional Patent Application No. 63/179,999 entitled "A Deep Learning Approach Identified Pathological Abnormalities Predictive of Graft Loss in Kidney Transplant," filed Apr. 26, 2021, which is hereby incorporated by reference in its entirety.

TECHNICAL FIELD

This specification describes using deep learning techniques to determine kidney graft failure.

BACKGROUND

Kidney transplantation is the treatment of choice for patients with end-stage renal disease (ESRD). Interstitial fibrosis and tubular atrophy and inflammation are considered major contributors to post-transplant kidney allograft failure irrespective of etiology of injury. See Hunsicker, "A survival advantage for renal transplantation," N Engl J Med. 1999; 341:1762-1763; and Parajuli et al., "Histopathological characteristics and causes of kidney graft failure in the current era of immunosuppression," World J Transplant. 2019; 9:123-133.

Currently interstitial fibrosis and tubular atrophy and inflammation are graded by pathologic assessment of biopsies. While cumulative injury represented as categorical Banff scores have been associated with post-transplant graft function and survival, these have intermediate sensitivity for graft failure prediction in any given biopsy, due to inter-observer and intra-observer variability. Thus, prediction of long-term graft survival remains a major challenge. See Furness and Taub, "Convergence of European Renal Transplant Pathology Assessment Procedures (CERTAP) Project. International variation in the interpretation of renal transplant biopsies: report of the CERTPAP project," Kidney Int. 2001; 60:1998-2012.

Post-transplant factors, such as the rate of decline of estimated glomerular filtration rate (eGFR) up to 2 years have shown predictive ability. However, factors obtained early post-transplantation that predict longer-term post-transplant course would offer distinct advantages for identifying patients at risk for graft loss and therefore, potentially guide subsequent patient management. See Clayton et al., "Relationship between eGFR decline and hard outcomes after kidney transplants," J Am Soc Nephrol. 2016; 27:3440-3446; and Faddoul et al., "CTOT-17 Consortium. Analysis of biomarkers within the initial 2 years posttransplant and 5-year kidney transplant outcomes: results from clinical trials in Organ Transplantation-17," Transplantation. 2018; 102:673-680.

Given the above background, there is a need in the art for systems and methods of determining and analyzing features for identifying risk of kidney graft failure.

SUMMARY

Advantageously, the present disclosure provides robust techniques for identifying a risk of kidney graft failure for a subject. The following presents a summary of the invention in order to provide a basic understanding of some of the aspects of the invention. This summary is not an extensive overview of the invention. It is not intended to identify key/critical elements of the invention or to delineate the scope of the invention. Its sole purpose is to present some of the concepts of the invention in a simplified form as a prelude to the more detailed description that is presented later.

Accordingly, one aspect of the present disclosure provides a method for identifying a risk of kidney graft failure for a subject. In some embodiments, the method is performed at a computer system comprising at least one processor and a memory storing at least one program for execution by the at least one processor, the at least one program comprising instructions for performing the method.

The method includes obtaining, in electronic format, a first image of a kidney graft biopsy on a substrate, where the first image represents at least a first subset of morphological classes in a plurality of morphological classes comprising at least a first tissue compartment class and an inflammatory mediator class, the first image comprises a plurality (e.g., at least 10,000) of pixels, and the graft biopsy originates from the subject. The first image is inputted into a trained model (e.g., comprising at least 10,000 parameters). The method further comprises identifying, as output from the trained model, for each respective morphological class in the at least the first subset of morphological classes, a corresponding one or more objects in the first image that fall within the respective morphological class, where the first subset of morphological classes includes the first tissue compartment class or the inflammatory mediator class.

For each respective morphological class in the at least the first subset of morphological classes, a corresponding plurality of digital features is generated comprising (i) a first corresponding subset of individual feature scores, where each respective individual feature score is obtained using the corresponding one or more objects for the respective morphological class, and (ii) a second corresponding subset of composite feature scores, where each respective composite feature score is obtained by combining two or more individual feature scores in the first corresponding subset of individual feature scores.

For each respective morphological class in the at least the first subset of morphological classes, a respective digital feature in the corresponding plurality of digital features for the respective morphological class is compared to a reference criterion, thereby determining the risk of kidney graft failure for the subject.

In some embodiments, the first image is a whole-slide histological image. In some embodiments, the first image comprises at least 100,000 pixels.

In some embodiments, the kidney graft biopsy is obtained pre-implantation or post-transplantation. In some embodiments, the kidney graft biopsy is preserved by paraffin embedding.

In some embodiments, the first tissue compartment class is selected from the group consisting of tubules, glomeruli, and interstitium, and the inflammatory mediator class is mononuclear leukocytes (MNLs).

In some embodiments, the trained model comprises a plurality of component models, comprising a compartment detection model trained to identify one or more first corresponding objects in the first image that fall within a first morphological class in the plurality of morphological classes, an inflammation detection model trained to identify one or more second corresponding objects in the first image that fall within a second morphological class in the plurality of morphological classes, and a tissue segmentation model trained to identity one or more third corresponding objects in the first image that fall within a third morphological class in the plurality of morphological classes.

In some such embodiments, each respective component model in the plurality of component models is selected from the group consisting of a pixel-level prediction algorithm and an instance-level object detection algorithm.

In some embodiments, the trained model comprises a convolutional neural network comprising one or more filters, a respective kernel size, and a respective stride.

In some embodiments, the generating the corresponding plurality of digital features for a respective morphological class further comprises (i) identifying, in the first image, a first region of interest as having a first condition for the respective morphological class, and (ii) assigning the first condition to one or more individual feature scores, in the first corresponding subset of individual feature scores, where the first condition is selected from the group consisting of abnormal and normal.

In some such embodiments, the identifying the first region of interest as having the first condition comprises determining a corresponding set of object population statistics for the first region of interest, where each respective object population statistic in the corresponding set of object population statistics is obtained using the corresponding one or more objects for the respective morphological class, and, when each respective object population statistic in the set of object population statistics satisfies a corresponding threshold criterion, classifying the first region of interest as having the first condition.

In some embodiments, a respective individual feature score in the first corresponding subset of individual feature scores is selected from the group consisting of: a size of an area of the substrate, a number of objects in a corresponding plurality of objects for a respective morphological class within an area of the substrate, and a percentage of a corresponding plurality of objects for a respective morphological class over an area of the substrate.

In some embodiments, a respective individual feature score in the first corresponding subset of individual feature scores is selected from the group consisting of: an abnormal interstitial area percentage, a standardized abnormal tubule density, a mononuclear leukocyte-enriched area percentage, and a standardized mononuclear leukocyte density.

In some embodiments, a respective composite feature score in the second corresponding subset of composite feature scores is selected from the group consisting of an interstitial and tubule abnormality score (ITAS) obtained by combining the abnormal interstitial area percentage and the standardized abnormal tubule density, and a mononuclear leukocyte infiltration score (MNL-IS) obtained by combining the mononuclear leukocyte-enriched area percentage and the standardized mononuclear leukocyte density.

In some embodiments, the method further comprises generating a composite class score by combining at least a first composite feature score for a corresponding first morphological class and a second composite feature score for a corresponding second morphological class different from the first morphological class, where the comparing, for each respective morphological class in the at least the first subset of morphological classes, a respective digital feature in the corresponding plurality of digital features for the respective morphological class to a reference criterion further comprises comparing the composite class score to the reference criterion.

In some embodiments, the kidney graft failure is death-censored graft loss, acute cellular rejection, or decline of estimated glomerular filtration rate (eGFR).

In some embodiments, the method further includes using the respective digital feature to categorize the first image into a risk category, based on the comparison with the reference criterion, where the risk category is one of three nonoverlapping stratified risk categories selected from the group consisting of low risk, medium risk, or high risk.

In some embodiments, the method further includes determining a correlation between the respective digital feature and a reference measure of kidney damage.

In some embodiments, the first image is of a pre-implantation kidney graft biopsy, and the risk of kidney graft failure is predictive for a period of no more than 1 year post-transplantation.

In some embodiments, the first image is of a post-transplantation kidney graft biopsy, and the risk of kidney graft failure is predictive for a period of 1 year or more post-transplantation.

In some embodiments, the trained model is obtained by a procedure comprising: (a) obtaining, in electronic format, a training dataset comprising, for each respective training sample in a plurality of training samples: (i) a corresponding training image of a training kidney graft biopsy on a substrate, where the corresponding training image represents at least a second subset of morphological classes in a plurality of morphological classes comprising at least the first tissue compartment class and the inflammatory mediator class, and where the corresponding training image comprises a plurality (e.g., at least 10,000) of pixels, and (ii) a corresponding measured indication that localizes one or more objects in the corresponding training image that fall within each respective morphological class in the at least the second subset of morphological classes. In some such embodiments, for each respective training sample in a first subset of the plurality of training samples, the corresponding training image is of a kidney graft biopsy obtained pre-implantation, for each respective training sample in a second subset of the plurality of training samples, the corresponding training image is of a kidney graft biopsy obtained post-transplantation, and the plurality of training samples collectively represents each respective morphological class in the plurality of morphological classes.

In some embodiments, the obtaining the trained model further comprises (b) training an untrained or partially trained model comprising a plurality (e.g., at least 10,000) of parameters by a procedure comprising, for each corresponding training image of each corresponding training sample in the plurality of training samples: (i) inputting the respective image as input to the untrained or partially trained model thereby obtaining a corresponding calculated indication that localizes one or more objects in the corresponding image that fall within each respective morphological class in the at least the second subset of morphological classes, and (ii) using at least a difference between the corresponding calculated indication and the corresponding measured indication to update all or a subset of the plurality (e.g., at least 10,000) of parameters, thereby forming the trained model, where the trained model is configured to identify, for each respective morphological class in the plurality of morphological classes, a corresponding one or more objects that fall within the respective morphological class.

In some embodiments, the training (b) is characterized by one or more hyperparameters in the plurality (e.g., at least 10,000) of parameters.

In some embodiments, a respective hyperparameter in the one or more hyperparameters comprises a predetermined number of training epochs.

In some embodiments, a respective hyperparameter in the one or more hyperparameters comprises a predetermined batch size, where the size specifies a number of corresponding training images of a predetermined number of training samples in the plurality of training samples.

In some embodiments, a respective hyperparameter in the one or more hyperparameters comprises a predetermined learning rate.

In some embodiments, the plurality of training samples comprises at least 1,000 training samples.

In some embodiments, each respective training sample in the plurality of training samples comprises, for each respective morphological class in the plurality of morphological classes, a corresponding measured indication that localizes one or more objects in the corresponding image that fall within the respective morphological class.

Another aspect of the present disclosure provides a computing system including one or more processors and memory storing one or more programs that further comprise instructions for performing any of the above-disclosed methods alone or in combination.

Another aspect of the present disclosure provides non-transitory computer-readable storage medium comprising one or more programs in which the one or more programs further comprise instructions for performing any of the above-disclosed methods alone or in combination. The one or more programs are configured for execution by a computer.

Various embodiments of systems, methods, and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand these and other features and attributes of various embodiments of the present disclosure and their advantageous applications and/or uses.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIGS. 2A, 2B, 2C, 2D, 2E, and 2F collectively illustrate an example flowchart of a method for identifying a risk of kidney graft failure for a subject, in which dashed boxes represent optional steps, in accordance with some embodiments of the present disclosure.

FIG. 3A illustrates Stage I for tissue compartment recognition. Ninety-three slides that represented the spectrum of histologic lesions were selected from the Genomics of Chronic Allograft Rejection (GoCAR) periodic acid-Schiff (PAS) slides and then randomly divided into a discovery set (n=60) and a testing set (n=33). The annotated sections of these slides were used for deep-learning model construction and evaluation. During the training process, component models were constructed based on 2 types of deep-learning structures for tissue compartment or mononuclear leukocyte (MNL) detection (by Mask Region-based Convolution Neural Network (MR-CNN)) and tissue segmentation (by U-Net). Component models were determined through evaluation with 10-fold cross-validation and finally applied to the testing set. FIG. 3B illustrates Stage II for the whole-slide image (WSI) clinical investigation. Using the established deep-learning model, 789 baseline and 12-month post-transplantation (post-tx) WSIs from 2 independent cohorts (GoCAR and Australian Chronic Allograft Dysfunction (AUSCAD)) were processed and a series of slide-wide digital features capturing the abnormalities in the interstitium and tubules, and MNL infiltration were extracted. These features were further examined through association with Banff scores and post-transplantation graft survival. bx, biopsies; FC, fully connected; RPN, region proposal network.

FIGS. 4A, 4B, 4C, 4D, 4E, 4F, and 4G collectively demonstrate slide-wide digital features and correlation with corresponding Banff scores, in accordance with an embodiment of the present disclosure. FIGS. 4A-4D collectively illustrate slide-wide digital features from a whole-slide image (WSI) investigation using an example WSI. FIG. 4A: (i) original WSI; FIG. 4B: (ii) whole-slide prediction; FIG. 4C: (iii) predicted abnormal interstitium or tubules regions of interest (ROIs); FIG. 4D: (iv) predicted mononuclear leukocytes (MNLs) infiltrated ROIs. For each of FIGS. 4A-4D, the left panel shows zoom-in inspections of 1 particular abnormal region within the inset box on the WSI. Various morphological classes, tissue compartments, and/or abnormal/normal conditions are indicated by the accompanying legend (Abnormal tubule: black; Normal tubule: light gray; Glomerulus: medium gray; MNLs: medium gray; Background: white). FIGS. 4E-G collectively illustrate correlation of digital features with Banff scores. Correlation of abnormal interstitial area percentage and Banff ci score (FIG. 4E), abnormal tubules density and Banff ct score (FIG. 4F), and MNL-enriched area percentage and Banff ti score (FIG. 4G) in the Genomics of Chronic Allograft Rejection (GoCAR) 12-month post-transplantation biopsy slides (n=200) are shown. P-values were calculated from Spearman's correlation test.

FIG. 5A illustrates a heatmap of time-dependent area under the curve (AUC) values in predicting death-censored graft loss (DCGL) by Banff scores and digital features at different time intervals in baseline biopsy slides (n=317). Numbers and shading range of boxes represent AUC values at given time points. FIG. 5B illustrates Kaplan-Meier curves of DCGL in high (502), intermediate (504), and low (506) risk groups stratified by the Interstitial and Tubular Abnormality Score (ITAS) from baseline biopsies (n=317). Baseline ITAS groups are defined as high, ITAS>0.6; intermediate, 0.1≤ITAS≤0.6; and low, ITAS<0.1. P-values are calculated by log-rank test. FIG. 5C illustrates average estimated glotnetular filtration rate (eGFR) values over time within 12-months post-transplantation per baseline ITAS risk group (502, 504, 506). Error bars represent x0.1 SD from mean values. FIG. 5D shows bar charts demonstrating proportions of delayed graft function (DGF) and no DGF (upper panel) and 3-month post-transplant Chronic Allograft Damage Index (CADI)>2 or ≤2 (lower panel) among 3 baseline ITAS risk groups. P-values are calculated by Fisher's exact test.

FIG. 6A shows a heatmap of time-dependent area under the curve (AUC) values in predicting death-censored graft loss (DCGL) by Banff scores and digital features at different time intervals in 12-month post-transplant biopsy slides (n=200). Numbers and shading range of boxes represent AUC values at given time points. FIG. 6B shows a heatmap of time-dependent AUCs in predicting DCGL by the 12-month Composite Damage Score (CDS, capturing the interstitial and tubular abnormality (ITAS) and mononuclear leukocyte infiltration (MNL-IS)) high or low group and other pathologic and/or clinical factors that were obtained prior to or at 12 months. The 12-month CDS groups are defined as high, CDS>1.5, and low, CDS≤1.5. FIG. 6C shows Kaplan-Meier curves of the DCGL in high (602) and low (604) risk groups stratified by the 12-month CDS. P-value is calculated by log-rank test. FIG. 6D illustrates bar charts demonstrating proportions of 6-month to 24-month estimated glomerular filtration rate (eGFR) decline ≥30% or <30% (upper panel) and the 24-month post-transplant Chronic Allograft Damage Index (CADI)>2 or ≤2 (lower panel) between 12-month CDS risk groups. P-values are calculated by Fisher's exact test.

FIG. 7A shows the feature extraction process. A 384×384 pixel unit "window" (e.g., filter) was used to scan across a whole-slide image (WSI) with a stride of 128 pixels. "Windows" scanned by the filter that had wide interstitial space or high amounts of MN leukocytes were defined as interstitial regions of interest (intROI, intR) or inflammatory regions of interest (infROI, infR). A series of individual feature scores were defined at the ROI or slide level and further integrated into composite feature scores aiming for overall abnormality estimation. FIG. 7B illustrates the definition (e.g., calculation) of individual feature scores in interstitium, tubules and MNL infiltration.

FIG. 8A shows correlation of Abnormal Interstitial Area Percentage and Banff ci score (upper panel), and Abnormal Tubules Density and Banff ct score (bottom panel) in GoCAR baseline biopsy slides (n=317). FIGS. 8B-8C show correlation of Abnormal Interstitial Area Percentage and Banff ci score (FIG. 8B, top panel), and Abnormal Tubules Density and Banff ct score (FIG. 8B, bottom panel), and MNL-enriched Area Percentage and Banff i+t score (FIG. 8C) in AUSCAD 12-month post-transplant biopsy slides (n=111). P-values were calculated from Spearman's correlation test.

FIG. 9A shows an example of a WSI that was determined to be normal using Banff scores but was determined to be abnormal using a plurality of digital features. FIG. 9A, upper-panel shows a whole-slide image highlighting abnormal interstitium/tubules regions obtained using a trained model and associated digital features, as disclosed herein. FIG. 9A, lower-panel shows close-up views of (i) original, (ii) full compartment prediction, and (iii) abnormal ROI masks from one abnormal region in the whole-slide image (upper panel, inset box). FIGS. 9B-9C illustrate comparison of subsequent pathological outcomes ci+ct within 3 months (up to and including 3 months) (FIG. 9B, left panel) and ci+ct from 3 to 12 months (up to and including 12 months) (FIG. 9B, right panel) and clinical outcomes 3-month eGFR (FIG. 9C, left panel), 6-month eGFR (FIG. 9C, middle panel), and 12-month eGFR (FIG. 9C, right panel) between digitally-abnormal vs. digitally-normal patients who were all determined normal by Banff scores from GoCAR baseline biopsies. P-values are calculated by t-test.

FIG. 10A shows a dot heatmap of association of Banff scores and digital features with post-transplant death-censored graft loss (DCGL) in baseline biopsy slides (n=317). The size of dots and number of asterisks indicate significance level (p-value) of association by Cox proportional hazards regression (NS: p≥0.1; .: 0.05≤p<0.1; *:0.005≤p<0.05; : 5e-04≤p<0.005; *: 5e-05≤p<5e-04; **:p<5e-OS). Shading darkness of dots indicate hazard ratio. FIG. 10B shows Kaplan-Meier curves of DCGL in ITAS high (1002) vs. intermediate (1004) vs. low (1006) group in deceased donor population in baseline biopsies (n=174). Baseline ITAS groups are defined as: high: ITAS>0.6, intermediate: 0.1≤ITAS≤0.6, low: ITAS<0.1. P-values are calculated by log-rank test. FIG. 10C shows Kaplan-Meier curves of DCGL in ci+ct high (1002) vs. intermediate (1004) vs. low (1006) group in baseline biopsies. ci+ct groups are defined as: high: ci+ct>1, intermediate: ci+ct=1, low: ci+ct=0. P-values are calculated by log-rank test. FIG. 10D shows Kaplan-Meier curves of DCGL in KDPI high (1002) vs. intermediate (1004) vs. low (1006**) group in deceased donor population in baseline biopsies. KDPI groups are defined in deceased-donor population as: high: KDPI>85%, intermediate: 20%<KDPI≤85%, low: KDPI≤20%. P-values are calculated by log-rank test.

FIG. 11A shows average eGFR values over time within 12-month post-transplant per baseline ITAS risk group (high: 1102; intermediate: 1104; low: 1106). Error bars represent 0.1× standard deviation from mean values. FIG. 11B shows bar charts demonstrating proportions of DGF vs. no DGF (upper panel) and 3-month post-transplant CADI>2 vs. CADI≤2 (lower panel) among three baseline ITAS risk groups in the whole population. P-values are calculated by Fisher's exact test.

FIG. 13A shows Kaplan-Meier curves of DCGL in CDS high vs. low group from AUSCAD 12-month biopsies (n=111). P-values are calculated by log-rank test. FIG. 13B shows a heatmap of time-dependent AUCs in predicting DCGL by 12-month CDS high vs. low group and other pathological and/or clinical factors which were obtained prior to or at 12 months. 12-month CDS groups are defined as: high: CDS>1.5, low: CDS≤1.5.

DETAILED DESCRIPTION

Introduction

Figure 1:
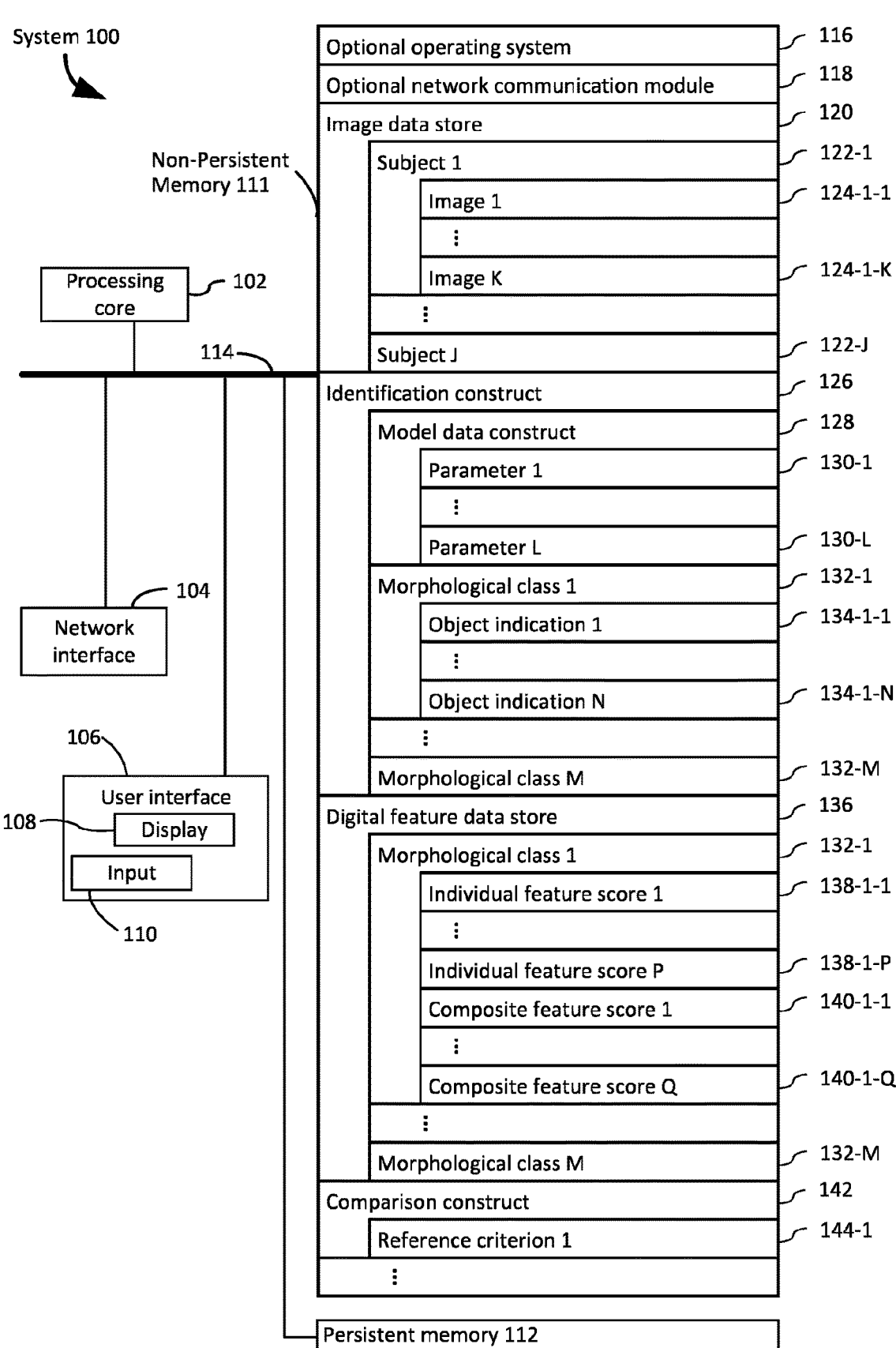
FIG. 1 illustrates an example block diagram illustrating a computing device in accordance with some embodiments of the present disclosure.
Figure 2A:
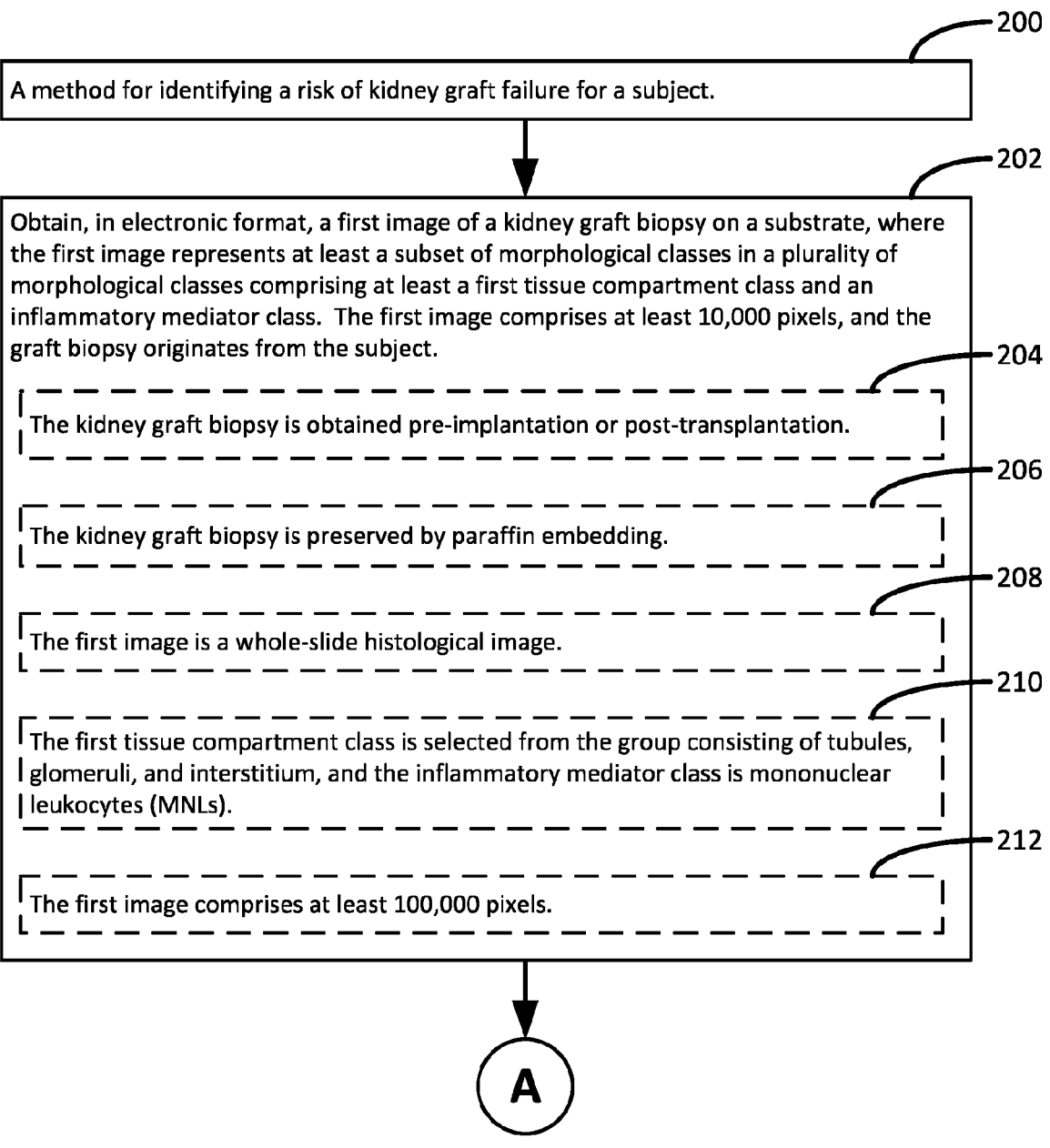

The implementations described herein provide various technical solutions for determining risk of kidney graft failure. As described above, interstitial fibrosis, tubular atrophy, and inflammation are major contributors to kidney allograft failure. These morphologies are typically graded by pathologic assessment of biopsies but, as a result, are vulnerable to subjectivity arising from inter- and intra-observer variability. Additionally, early stage indicators, such as factors obtained pre-implantation or early post-transplantation, would provide benefits for early prediction of graft loss and allow for the implementation of prevention and patient management protocols. Given the above background, there is a need in the art for improved systems and methods for determining features for identifying risk of kidney graft failure, as well as systems and methods for analyzing the same, that overcome the abovementioned limitations.

Recently, deep-learning-based approaches have been successfully applied to radiological medical images (6, 7) and histologically stained images (8, 9), and studies in renal digital pathology have shown promise in detecting glomerular or interstitial abnormalities (10-15). For instance, good prediction of kidney tissue compartments (16-18) has been obtained with pixel-level prediction algorithms such as U-Net (19). An instance-level object detection algorithm Mask Region-based Convolution Neural Network (R-CNN) (20) has also been developed with advantages of performing object localization, shape prediction, and object classification at the same time and that accurately distinguishes sclerotic from non-sclerotic glomeruli (21).

Accordingly, the present disclosure provides systems and methods that utilize deep-learning-based approaches, thus providing observer-independent histopathologic assessment of transplant biopsies and offering distinct advantages for graft prognostication.

Specifically, the systems and methods disclosed herein provide a method for identifying a risk of kidney graft failure for a subject. The method includes obtaining, in electronic format, a first image of a kidney graft biopsy on a substrate, where the first image represents at least a first subset of morphological classes in a plurality of morphological classes comprising at least a first tissue compartment class and an inflammatory mediator class, the first image comprises a plurality (e.g., at least 10,000) of pixels, and the graft biopsy originates from the subject. The first image is inputted into a trained model comprising a plurality of parameters (e.g., at least 10,000 parameters). The method further comprises identifying, as output from the trained model, for each respective morphological class in the at least the first subset of morphological classes, a corresponding one or more objects in the first image that fall within the respective morphological class, where the first subset of morphological classes includes the first tissue compartment class or the inflammatory mediator class.

For each respective morphological class in the at least the first subset of morphological classes, a corresponding plurality of digital features is generated comprising (i) a first corresponding subset of individual feature scores, where each respective individual feature score is obtained using the corresponding one or more objects for the respective morphological class, and (ii) a second corresponding subset of composite feature scores, where each respective composite feature score is obtained by combining two or more individual feature scores in the first corresponding subset of individual feature scores. For each respective morphological class in the at least the first subset of morphological classes, a respective digital feature in the corresponding plurality of digital features for the respective morphological class is compared to a reference criterion, thereby determining the risk of kidney graft failure for the subject.

An exemplary embodiment is described below in Example 1. For example, in such embodiment, the present disclosure provides a deep-learning model based on both U-Net and Mask R-CNN algorithms to accurately recognize normal and abnormal kidney tissue compartments and infiltrated mononuclear leukocytes (MNLs) in images obtained from baseline (pre-implantation) and post-transplant biopsies. Features are extracted from across full biopsy images (e.g., whole-slide images) to ensure capture of abnormalities in the interstitium and tubules and for inflammation (e.g., MNLs), and investigated for their association with Banff scores, conventionally used for representing renal injury, and post-transplant graft outcomes.

Advantageously, the presently disclosed systems and methods overcome the abovementioned limitations by using deep learning to extract digital features and analyzing such features to be predictive of both early (e.g., less than 1 year post-transplantation) and late (e.g., 1 year or more post-transplantation) graft outcomes. The systems and methods are repeatable and deterministic and can be applied to a plurality of instances in a systematic manner, avoiding issues of subjectivity that can arise with human observer assessment. Furthermore, the inputs and outputs are machine-readable and compatible with models for classification and detection, which can be used to develop automated pipelines for evaluation of kidney graft outcomes and transplant prognosis.

Additionally, compared to conventional methods for deep-learning-based kidney tissue compartment detection (16-18), the present disclosure provides several distinct improvements. For example, the presently disclosed systems and methods provide a trained model that more efficiently and accurately detects morphological classes such as tissue compartments and inflammation, and/or classifies regions and objects therein as normal or abnormal. In some embodiments, the trained model incorporates a plurality of models to achieve this detection (e.g., U-Net and Mask R-CNN architecture). As another example, the presently disclosed systems and methods detect inflammation in post-transplant biopsies (e.g., via a Mask R-CNN-based MNL detection model). Inflammation is a major contributor to graft failure, and thus the present disclosure advantageously improves graft loss predictive ability. In yet another example, the presently disclosed systems and methods generate both individual and composite features (e.g., "digital features") that describe characteristics of a plurality of morphological classes including tissue compartment and inflammatory classes (e.g., pathologic lesions and/or abnormalities in interstitium, tubules, glomeruli, and MNL infiltration, respectively) or that describe overall kidney damage. Such features can be obtained for selected areas within an image or a slide, or for full whole-slide images. Moreover, the systems and methods described herein can be successfully applied for clinical graft survival prediction in patients from heterogenous cohorts, including various race or ethnicity backgrounds, different standard-of-care protocols, and different sites.

Compared to traditional methods, the present disclosure can be used to establish a consistent association between pre-implantation or early post-transplantation (e.g., baseline) histologic findings (e.g., images and features obtained therefrom) and post-transplant outcomes (26,32). In particular, as illustrated in Example 1, below, a strong prediction power of short-term survival was demonstrated using such early stage digital features. In contrast, the major limitations of current approaches in pathologic evaluation for baseline biopsies are the variations from slide processing procedure and the expertise in transplant pathologic assessment (32, 42). For example, the Banff system has limitations by using categories rather than continuous variables (43). The deep-learning, machine-based processes disclosed herein overcome these drawbacks by producing consistent and automated results within 30 minutes from scanned images.

Accordingly, Example 1 illustrates that the digital features generated and used for determining risk of kidney graft failure are superior, in some implementations, to metrics used by conventional approaches. For instance, a composite feature score for a tissue compartment morphological class, Interstitial and Tubular Abnormality Score (ITAS) obtained using images of pre-implantation graft biopsies was superior to Banff scores for interstitial fibrosis (ci) and tubular atrophy (ct) and to a validated demographic and clinical factor Kidney Donor Profile Index (KDPI). ITAS further demonstrated a capability for stratification of risk of early graft damage, thus providing early information with utility for post-transplant monitoring, risk stratification, or potential interventional trials.

Example 1 further illustrates another digital feature, the composite damage score (CDS), that incorporates tissue compartment and inflammatory features (ITAS and MNL Infiltration Score) from biopsies obtained 12 months post-transplantation and that could be used to predict long-term graft survival, outperforming histology and clinical factors. Reporting longer-term hard outcomes from prospective trials has been an issue in kidney transplantation research (44). The identification of surrogate end points is a major unmet need that often prevents the design of adequately powered trials. Recent studies proposed using estimated glomerular filtration rate (eGFR) decline within 24 to 36 months as a long term graft loss surrogate (4,5). However, such a surrogate has the following limitations: (i) creatinine measurement is impacted by a number of factors including timing of collection in the day, diet, and interlaboratory variation (45,46); (ii) eGFR decline has low detection sensitivity because it requires multiple measurements during long-term follow-up, and the 40% decline from 6 to 24 months, as suggested by a prior study for graft loss prediction (5), was found to be under-representative of rates of graft loss in patient cohorts. In contrast, 12-month CDS was able to detect higher proportions of patient cohorts as having high risk of graft loss as early as 12 months while still exhibiting optimal performance as measured by area under curves (AUCs) in long-term graft loss prediction.

Advantageously, the present disclosure further provides various systems and methods for determining risk of kidney graft failure, where features for determining such risk are obtained computationally using a trained model for more accurate image processing and analysis. The complexity of a machine learning model includes time complexity (running time, or the measure of the speed of an algorithm for a given input size n), space complexity (space requirements, or the amount of computing power or memory needed to execute an algorithm for a given input size n), or both. Complexity (and subsequent computational burden) applies to both training of and prediction by a given model.

In some instances, computational complexity is impacted by implementation, incorporation of additional algorithms or cross-validation methods, and/or one or more parameters (e.g., weights and/or hyperparameters). In some instances, computational complexity is expressed as a function of input size n, where input data is the number of instances (e.g., the number of training samples), dimensions p (e.g., the number of features), the number of trees $n_{trees}$ (e.g., for methods based on trees), the number of support vectors $n_{sv}$ (e.g., for methods based on support vectors), the number of neighbors k (e.g., fork nearest neighbor algorithms), the number of classes c, and/or the number of neurons $n_i$ at a layer i (e.g., for neural networks). With respect to input size n, then, an approximation of computational complexity (e.g., in Big O notation) denotes how running time and/or space requirements increase as input size increases. Functions can increase in complexity at slower or faster rates relative to an increase in input size. Various approximations of computational complexity include but are not limited to constant (e.g., $O(1)$), logarithmic (e.g., $O(\log n)$), linear (e.g., $O(n)$), loglinear (e.g., $O(n \log ii)$), quadratic (e.g., $O(n^2)$), polynomial (e.g., $O(n^c)$), exponential (e.g., $O(c^n)$), and/or factorial (e.g., $O(n!)$). In some instances, simpler functions are accompanied by lower levels of computational complexity as input sizes increase, as in the case of constant functions, whereas more complex functions such as factorial functions can exhibit substantial increases in complexity in response to slight increases in input size.

Computational complexity of machine learning models can similarly be represented by functions (e.g., in Big O notation), and complexity may vary depending on the type of model, the size of one or more inputs or dimensions, usage (e.g., training and/or prediction), and/or whether time or space complexity is being assessed. For example, complexity in decision tree algorithms is approximated as $O(n^2 p)$ for training and $O(p)$ for predictions, while complexity in linear regression algorithms is approximated as $O(p^2 n + p^3)$ for training and $O(p)$ for predictions. For random forest algorithms, training complexity is approximated as $O(n^2 p n_{trees})$ and prediction complexity is approximated as $O(p n_{trees})$. For gradient boosting algorithms, complexity is approximated as $O(npn_{trees})$ for training and $O(pn_{trees})$ for predictions. For kernel support vector machines, complexity is approximated as $O(n^2 p + n^3)$ for training and $O(n_{sv} p)$ for predictions. For nave Bayes algorithms, complexity is represented as $O(pp)$ for training and $O(p)$ for predictions, and for neural networks, complexity is approximated as O(pn$_1$+ n$_1$n$_2$+ . . . ) for predictions. Complexity in K nearest neighbors algorithms is approximated as O(knp) for time and O(np) for space. For logistic regression algorithms, complexity is approximated as O(np) for time and O(p) for space. For logistic regression algorithms, complexity is approximated as O(np) for time and O(p) for space.

As described above, for machine learning models, computational complexity dictates the scalability and therefore the overall effectiveness and usability of a model (e.g., a classifier) for increasing input, feature, and/or class sizes, as well as for variations in model architecture. In the context of large-scale image processing, as when using thousands or tens of thousands of image tiles obtained from partitioning images of biopsies (described elsewhere herein), the computational complexity of functions performed on large image datasets (e.g., batches of image tiles for a plurality of training samples) may strain the capabilities of many existing systems. In addition, as the number of input features (e.g., number of pixels, image size and/or resolution) and/or the number of instances (e.g., training samples, subjects, and/or number of images per subject (e.g., for longitudinal studies monitoring subjects pre-implantation and/or post-transplantation)) increases together with technological advancements and expanding downstream applications and possibilities, the computational complexity of any given classification model can quickly overwhelm the time and space capacities provided by the specifications of a respective system.

Thus, by using a machine learning model with a minimum input size (e.g., at least 10,000, at least 20,000, or at least 100,000 pixels) and/or a minimum number of parameters (e.g., at least 1000, at least 10,000, or at least 100,000 parameters) to obtain digital features from images for use in determining risk of graft failure, the computational complexity is proportionally increased such that it cannot be mentally performed, and the method addresses a computational problem.

Additional details on computational complexity in machine learning models are provided in "Computational complexity of machine learning algorithms," published Apr. 16, 2018, available online at: thekerneltrip.com/machine/learning/computational-complexity-learning-algorithms; Hastie, 2001, *The Elements of Statistical Learning*, Springer, New York; and Arora and Barak, 2009, *Computational Complexity: A Modern Approach*, Cambridge University Press, New York; each of which is hereby incorporated herein by reference in its entirety.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Definitions

As used herein, the term "about" or "approximately" means within an acceptable error range for the particular value as determined by one of ordinary skill in the art, which depends in part on how the value is measured or determined, e.g., the limitations of the measurement system. For example, in some embodiments "about" means within 1 or more than 1 standard deviation, per the practice in the art. In some embodiments, "about" means a range of ±20%, ±10%, ±5%, or ±1% of a given value. In some embodiments, the term "about" or "approximately" means within an order of magnitude, within 5-fold, or within 2-fold, of a value. Where particular values are described in the application and claims, unless otherwise stated the term "about" meaning within an acceptable error range for the particular value can be assumed. All numerical values within the detailed description herein are modified by "about" the indicated value, and consider experimental error and variations that would be expected by a person having ordinary skill in the art. The term "about" can have the meaning as commonly understood by one of ordinary skill in the art. In some embodiments, the term "about" refers to ±10%. In some embodiments, the term "about" refers to ±5%.

As used herein, the term "subject," "training subject," or "test subject" refers to any living or non-living organism, including but not limited to a human (e.g., a male human, female human, fetus, pregnant female, child, or the like) and/or a non-human animal. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale, and shark. The terms "subject" and "patient" are used interchangeably herein and can refer to a human or non-human animal who is known to have, or potentially has, a medical condition or disorder, such as, e.g., kidney disease. In some embodiments, a subject is a "normal" or "control" subject, e.g., a subject that is not known to have a medical condition or disorder. In some embodiments, a subject is a male or female of any stage (e.g., a man, a woman, or a child).

A subject from whom an image and/or biopsy is obtained using any of the methods or systems described herein can be of any age and can be an adult, infant or child. In some cases, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between about 2 and about 20 years old, between about 20 and about 40 years old, or between about 40 and about 90 years old).

As used herein, the terms "control," "healthy," and "normal" describe a subject and/or an image from a subject that does not have a particular condition (e.g., kidney disease), has a baseline condition (e.g., prior to onset of the particular condition), or is otherwise healthy. In an example, a method as disclosed herein can be performed to diagnose a renal disease and/or a kidney graft failure in a subject having a renal disease using a trained model, where the model is trained using one or more training images obtained from the subject prior to the onset of the condition (e.g., at an earlier time point), or from a different, healthy subject. A control image can be obtained from a control subject, or from a database.

The term "normalize" as used herein means transforming a value or a set of values to a common frame of reference for comparison purposes. For example, when one or more pixel values corresponding to one or more pixels in a respective image are "normalized" to a predetermined statistic (e.g., a mean and/or standard deviation of one or more pixel values across one or more images), the pixel values of the respective pixels are compared to the respective statistic so that the amount by which the pixel values differ from the statistic can be determined.

As used herein, the term "untrained model" (e.g., "untrained classifier" and/or "untrained neural network") refers to a machine learning model or algorithm, such as a classifier or a neural network, that has not been trained on a target dataset. In some embodiments, "training a model" (e.g., "training a neural network") refers to the process of training an untrained or partially trained model (e.g., "an untrained or partially trained neural network"). For instance, consider the case of a plurality of training samples comprising a corresponding plurality of images discussed below. The plurality of images are applied as collective input to an untrained or partially trained model, in conjunction with a corresponding measured indication of one or more objects for each respective image (hereinafter "training dataset") to train the untrained or partially trained model on indications that identify objects related to morphological classes, thereby obtaining a trained model. Moreover, it will be appreciated that the term "untrained model" does not exclude the possibility that transfer learning techniques are used in such training of the untrained or partially trained model. For instance, Fernandes et al., 2017, "Transfer Learning with Partial Observability Applied to Cervical Cancer Screening," Pattern Recognition and Image Analysis: $8^{th}$ Iberian Conference Proceedings, 243-250, which is hereby incorporated by reference, provides non-limiting examples of such transfer learning. In instances where transfer learning is used, the untrained model described above is provided with additional data over and beyond that of the primary training dataset. That is, in non-limiting examples of transfer learning embodiments, the untrained model receives (i) the plurality of images and the measured indications for each respective image ("primary training dataset") and (ii) additional data. Typically, this additional data is in the form of parameters (e.g., coefficients, weights, and/or hyperparameters) that were learned from another, auxiliary training dataset. Moreover, while a description of a single auxiliary training dataset has been disclosed, it will be appreciated that there is no limit on the number of auxiliary training datasets that may be used to complement the primary training dataset in training the untrained model in the present disclosure. For instance, in some embodiments, two or more auxiliary training datasets, three or more auxiliary training datasets, four or more auxiliary training datasets or five or more auxiliary training datasets are used to complement the primary training dataset through transfer learning, where each such auxiliary dataset is different than the primary training dataset. Any manner of transfer learning may be used in such embodiments. For instance, consider the case where there is a first auxiliary training dataset and a second auxiliary training dataset in addition to the primary training dataset. The parameters learned from the first auxiliary training dataset (by application of a first model to the first auxiliary training dataset) may be applied to the second auxiliary training dataset using transfer learning techniques (e.g., a second model that is the same or different from the first model), which in turn may result in a trained intermediate model whose parameters are then applied to the primary training dataset and this, in conjunction with the primary training dataset itself, is applied to the untrained model. Alternatively, a first set of parameters learned from the first auxiliary training dataset (by application of a first model to the first auxiliary training dataset) and a second set of parameters learned from the second auxiliary training dataset (by application of a second model that is the same or different from the first model to the second auxiliary training dataset) may each individually be applied to a separate instance of the primary training dataset (e.g., by separate independent matrix multiplications) and both such applications of the parameters to separate instances of the primary training dataset in conjunction with the primary training dataset itself (or some reduced form of the primary training dataset such as principal components or regression coefficients learned from the primary training set) may then be applied to the untrained model in order to train the untrained model. In some instances, additionally or alternatively, knowledge regarding objects related to morphological classes (e.g., tubules, glomeruli, interstitium, MNLs, etc.) derived from an auxiliary training dataset is used, in conjunction with the object and/or class-labeled images in the primary training dataset, to train the untrained model.

As used herein, the term "model" refers to a machine learning model or algorithm.

In some embodiments, a model is an unsupervised learning algorithm. One example of an unsupervised learning algorithm is cluster analysis.

In some embodiments, a model is supervised machine learning. Nonlimiting examples of supervised learning algorithms include, but are not limited to, logistic regression, neural networks, support vector machines, Naive Bayes algorithms, nearest neighbor algorithms, random forest algorithms, decision tree algorithms, boosted trees algorithms, multinomial logistic regression algorithms, linear models, linear regression, GradientBoosting, mixture models, hidden Markov models, Gaussian NB algorithms, linear discriminant analysis, or any combinations thereof. In some embodiments, a model is a multinomial classifier algorithm. In some embodiments, a model is a 2-stage stochastic gradient descent (SGD) model. In some embodiments, a model is a deep neural network (e.g., a deep-and-wide sample-level classifier).

Neural networks. In some embodiments, the model is a neural network (e.g., a convolutional neural network and/or a residual neural network). Neural network algorithms, also known as artificial neural networks (ANNs), include convolutional and/or residual neural network algorithms (deep learning algorithms). Neural networks can be machine learning algorithms that may be trained to map an input data set to an output data set, where the neural network comprises an interconnected group of nodes organized into multiple layers of nodes. For example, the neural network architecture may comprise at least an input layer, one or more hidden layers, and an output layer. The neural network may comprise any total number of layers, and any number of hidden layers, where the hidden layers function as trainable feature extractors that allow mapping of a set of input data to an output value or set of output values. As used herein, a deep learning algorithm (DNN) can be a neural network comprising a plurality of hidden layers, e.g., two or more hidden layers. Each layer of the neural network can comprise a number of nodes (or "neurons"). A node can receive input that comes either directly from the input data or the output of nodes in previous layers, and perfom a specific operation, e.g., a summation operation. In some embodiments, a connection from an input to a node is associated with a parameter (e.g., a weight and/or weighting factor). In some embodiments, the node may sum up the products of all pairs of inputs, xi, and their associated parameters. In some embodiments, the weighted sum is offset with a bias, b. In some embodiments, the output of a node or neuron may be gated using a threshold or activation function, f, which may be a linear or non-linear function. The activation function may be, for example, a rectified linear unit (ReLU) activation function, a Leaky ReLU activation function, or other function such as a saturating hyperbolic tangent, identity, binary step, logistic, arcTan, softsign, parametric rectified linear unit, exponential linear unit, softPlus, bent identity, softExponential, Sinusoid, Sine, Gaussian, or sigmoid function, or any combination thereof.

The weighting factors, bias values, and threshold values, or other computational parameters of the neural network, may be "taught" or "learned" in a training phase using one or more sets of training data. For example, the parameters may be trained using the input data from a training data set and a gradient descent or backward propagation method so that the output value(s) that the ANN computes are consistent with the examples included in the training data set. The parameters may be obtained from a back propagation neural network training process.

Any of a variety of neural networks may be suitable for use in performing the methods disclosed herein. Examples can include, but are not limited to, feedforward neural networks, radial basis function networks, recurrent neural networks, residual neural networks, convolutional neural networks, residual convolutional neural networks, and the like, or any combination thereof. In some embodiments, the machine learning makes use of a pre-trained and/or transfer-learned ANN or deep learning architecture. Convolutional and/or residual neural networks can be used for analyzing an image of a subject in accordance with the present disclosure.

For instance, a deep neural network model comprises an input layer, a plurality of individually parameterized (e.g., weighted) convolutional layers, and an output scorer. The parameters (e.g., weights) of each of the convolutional layers as well as the input layer contribute to the plurality of parameters (e.g., weights) associated with the deep neural network model. In some embodiments, at least 100 parameters, at least 1000 parameters, at least 2000 parameters or at least 5000 parameters are associated with the deep neural network model. As such, deep neural network models require a computer to be used because they cannot be mentally solved. In other words, given an input to the model, the model output needs to be determined using a computer rather than mentally in such embodiments. See, for example, Krizhevsky et al., 2012, "Imagenet classification with deep convolutional neural networks," in Advances in Neural Information Processing Systems 2, Pereira, Burges, Bottou, Weinberger, eds., pp. 1097-1105, Curran Associates, Inc.; Zeiler, 2012 "ADADELTA: an adaptive learning rate method," CoRR, vol. abs/1212.5701; and Rumelhart et al., 1988, "Neurocomputing: Foundations of research," ch. Learning Representations by Back-propagating Errors, pp. 696-699, Cambridge, MA, USA: MIT Press, each of which is hereby incorporated by reference.

Neural network algorithms, including convolutional neural network algorithms, suitable for use as models are disclosed in, for example, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference. Additional example neural networks suitable for use as models are disclosed in Duda et al., 2001, *Pattern*

*Classification*, Second Edition, John Wiley & Sons, Inc., New York; and Hastie et al., 2001, *The Elements of Statistical Learning*, Springer-Verlag, New York, each of which is hereby incorporated by reference in its entirety. Additional example neural networks suitable for use as models are also described in Draghici, 2003, *Data Analysis Tools for DNA Microarrays*, Chapman & Hall/CRC; and Mount, 2001, *Bioinformatics: sequence and genome analysis*, Cold Spring Harbor Laboratory Press, Cold Spring Harbor, New York, each of which is hereby incorporated by reference in its entirety.

Support Vector machines. In some embodiments, the model is a support vector machine (SVM). SVM algorithms suitable for use as models are described in, for example, Cristianini and Shawe-Taylor, 2000, "An Introduction to Support Vector Machines," Cambridge University Press, Cambridge; Boser et al., 1992, "A training algorithm for optimal margin classifiers," in Proceedings of the 5th Annual ACM Workshop on Computational Learning Theory, ACM Press, Pittsburgh, Pa., pp. 142-152; Vapnik, 1998, Statistical Learning Theory, Wiley, New York; Mount, 2001, Bioinfonnatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety. When used for classification, SVMs separate a given set of binary labeled data with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space can correspond to a non-linear decision boundary in the input space. In some embodiments, the plurality of parameters (e.g., weights) associated with the SVM define the hyper-plane. In some embodiments, the hyper-plane is defined by at least 10, at least 20, at least 50, or at least 100 parameters and the SVM model requires a computer to calculate because it cannot be mentally solved.

Naïve Bayes algorithms. In some embodiments, the model is a Naive Bayes algorithm. Naïve Bayes classifiers suitable for use as models are disclosed, for example, in Ng et al., 2002, "On discriminative vs. generative classifiers: A comparison of logistic regression and naive Bayes," Advances in Neural Information Processing Systems, 14, which is hereby incorporated by reference. A Naive Bayes classifier is any classifier in a family of "probabilistic classifiers" based on applying Bayes' theorem with strong (naïve) independence assumptions between the features. In some embodiments, they are coupled with Kernel density estimation. See, for example, Hastie et al., 2001, *The elements of statistical learning: data mining, inference, and prediction*, eds. Tibshirani and Friedman, Springer, New York, which is hereby incorporated by reference.

Nearest neighbor algorithms. In some embodiments, a model is a nearest neighbor algorithm. Nearest neighbor models can be memory-based and include no model to be fit. For nearest neighbors, given a query point $x_0$ (a first image), the k training points $x_{(r)}$, r, . . . , k (here the training images) closest in distance to $x_0$ are identified and then the point $x_0$ is classified using the k nearest neighbors. In some embodiments, the distance to these neighbors is a function of the values of a discriminating set. In some embodiments, Euclidean distance in feature space is used to determine distance as $d_{(i)}=\|x_{(i)}-x_{(o)}\|$. Typically, when the nearest neighbor algorithm is used, the value data used to compute the linear discriminant is standardized to have mean zero and variance 1. The nearest neighbor rule can be refined to address issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, The Elements of Statistical Learning, Springer, New York, each of which is hereby incorporated by reference.

A k-nearest neighbor model is a non-parametric machine learning method in which the input consists of the k closest training examples in feature space. The output is a class membership. An object is classified by a plurality vote of its neighbors, with the object being assigned to the class most common among its k nearest neighbors (k is a positive integer, typically small). If k=1, then the object is simply assigned to the class of that single nearest neighbor. See, Duda et al., 2001, *Pattern Classification*, Second Edition, John Wiley & Sons, which is hereby incorporated by reference. In some embodiments, the number of distance calculations needed to solve the k-nearest neighbor model is such that a computer is used to solve the model for a given input because it cannot be mentally performed.

Random forest, decision tree, and boosted tree algorithms. In some embodiments, the model is a decision tree. Decision trees suitable for use as models are described generally by Duda, 2001, Pattern Classification, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4-5, MART, and Random Forests. CART, ID3, and C4-5 are described in Duda, 2001, Pattern Classification, John Wiley & Sons, Inc., New York, pp. 396-408 and pp. 411-412, which is hereby incorporated by reference. CART, MART, and C4-5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety. In some embodiments, the decision tree model includes at least 10, at least 20, at least 50, or at least 100 parameters (e.g., weights and/or decisions) and requires a computer to calculate because it cannot be mentally solved.

Regression. In some embodiments, the model uses a regression algorithm. A regression algorithm can be any type of regression. For example, in some embodiments, the regression algorithm is logistic regression. In some embodiments, the regression algorithm is logistic regression with lasso, L2 or elastic net regularization. In some embodiments, those extracted features that have a corresponding regression coefficient that fails to satisfy a threshold value are pruned (removed from) consideration. In some embodiments, a generalization of the logistic regression model that handles multicategory responses is used as the model. Logistic regression algorithms are disclosed in Agresti, An Introduction to Categorical Data Analysis, 1996, Chapter 5, pp. 103-144, John Wiley & Son, New York, which is hereby incorporated by reference. In some embodiments, the model makes use of a regression model disclosed in Hastie et al., 2001, *The Elements of Statistical Learning*, Springer-Verlag, New York. In some embodiments, the logistic regression model includes at PTO least 10, at least 20, at least 50, at least 100, or at least 1000 parameters (e.g., weights) and requires a computer to calculate because it cannot be mentally solved.

Linear discriminant analysis algorithms. Linear discriminant analysis (LDA), normal discriminant analysis (NDA), or discriminant function analysis can be a generalization of Fisher's linear discriminant, a method used in statistics, pattern recognition, and machine learning to find a linear combination of features that characterizes or separates two or more classes of objects or events. The resulting combination can be used as the model (e.g., a linear classifier) in some embodiments of the present disclosure.

Mixture model and Hidden Markov model. In some embodiments, the model is a mixture model, such as that described in McLachlan et al., Bioinformatics 18(3):413-422, 2002. In some embodiments, in particular, those embodiments including a temporal component, the model is a hidden Markov model such as described by Schliep et al., 2003, Bioinformatics 19(1):i255-i263.

Clustering. In some embodiments, the model is an unsupervised clustering model. In some embodiments, the model is a supervised clustering model. Clustering algorithms suitable for use as models are described, for example, at pages 211-256 of Duda and Hart, Pattern Classification and Scene Analysis, 1973, John Wiley & Sons, Inc., New York, (hereinafter "Duda 1973") which is hereby incorporated by reference in its entirety. The clustering problem can be described as one of finding natural groupings in a dataset. To identify natural groupings, two issues can be addressed. First, a way to measure similarity (or dissimilarity) between two samples can be determined. This metric (e.g., similarity measure) can be used to ensure that the samples in one cluster are more like one another than they are to samples in other clusters. Second, a mechanism for partitioning the data into clusters using the similarity measure can be determined. One way to begin a clustering investigation can be to define a distance function and to compute the matrix of distances between all pairs of samples in a training dataset. If distance is a good measure of similarity, then the distance between reference entities in the same cluster can be significantly less than the distance between the reference entities in different clusters. However, clustering may not use a distance metric. For example, a nonmetric similarity function s(x, x') can be used to compare two vectors x and x'. s(x, x') can be a symmetric function whose value is large when x and x' are somehow "similar." Once a method for measuring "similarity" or "dissimilarity" between points in a dataset has been selected, clustering can use a criterion function that measures the clustering quality of any partition of the data. Partitions of the data set that extremize the criterion function can be used to cluster the data. Particular exemplary clustering techniques that can be used in the present disclosure can include, but are not limited to, hierarchical clustering (agglomerative clustering using a nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering. In some embodiments, the clustering comprises unsupervised clustering (e.g., with no preconceived number of clusters and/or no predetermination of cluster assignments).

Ensembles of models and boosting. In some embodiments, an ensemble (two or more) of models is used. In some embodiments, a boosting technique such as AdaBoost is used in conjunction with many other types of learning algorithms to improve the performance of the model. In this approach, the output of any of the models disclosed herein, or their equivalents, is combined into a weighted sum that represents the final output of the boosted model. In some embodiments, the plurality of outputs from the models is combined using any measure of central tendency known in the art, including but not limited to a mean, median, mode, a weighted mean, weighted median, weighted mode, etc. In some embodiments, the plurality of outputs is combined using a voting method. In some embodiments, a respective model in the ensemble of models is weighted or unweighted.

The term "classification" can refer to any number(s) or other characters(s) that are associated with a particular property of a sample. For example, a "+" symbol (or the word "positive") can signify that a sample is classified as having a desired outcome or characteristic, whereas a "−" symbol (or the word "negative") can signify that a sample is classified as having an undesired outcome or characteristic. In another example, the term "classification" refers to a respective outcome or characteristic (e.g., high risk, medium risk, low risk). In some embodiments, the classification is binary (e.g., positive or negative) or has more levels of classification (e.g., a scale from 1 to 10 or 0 to 1). In some embodiments, the terms "cutoff" and "threshold" refer to predetermined numbers used in an operation. In one example, a cutoff value refers to a value above which results are excluded. In some embodiments, a threshold value is a value above or below which a particular classification applies. Either of these terms can be used in either of these contexts.

As used herein, the term "parameter" refers to any coefficient or, similarly, any value of an internal or external element (e.g., a weight and/or a hyperparameter) in an algorithm, model, regressor, and/or classifier that can affect (e.g., modify, tailor, and/or adjust) one or more inputs, outputs, and/or functions in the algorithm, model, regressor and/or classifier. For example, in some embodiments, a parameter refers to any coefficient, weight, and/or hyperparameter that can be used to control, modify, tailor, and/or adjust the behavior, learning, and/or performance of an algorithm, model, regressor, and/or classifier. In some instances, a parameter is used to increase or decrease the influence of an input (e.g., a feature) to an algorithm, model, regressor, and/or classifier. As a nonlimiting example, in some embodiments, a parameter is used to increase or decrease the influence of a node (e.g., of a neural network), where the node includes one or more activation functions. Assignment of parameters to specific inputs, outputs, and/or functions is not limited to any one paradigm for a given algorithm, model, regressor, and/or classifier but can be used in any suitable algorithm, model, regressor, and/or classifier architecture for a desired performance. In some embodiments, a parameter has a fixed value. In some embodiments, a value of a parameter is manually and/or automatically adjustable. In some embodiments, a value of a parameter is modified by a validation and/or training process for an algorithm, model, regressor, and/or classifier (e.g., by error minimization and/or backpropagation methods). In some embodiments, an algorithm, model, regressor, and/or classifier of the present disclosure includes a plurality of parameters. In some embodiments, the plurality of parameters is n parameters, where: $n \geq 2$; $n \geq 5$; $n \geq 10$; $n \geq 25$; $n \geq 40$; $n \geq 50$; $n \geq 75$; $n \geq 100$; $n \geq 125$; $n \geq 150$; $n \geq 200$; $n \geq 225$; $n \geq 250$; $n \geq 350$; $n \geq 500$; $n \geq 600$; $n \geq 750$; $n \geq 1,000$; $n \geq 2,000$; $n \geq 4,000$; $n \geq 5,000$; $n \geq 7,500$; $n \geq 10,000$; $n \geq 20,000$; $n \geq 40,000$; $n \geq 75,000$; $n \geq 100,$ $000$; $n \geq 200,000$; $n \geq 500,000$, $n \geq 1 \times 10^6$, $n \geq 5 \times 10^6$, or $n \geq 1 \times 10^7$. As such, the algorithms, models, regressors, and/or classifiers of the present disclosure cannot be mentally performed. In some embodiments n is between 10,000 and $1 \times 10^7$, between 100,000 and $5 \times 10^6$, or between 500,000 and $1 \times 10^6$. In some embodiments, the algorithms, models, regressors, and/or classifier of the present disclosure operate in a k-dimensional space, where k is a positive integer of 5 or greater (e.g., 5, 6, 7, 8, 9, 10, etc.). *As such, the algorithms, models,* regressors, and/or classifiers of the present disclosure cannot be mentally performed.

Several aspects are described below with reference to example applications for illustration. Numerous specific details, relationships, and methods are set forth to provide a full understanding of the features described herein. The features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are used to implement a methodology in accordance with the features described herein.

Exemplary System Embodiments

Details of an exemplary system are now described in conjunction with FIG. 1. FIG. 1 is a block diagram illustrating system 100 in accordance with some implementations. System 100 in some implementations includes one or more processing units CPU(s) 102 (also referred to as processors or processing core), one or more network interfaces 104, user interface 106, display 108, input 110, non-persistent memory 111, persistent memory 112, and one or more communication buses 114 for interconnecting these components. One or more communication buses 114 optionally include circuitry (sometimes called a chipset) that interconnects and controls communications between system components. Non-persistent memory 111 typically includes high-speed random access memory, such as DRAM, SRAM, DDR RAM, ROM, EEPROM, flash memory, whereas persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid-state storage devices. Persistent memory 112 optionally includes one or more storage devices remotely located from the CPU(s) 102. Persistent memory 112, and the non-volatile memory device(s) within non-persistent memory 112, comprise non-transitory computer-readable storage medium. In some implementations, non-persistent memory 111 or alternatively non-transitory computer-readable storage medium stores the following programs, modules and data structures, or a subset thereof, sometimes in conjunction with persistent memory 112:

instructions, programs, data, or information associated with an optional operating system 116, which includes procedures for handling various basic system services and for performing hardware dependent tasks;

instructions, programs, data, or information associated with an optional network communication module 118 for connecting the system 100 with other devices, or a communication network;

instructions, programs, data, or information associated with an image data store 120 that includes at least a first image 124 (e.g., 124-1-1, . . . 124-1-K) of at least a first respective subject 122 (e.g., 122-1, . . . 122-J), where
the first image 124 represents at least a first subset of
morphological classes 132 (e.g., 132-1, . . . 132-M) in
a plurality of morphological classes;

instructions, programs, data, or information associated
with an identification construct 126 for:

inputting the first image 124 into a trained model 128,
where the trained model comprises a plurality of
(e.g., at least 10,000) parameters 130 (e.g.,
130-1, . . . 130-L), and identifying, as output from the trained model 128, for
each respective morphological class 132 in at least
the first subset of morphological classes, a corre-
sponding one or more objects 134 (e.g.,
134-1-1, . . . 134-1-N) in the first image 124 that fall
within the respective morphological class;

instructions, programs, data, or information associated
with a digital feature data store 136 for generating, for
each respective morphological class 132 in the at least
the first subset of morphological classes, a correspond-
ing plurality of digital features comprising:

a first corresponding subset of individual feature scores
138 (e.g., 138-1-1, . . . 138-1-P), where each respec-
tive individual feature score is obtained using the
corresponding one or more objects 134 for the
respective morphological class, and a second corresponding subset of composite feature
scores 140 (e.g., 140-1-1, . . . 140-1-Q), where each
respective composite feature score is obtained by
combining two or more individual feature scores 138
in the first corresponding subset of individual feature
scores; and instructions, programs, data, or information associated
with a comparison construct 142 for comparing, for
each respective morphological class 132 in the at least
the first subset of morphological classes, a respective
digital feature in the corresponding plurality of digital
features 136 for the respective morphological class to at
least a first reference criterion 144-1.

In some implementations, one or more of the above-
identified elements are stored in one or more of the previ-
ously mentioned memory devices and correspond to a set of
instructions for performing a function described above. The
above-identified modules, data, or programs (e.g., sets of
instructions) may not be implemented as separate software
programs, procedures, datasets, or modules, and thus various
subsets of these modules and data may be combined or
otherwise re-arranged in various implementations. In some
implementations, the non-persistent memory 111 optionally
stores a subset of the modules and data structures identified
above. Furthermore, in some embodiments, the memory
stores additional modules and data structures not described
above. In some embodiments, one or more of the above-
identified elements is stored in a computer system, other
than that of visualization system 100, that is addressable by
visualization system 100 so that visualization system 100
may retrieve all or a portion of such data.

Although FIG. 1 depicts a "system 100," the figure is
intended more as functional description of the various
features which may be present in computer systems than as
a structural schematic of the implementations described
herein. In practice, items shown separately could be com-
bined and some items can be separated. Moreover, although
FIG. 1 depicts certain data and modules in non-persistent
memory 111, some or all of these data and modules may be
in persistent memory 112.

While a system in accordance with the present disclosure
has been disclosed with reference to FIG. 1, methods in
accordance with the present disclosure are now detailed with
reference to FIGS. 2A-F.

Embodiments for Identifying Risk of Kidney Graft Failure.

In the described embodiments, an overview of the tech-
niques in accordance with some embodiments of the present
disclosure, including various methods of identifying a risk
of kidney graft failure for a subject, are provided. In par-
ticular, FIGS. 2A-F collectively illustrate a method 200 for
identifying a risk of kidney graft failure for a subject 122. In
some embodiments, the method is performed at a computer
system comprising at least one processor and a memory
storing at least one program comprising instructions for
execution by the at least one processor.

Referring to Block 202, the method includes obtaining, in
electronic format, a first image of a kidney graft biopsy on
a substrate, where the first image 124 represents at least a
first subset of morphological classes 132 in a plurality of
morphological classes comprising at least a first tissue
compartment class and an inflammatory mediator class, the
first image comprises at plurality (e.g., at least 10,000) of
pixels, and the graft biopsy originates from the subject.

Kidney Graft Biopsies

In some embodiments, the subject 122 is any subject
disclosed herein (see, e.g., the section entitled "Definitions:
Subjects," above). In some embodiments, the subject is
selected from a plurality of subjects. For instance, in some
embodiments, the method is performed for each subject in a
plurality of subjects. In some embodiments, the plurality of
subjects comprises at least 2, at least 5, at least 10, at least
20, at least 50, at least 100, at least 200, at least 500, at least
1000, at least 2000, at least 5000, at least 10,000, at least
20,000, or at least 50,000 subjects. In some embodiments,
the plurality of subjects comprises no more than 100,000, no
more than 50,000, no more than 10,000, no more than 5000,
no more than 1000, no more than 500, no more than 100, or
no more than 50 subjects. In some embodiments, the plu-
rality of subjects consists of from 5 to 20, from 2 to 10, from
15 to 80, from 50 to 200, from 100 to 500, from 200 to 5000,
from 1000 to 10,000, from 10,000 to 50,000, or from 50,000
to 100,000 subjects. In some embodiments, the plurality of
subjects falls within another range starting no lower than 2
subjects and ending no higher than 100,000 subjects.

In some embodiments, the subject is a kidney transplant
patient or candidate. In some embodiments, the subject has
a renal disease, such as end-stage renal disease.

In some embodiments, the graft biopsy is a protocol
biopsy or a for-cause biopsy. In some embodiments, the
method comprises obtaining a plurality of graft biopsies
from the subject. In some embodiments, the graft biopsy is
a biopsy in a series of biopsies, such as for a prospective
study and/or a longitudinal study. In some embodiments, the
method comprises monitoring the subject over period of
time. In some embodiments, the period of time is at least 1
day, at least 1 week, at least 1 month, at least 6 months, at
least 1 year, at least 2 years, at least 3 years, or at least 5
years.

Referring to Block 204, in some embodiments, the kidney
graft biopsy is obtained pre-implantation (e.g., baseline) or
post-transplantation.

In some embodiments, the kidney graft biopsy is obtained
at least a first predetermined period of time pre-implanta-
tion. In some embodiments, the first predetermined period of
time is no more than 1 month, no more than 1 week, no more
than 1 day, no more than 12 hours, or no more than 1 hour
pre-implantation. In some embodiments, the first predetermined period of time is at least 30 minutes, at least 1 hour, at least 1 day, or at least 1 week pre-implantation. In some embodiments, the first predetermined period of time is from 30 minutes to 1 hour, from 1 hour to 12 hours, from 1 hour to 1 day, from 1 day to 1 week, or from 1 week to 1 month. In some embodiments, the first predetermined period of time falls within another range starting no lower than 30 minutes and ending no higher than 1 month.

In some embodiments, the kidney graft biopsy is obtained at least a second predetermined period of time post-transplantation. In some embodiments, the second predetermined period of time is at least 1 hour, at least 12 hours, at least 1 day, at least 1 week, at least 1 month, at least 6 months, at least 1 year, at least 2 years, at least 3 years, or at least 5 years. In some embodiments, the second predetermined period of time is no more than 10 years, no more than 5 years, no more than 3 years, no more than 1 year, no more than 6 months, no more than 1 month, no more than 1 week, or no more than 1 day. In some embodiments, the second predetermined period of time is from 1 hour to 1 day, from 1 day to 1 week, from 1 week to 1 month, from 1 month to 1 year, from 6 months to 4 years, or from 1 year to 10 years. In some embodiments, the second predetermined period of time falls within another range starting no lower than 1 hour and ending no higher than 10 years.

In some embodiments, the kidney graft biopsy is obtained immediately upon implantation.

Referring to Block 206, in some embodiments, the kidney graft biopsy is preserved by paraffin embedding. In some embodiments, the kidney graft biopsy is formalin-fixed.

In some embodiments, the kidney graft biopsy is mounted on a substrate. For example, in some embodiments, the kidney graft biopsy is attached to a slide.

In some embodiments, the kidney graft biopsy is stained after the formalin-fixing and paraffin-embedding. In some embodiments, the kidney graft biopsy is stained for imaging, thus obtaining a histological slide where one or more morphologies of the kidney graft biopsy on the substrate can be visualized.

In some embodiments, the kidney graft biopsy is prepared for imaging on the substrate using a detectable marker selected from the group consisting of an antibody, a fluorescent label (e.g., a fluorophore), a radioactive label, a chemiluminescent label, a calorimetric label, a colorimetric label, and/or a combination thereof. For instance, in some embodiments, the kidney graft biopsy is prepared for imaging on the substrate using a stain selected from the group consisting of: live/dead stain, trypan blue, periodic acid-Schiff reaction stain, Masson's trichrome, Alcian blue, van Gieson, reticulin, Azan, Giemsa, Toluidine blue, isamin blue, sudan black and osmium, acridine orange, Bismarck brown, carmine, Coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, safranin, or a combination thereof.

In some embodiments, the kidney graft biopsy is prepared for imaging using periodic acid-Schiff (PAS).

Accordingly, referring to Block 208, in some embodiments, the first image is a whole-slide histological image.

In some embodiments, the first image (and/or the histological slide from which the first image is obtained) represents one or more morphological classes of histological structures that can be visualized in the image. In some such embodiments, the one or more morphological classes represented in the first image (and/or the respective histological slide) include pathological lesions related to kidney damage and/or kidney graft failure.

In some embodiments, the one or more morphological classes comprises at least 2, at least 3, at least 4, at least 5, at least 6, at least 7, at least 8, at least 9, or at least 10 morphological classes. In some embodiments, the one or more morphological classes comprises no more than 20, no more than 10, no more than 8, no more than 5, or no more than 3 morphological classes. In some embodiments, the one or more morphological classes consists of from 2 to 5, from 3 to 8, from 10 to 20, or from 5 to 15 morphological classes. In some embodiments, the one or more morphological classes falls within another range starting no lower than 2 morphological classes and ending no higher than 20 morphological classes.

In some embodiments, the one or more morphological classes is a plurality of morphological classes.

In some embodiments, the plurality of morphological classes includes at least a first tissue compartment class and an inflammatory mediator class.

Referring to Block 210, in some embodiments, the first tissue compartment class is selected from the group consisting of tubules, glomeruli, and interstitium, and the inflammatory mediator class is mononuclear leukocytes (MNLs).

In some embodiments, the plurality of morphological classes includes at least a second tissue compartment class selected from the group consisting of tubules, glotneruli, and interstitium. For example, in some embodiments, one of the first and second tissue compartment classes comprises tubules, and the other of the first and second tissue compartment classes comprises interstitium. In some embodiments, one of the first and second tissue compartment classes comprises tubules and glomeruli, and the other of the first and second tissue compartment classes comprises interstitium.

Accordingly, in some embodiments, the plurality of morphological classes encompasses at least tubules, interstitium, and mononuclear leukocytes (MNLs).

In some embodiments, each respective morphological class in the plurality of morphological classes represents a morphology that contributes to kidney graft failure. For example, as described above, interstitial fibrosis, tubular atrophy, and inflammation are major contributors to kidney allograft failure.

In some embodiments, the first image represents at least a first subset of morphological classes in a plurality of morphological classes.

In some embodiments, the first subset of morphological classes includes the first tissue compartment class or the inflammatory mediator class. In some embodiments, the first subset of morphological classes includes the first tissue compartment class and the inflammatory mediator class. In some embodiments, the first subset of morphological classes includes the first tissue compartment class, the second tissue compartment class, and the inflammatory mediator class. In some embodiments, the first subset of morphological classes is all of the morphological classes in the plurality of morphological classes.

In some embodiments, the first subset of morphological classes includes tubules, glomeruli, interstitium, and/or MNLs.

In some embodiments, the first subset of morphological classes includes at least 1, at least 2, at least 3, at least 4, at least 5, at least 6, at least 7, at least 8, at least 9, or at least 10 morphological classes. In some embodiments, the first subset of morphological classes comprises no more than 20, no more than 10, no more than 8, no more than 5, or no more than 3 morphological classes. In some embodiments, the first subset of morphological classes consists of from 1 to 5, from 2 to 8, from 10 to 20, or from 5 to 15 morphological classes. In some embodiments, the first subset of morphological classes falls within another range starting no lower than 1 morphological class and ending no higher than 20 morphological classes.

In some embodiments, the method includes scoring the first image (and/or the histological slide from which the first image is obtained), thus annotating the first image with one or more measured indications of one or more objects that fall within each respective morphological class in the first subset of morphological classes. For instance, in some embodiments, the one or more measured indications indicate the location, within the first image, of one or more tissue compartment classes and/or inflammatory marker classes. In some embodiments, the one or more measured indications indicate the location, within the first image, of one or more tubules, glomeruli, interstitium, and/or MNLs. For example, as described below in Example 1, in some embodiments, interstitium is defined as intertubular, nonglomerular space within tissue sections.

In some embodiments, the scoring further comprises annotating the first image with, for each respective object that falls within each respective morphological class in the first subset of morphological classes, a respective condition for the respective object. In some embodiments, the condition is abnormal or normal. Accordingly, in some embodiments, the one or more measured indications indicate the location, within the first image, of one or more normal or abnormal tubules and/or one or more normal or abnormal glomeruli. For example, as described below in Example 1, in some embodiments, abnormal tubules are defined as shrunken tubules with a thickened and wrinkled membrane.

In some embodiments, the scoring is performed by one or more clinicians, pathologists, and/or medical practitioners.

Additional embodiments for subjects, samples, kidney graft biopsies, and methods of obtaining the same are further described in Yi et al., "Deep learning identified pathological abnormalities predictive of graft loss in kidney transplant biopsies," Kidney International (2022) 101, 288-298; doi: 10.1016/j.kint.2021.09.028, which is hereby incorporated herein by reference in its entirety.

Images.

As described above, in some embodiments, the first image 124 is a whole-slide histological image. In some embodiments, the first image is a portion of a whole-slide image (e.g., an image tile).

In some embodiments, the first image is obtained by light microscopy, immunohistochemistry, expansion microscopy, electron microscopy, fluorescence microscopy, reflection microscopy, interference microscopy, confocal microscopy, and/or any combinations thereof.

In some embodiments, the first image is a bright-field microscopy image. For instance, in some embodiments, the first image is acquired using transmission light microscopy (e.g., bright-field transmission light microscopy, dark-field transmission light microscopy, oblique illumination transmission light microscopy, dispersion staining transmission light microscopy, phase contrast transmission light microscopy, differential interference contrast transmission light microscopy, emission imaging, etc.). See, for example, Methods in Molecular Biology, 2018, *Light Microscopy Method and Protocols*, Markaki and Harz eds., Humana Press, New York, New York, ISBN-13: 978-1493983056, which is hereby incorporated by reference.

In some embodiments, the first image is a fluorescence image. In some embodiments, the first image is acquired using confocal microscopy, two-photon imaging, wide-field multiphoton microscopy, single plane illumination microscopy or light sheet fluorescence microscopy. See, for example, *Adaptive Optics, for Biological Imaging*, 2013, Kubby ed., CRC Press, Boca Raton, Florida; and *Confocal and Two-Photon Microscopy: Foundations, Applications and Advances*, 2002, Diaspro ed., Wiley Liss, New York, New York; and Handbook of Biological C or focal Microscopy, 2002, Pawley ed., Springer Science+Business Media, LLC, New York, New York, each of which is hereby incorporated by reference. In some embodiments, the first image is an immunohistochemistry (IHC) image. See, for example, Day and Davidson, 2014, "The Fluorescent Protein Revolution (In Cellular and Clinical Imaging)," CRC Press, Taylor & Francis Group, Boca Raton, Florida; "Quantitative Imaging in Cell Biology" Methods in Cell Biology 123, 2014, Wilson and Tran, eds.; Advanced Fluorescence Reporters in Chemistry and Biology II: Molecular Constructions, Polymers and Nanoparticles (Springer Series on Fluorescence), 2010, Demchenko, ed., Springer-Verlag, Berlin, Germany; Fluorescence Spectroscopy and Microscopy: Methods and Protocols (Methods in Molecular Biology) 2014th Edition, 2014, Engelborghs and Visser, eds., Human-Press, each of which is hereby incorporated by reference for their disclosure on fluorescence imaging.

In some embodiments, the first image is obtained in any suitable electronic image file format, including but not limited to JPEG/JFIF, TIFF, Exif, PDF, EPS, GIF, BMP, PNG, PPM, PGM, PBM, PNM, WebP, HDR raster formats, HEIF, BAT, BPG, DEEP, DRW, ECW, FITS, FLIF, ICO, ILBM, IMG, PAM, PCX, PGF, JPEG XR, Layered Image File Format, PLBM, SGI, SID, CDS, CPT, PSD, PSP, XCF, PDN, CGM, SVG, PostScript, PCT, WMF, EMF, SWF, XAML, and/or RAW.

In some embodiments, the first image is obtained in any suitable electronic color mode, including but not limited to grayscale, bitmap, indexed, RGB, CMYK, HSV, lab color, duotone, and/or multichannel. In some embodiments, the first image is manipulated (e.g., stitched, compressed and/or flattened). In some embodiments, the first image is a color image. In some embodiments, the first image is a monochrome image.

In some embodiments, the first image is any form of two-dimensional pixelated image. In some such embodiments, an image comprises a size denoted by n×m, where n and m refer to an edge length, in pixels. In some embodiments, an edge length, in pixels, of the first image consists of between 164 pixels and 1024 pixels. In some embodiments, an edge length of the first image is at least 50, at least 100, at least 150, at least 200, at least 250, at least 300, at least 400, at least 500, at least 600, at least 700, at least 800, at least 900, at least 1000, at least 1100, at least 1200, at least 1300, at least 1400, at least 1500, at least 1600, at least 1700, at least 1800, at least 1900, or at least 2000 pixels. In some embodiments, an edge length of the first image is no more than 2500, no more than 2000, no more than 1600, no more than 1000, no more than 800, no more than 600, no more than 400, no more than 300, or no more than 200 pixels. In some embodiments, an edge length of the first image is from 50 to 800, from 200 to 600, from 300 to 900, from 500 to 1800, or from 50 to 2500 pixels. In some embodiments, an edge length of the first image falls within another range starting no lower than 50 pixels and ending no higher than 2500 pixels. In some embodiments, n and m are the same value. In some embodiments, n and m are different values.

In some embodiments, the first image comprises at least 10,000 pixels. Referring to Block 212, in some embodiments, the first image comprises at least 100,000 pixels.

Generally, the plurality of pixels of the first image refers to the image resolution (e.g., the number of pixels in an image). In some instances, the image resolution can be determined by the dimensions of the image (e.g., n×m). Thus, in some embodiments, the plurality of pixels of the first image comprises at least 2000, at least 5000, at least 10,000, at least 20,000, at least 30,000, at least 40,000, at least 50,000, at least 100,000, at least 250,000, at least 500,000, at least 1 million, at least 1.5 million, at least 2 million, at least 3 million, or at least 5 million pixels. In some embodiments, the plurality of pixels of the first image comprises no more than 10 million, no more than 5 million, no more than 1 million, no more than 500,000, no more than 100,000, no more than 50,000, or no more than 10,000 pixels. In some embodiments, the plurality of pixels of the first image consists of from 5000 to 50,000, from 10,000 to 500,000, from 50,000 to 1 million, or from 1 million to 3 million pixels. In some embodiments, the plurality of pixels falls within another range starting no lower than 2000 pixels and ending no higher than 10 million pixels. In some embodiments, the plurality of pixels comprises any number of pixels determined using the values for edge length, in pixels, of an image disclosed herein.

In some embodiments, a pixel comprises one or more pixel values (e.g., intensity value). In some embodiments, each respective pixel in the plurality of pixels comprises one pixel intensity value, such that the plurality of pixels represents a single-channel image comprising a one-dimensional integer vector comprising the respective pixel values for each respective pixel. For example, an 8-bit single-channel image (e.g., grayscale) can comprise $2^8$ or 256 different pixel values (e.g., 0-255). In some embodiments, each respective pixel in the plurality of pixels of an image comprises a plurality of pixel values, such that the plurality of pixels represents a multi-channel image comprising a multi-dimensional integer vector, where each vector element represents a plurality of pixel values for each respective pixel. For example, a 24-bit 3-channel image (e.g., RGB color) can comprise $2^{24}$ (e.g., $2^{8\times3}$) different pixel values, where each vector element comprises 3 components, each between 0-255. In some embodiments, an n-bit image comprises up to $2^n$ different pixel values, where n is any positive integer. See, Uchida, 2013, "Image processing and recognition for biological images," Develop. Growth Differ. 55, 523-549, doi: 10.1111/dgd. 12054, which is hereby incorporated herein by reference in its entirety.

Accordingly, in some embodiments, the first image has a bit depth of at least 1, at least 2, at least 4, at least 8, at least 16, at least 24, or at least 32 bits. In some embodiments, the first image has a bit depth of no more than 48, no more than 32, no more than 24, no more than 16, no more than 8, no more than 4, or no more than 2 bits. In some embodiments, the bit depth of the first image is from 1 to 8, from 2 to 16, from 4 to 32, or from 16 to 48. In some embodiments, the first image has a bit depth that falls within another range starting no lower than 1-bit and ending no higher than 48-bit.

In some embodiments, the method comprises further modifying the first image.

In some embodiments, the modifying the first image comprises adjusting a brightness of the image, adjusting a contrast of the image, flipping the image, rotating the image, cropping the image, zooming a view of the image, panning across the image, transforming the image, resizing the image, or overlaying a grid onto the first image. In some embodiments, the modifying the first image comprises downscaling or upscaling (e.g., where the resolution is decreased or increased) the image in order to fit a target size.

Any embodiment for a first image disclosed herein is contemplated for use with respect to a second, third, and/or any subsequent image obtained for a respective subject in a corresponding one or more subjects, or any substitutions, modifications, additions, deletions, and/or combinations thereof, as will be apparent to one skilled in the art.

Additional embodiments for images and image acquisition are further described in Yi et al., "Deep learning identified pathological abnormalities predictive of graft loss in kidney transplant biopsies," Kidney International (2022) 101, 288-298; doi: 10.1016/j.kint.2021.09.028, which is hereby incorporated herein by reference in its entirety.
Trained Model.

Referring to Block 214, the method includes inputting the first image 124 into a trained model 128, where the trained model comprises a plurality (e.g., at least 10,000) of parameters 130.

In some embodiments, the plurality of parameters for the trained model comprises at least 100, at least 500, at least 1000, at least 2000, at least 5000, at least 10,000, at least 20,000, at least 50,000, at least 100,000, at least 200,000, at least 500,000, at least 1 million, at least 2 million, at least 3 million, at least 4 million or at least 5 million parameters. In some embodiments, the plurality of parameters for the trained model comprises no more than 8 million, no more than 5 million, no more than 4 million, no more than 1 million, no more than 500,000, no more than 100,000, no more than 50,000, no more than 10,000, no more than 5000, no more than 1000, or no more than 500 parameters. In some embodiments, the plurality of parameters for the trained model consists of from 100 to 5000, from 500 to 10,000, from 10,000 to 500,000, from 20,000 to 1 million, or from 1 million to 5 million parameters. In some embodiments, the plurality of parameters for the trained model falls within another range starting no lower than 100 parameters and ending no higher than 8 million parameters.

In some embodiments, the trained model comprises any of the models disclosed herein (see, e.g., the section entitled "Definitions: Models," above). For instance, in some embodiments, the trained model comprises a neural network.

In some embodiments, the neural network comprises a plurality of layers, including at least an input layer and an output layer. In some embodiments, the neural network comprises a plurality of hidden layers. Generally, as described above, hidden layers are located between input and output layers (e.g., to capture additional complexity). In some embodiments, where there is a plurality of hidden layers, each hidden layer may have the same or a different respective number of hidden neurons.

In some embodiments, each hidden neuron (e.g., in a respective hidden layer in a neural network) is associated with an activation function that performs a function on the input data (e.g., a linear or non-linear function). Generally, the purpose of the activation function is to introduce non-linearity into the data such that the neural network is trained on representations of the original data and can subsequently "fit" or generate additional representations of new (e.g., previously unseen) data. Selection of activation functions (e.g., a first and/or a second activation function) is dependent on the use case of the neural network, as certain activation functions can lead to saturation at the extreme ends of a dataset (e.g., tanh and/or sigmoid functions). For instance, in some embodiments, an activation function (e.g., a first and/or a second activation function) is selected from any of the activation functions disclosed herein and described in greater detail below.

In some embodiments, each hidden neuron is further associated with a parameter (e.g., a weight and/or a bias value) that contributes to the output of the neural network, which is determined based on the associated activation function. In some embodiments, prior to training, the hidden neuron is initialized with arbitrary parameters (e.g., randomized weights). In some alternative embodiments, prior to training, the hidden neuron is initialized with a predetermined set of parameters.

In some embodiments, the plurality of hidden neurons in a neural network (e.g., across one or more hidden layers) is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, at least 100, at least 200, at least 300, at least 400, or at least 500 neurons. In some embodiments, the plurality of hidden neurons is at least 100, at least 500, at least 800, at least 1000, at least 2000, at least 3000, at least 4000, at least 5000, at least 6000, at least 7000, at least 8000, at least 9000, at least 10,000, at least 15,000, at least 20,000, or at least 30,000 neurons. In some embodiments, the plurality of hidden neurons is no more than 30,000, no more than 20,000, no more than 15,000, no more than 10,000, no more than 9000, no more than 8000, no more than 7000, no more than 6000, no more than 5000, no more than 4000, no more than 3000, no more than 2000, no more than 1000, no more than 900, no more than 800, no more than 700, no more than 600, no more than 500, no more than 400, no more than 300, no more than 200, no more than 100, or no more than 50 neurons. In some embodiments, the plurality of hidden neurons is from 2 to 20, from 2 to 200, from 2 to 1000, from 10 to 50, from 10 to 200, from 20 to 500, from 100 to 800, from 50 to 1000, from 500 to 2000, from 1000 to 5000, from 5000 to 10,000, from 10,000 to 15,000, from 15,000 to 20,000, or from 20,000 to 30,000 neurons. In some embodiments, the plurality of hidden neurons falls within another range starting no lower than 2 neurons and ending no higher than 30,000 neurons.

In some embodiments, the neural network consists of from 1 to 50 hidden layers. In some embodiments, the neural network consists of from 1 to 20 hidden layers. In some embodiments, the neural network comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, or at least 100 hidden layers. In some embodiments, the neural network comprises no more than 100, no more than 90, no more than 80, no more than 70, no more than 60, no more than 50, no more than 40, no more than 30, no more than 20, no more than 10, no more than 9, no more than 8, no more than 7, no more than 6, or no more than 5 hidden layers. In some embodiments, the neural network consists of from 1 to 5, from 1 to 10, from 1 to 20, from 10 to 50, from 2 to 80, from 5 to 100, from 10 to 100, from 50 to 100, or from 3 to 30 hidden layers. In some embodiments, the neural network comprises a plurality of hidden layers that falls within another range starting no lower than 1 layer and ending no higher than 100 layers.

In some embodiments, the neural network comprises a shallow neural network. A shallow neural network refers to a neural network with a small number of hidden layers. In some embodiments, such neural network architectures improve the efficiency of neural network training and performance and conserve computational power due to the reduced number of layers involved. In some embodiments, the neural network comprises only one hidden layer.

In some embodiments, the neural network comprises a plurality of parameters (e.g., weights and/or hyperparameters). In some embodiments, each respective layer in the neural network comprises a respective corresponding plurality of parameters. In some such embodiments, the respective corresponding plurality of parameters for a respective layer is a subset of the plurality of parameters associated with the neural network.

In some embodiments, the plurality of parameters for a respective layer in a plurality of layers in the trained neural network comprises at least 100, at least 500, at least 1000, at least 2000, at least 5000, at least 10,000, at least 20,000, at least 50,000, at least 100,000, at least 200,000, at least 500,000, at least 1 million, at least 2 million, or at least 3 million parameters. In some embodiments, the plurality of parameters for a respective layer in a plurality of layers in the trained neural network comprises no more than 5 million, no more than 4 million, no more than 1 million, no more than 500,000, no more than 100,000, no more than 50,000, no more than 10,000, no more than 5000, or no more than 1000 parameters. In some embodiments, the plurality of parameters for a respective layer in a plurality of layers in the trained neural network consists of from 100 to 1000, from 1000 to 10,000, from 2000 and 200,000, from 8000 and 1 million, or from 30,000 and 3 million parameters. In some embodiments, the plurality of parameters for a respective layer in a plurality of layers in the trained neural network falls within another range starting no lower than 100 parameters and ending no higher than 5 million parameters.

As described above, in some embodiments, one or more layers in the trained neural network is associated with one or more activation functions. In some embodiments, a respective activation function is tanh, sigmoid, softmax, Gaussian, Boltzmann-weighted averaging, absolute value, linear, rectified linear unit (ReLU), bounded rectified linear, soft rectified linear, parameterized rectified linear, average, max, min, sign, square, square root, multiquadric, inverse quadratic, inverse multiquadric, polyharmonic spline, swish, mish, Gaussian error linear unit (GeLU), scaled exponential linear unit (SELU), or thin plate spline.

Referring to Block 216, in some embodiments, the trained model comprises a convolutional neural network comprising one or more filters, a respective kernel size, and a respective stride.

For instance, in some embodiments, the trained model is a neural network that comprises a plurality of convolutional layers. In some embodiments, the model comprises at least 2, at least 3, at least 4, at least 5, at least 6, at least 7, at least 8, at least 9, at least 10, or at least 20 convolutional layers. In some embodiments, the model comprises no more than 50, no more than 20, no more than 10, or no more than 5 convolutional layers. In some embodiments, the model comprises from 1 to 5, from 2 to 10, from 5 to 20, or from 10 to 40 convolutional layers. In some embodiments, the model comprises a plurality of convolutional layers that falls within another range starting no lower than 2 convolutional layers and ending no higher than 50 convolutional layers.

In some embodiments, a convolutional layer in the plurality of convolutional layers comprises a set of learnable filters (also termed kernels). Each filter has a fixed N-dimensional size that is convolved (stepped at a predetermined step rate) across the depth, height and/or width of the input space of the convolutional layer, computing a function (e.g., a dot product) between entries (weights, or more generally parameters) of the filter and the input thereby creating a multi-dimensional activation map of that filter. In some embodiments, the filter stride (e.g., step rate) is one element, two elements, three elements, four elements, five elements, six elements, seven elements, eight elements, nine elements, ten elements, or more than ten elements of the input space.

This stepping (convolving) is repeated until the filter has sampled the entire input space in accordance with the stride. In some embodiments, the border of the input space is padded to control the spatial volume of the output space produced by the convolutional layer. In typical embodiments, each of the filters of the convolutional layer canvas the entire input space in this manner thereby forming a corresponding activation map. The collection of activation maps from the filters of the convolutional layer collectively form the output space of one convolutional layer, and thereby serves as the input of a subsequent convolutional layer. Every entry in the output volume can thus also be interpreted as an output of a single neuron (or a set of neurons) that looks at a small region in the input space to the convolutional layer and shares parameters with neurons in the same activation map. Accordingly, in some embodiments, a convolutional layer in the plurality of convolutional layers has a plurality of filters and each filter in the plurality of filters convolves across the input space.

Each layer in the plurality of convolutional layers is associated with a different set of weights, or more generally a different set of parameters. With more particularity, each layer in the plurality of convolutional layers includes a plurality of filters and each filter comprises an independent plurality of parameters (e.g., weights). In some embodiments some or all such parameters (and, optionally, biases) of every filter in a given convolutional layer may be tied together, e.g., constrained to be identical.

In some embodiments, the convolutional neural network comprises an input layer that, responsive to a respective input (e.g., the first image), feeds a first plurality of values into the initial convolutional layer as a first function of values (e.g., pixel values) in the respective input, where the first function is optionally computed using a system 100.

In some embodiments, each respective convolutional layer, other than a final convolutional layer, feeds intermediate values, as a respective second function of (i) the different set of parameters (e.g., weights) associated with the respective convolutional layer and (ii) input values received by the respective convolutional layer, into another convolutional layer in the plurality of convolutional layers. For instance, in some embodiments, each respective filter of the respective convolutional layer canvasses the input space to the convolutional layer in accordance with the characteristic stride of the convolutional layer and at each respective filter position, takes the mathematical function of the filter parameters (e.g., weights) of the respective filter and the values of the input space at the respect filter position thereby producing a calculated point (or a set of points) on the activation layer corresponding to the respective filter position. The activation layers of the filters of the respective convolutional layer collectively represent the intermediate values of the respective convolutional layer.

In some embodiments, the respective stride (e.g., a number of elements, such as pixels, by which a filter moves across the first image) is at least 1, at least 5, at least 10, at least 20, at least 50, at least 100, at least 150, at least 200, at least 250, at least 300, or at least 500. In some embodiments, the stride is no more than 1000, no more than 500, no more than 300, no more than 200, no more than 100, no more than 50, or no more than 10. In some embodiments, the stride is from 10 to 100, from 1 to 30, from 50 to 500, from 100 to 200, or from 300 to 1000. In some embodiments, the stride falls within another range starting no lower than 1 and ending no higher than 1000. In some embodiments, a first respective layer has the same or different stride as a second respective layer.

Generally, convolutional filters (e.g., kernels) comprise a corresponding height and width. In typical embodiments, a respective filter is smaller than the input image to the corresponding convolutional layer which the respective filter is used to convolve. In some embodiments, the value for a kernel size indicates the edge length of the kernel (e.g., 1×1, 2×2, etc.). In some embodiments, a respective size for a kernel is a matrix (n×n) of pixels. In some embodiments, n is at least 1, at least 5, at least 10, at least 20, at least 50, at least 100, at least 150, at least 200, at least 250, at least 300, at least 500, or at least 1000. In some embodiments, n is no more than 2000, no more than 1000, no more than 500, no more than 300, no more than 200, no more than 100, no more than 50, or no more than 10. In some embodiments, n is from 10 to 100, from 1 to 30, from 50 to 500, from 100 to 1000, from 300 to 400, or from 100 to 300. In some embodiments, n falls within another range starting no lower than 1 and ending no higher than 2000.

In some embodiments, the trained model comprises a plurality of component models.

More particularly, referring to Block 218, in some embodiments, the trained model comprises a plurality of component models, comprising: a compartment detection model trained to identify one or more first corresponding objects in the first image that fall within a first morphological class in the plurality of morphological classes, an inflammation detection model trained to identify one or more second corresponding objects in the first image that fall within a second morphological class in the plurality of morphological classes, and a tissue segmentation model trained to identity one or more third corresponding objects in the first image that fall within a third morphological class in the plurality of morphological classes.

For instance, in some embodiments, the compartment detection model is trained to identify a first tissue compartment class consisting of tubules and glomeruli, the inflammation detection model is trained to identify an inflammatory marker class consisting of MNLs, and the tissue segmentation model is trained to identify a second tissue compartment class consisting of interstitium.

Referring to Block 220, in some embodiments, each respective component model in the plurality of component models is selected from the group consisting of a pixel-level prediction algorithm and an instance-level object detection algorithm.

For instance, in some implementations, each of the compartment detection model and the inflammation detection model is an instance-level object detection algorithm (e.g., Mask Region-based Convolutional Neural Network (MR-CNN)), and the tissue segmentation model is a pixel-level prediction algorithm (U-Net).

As described below in Example 1, a Mask R-CNN model first extracts feature maps from input images using a convolutional backbone structure and generates region proposals for given objects through Region Proposal Network (RPN). These proposed regions are later passed through another neural network to generate multi-categorical classes, bounding boxes and masks for objects. Accordingly, in some embodiments, a respective component model further comprises at least a first convolutional neural network for generating region proposals for one or more objects corresponding to a respective morphological class, and a second neural network for generating multi-categorical classes, bounding boxes, and masks for proposed objects.

As further described below in Example 1, a U-Net model makes predictions for pixels instead of object instances in input images. It has a symmetrical "U" shape architecture consisting of an encoder which extracts features from input images using convolution blocks and a decoder which expands contracted vectors back to segmentation maps at the input size. In some implementations, the number of blocks in the encoder step is the same as the number of blocks in decoder step. For instance, in the exemplary method described in Example 1, the segmentation model was constructed using 3 down-sampling layers and 3 up-sampling layers and the first layer contained 32 feature maps.

In some embodiments, a respective component model in the plurality of component models is any algorithm or model, including any neural network, disclosed herein (see, e.g., the section entitled "Definitions: Models," above), or any substitutions, modifications, additions, deletions, and/or combinations thereof, as will be apparent to one skilled in the art. For instance, in some embodiments, a respective component model in the plurality of component models comprises a multilayer neural network, a deep convolutional neural network, a visual geometry convolutional neural network, a residual neural network, a residual convolutional neural network, and/or a combination thereof.

Additional embodiments for model architectures are further described in Yi et al., "Deep learning identified pathological abnormalities predictive of graft loss in kidney transplant biopsies," Kidney International (2022) 101, 288-298; doi: 10.1016/j.kint.2021.09.028, which is hereby incorporated herein by reference in its entirety.

Identifying Objects

Referring to Block 222, the method further includes identifying, as output from the trained model 128, for each respective morphological class 132 in the at least the first subset of morphological classes, a corresponding one or more objects 134 that fall within the respective morphological class, where the first subset of morphological classes includes the first tissue compartment class or the inflammatory mediator class.

In some embodiments, the identifying the one or more objects comprises obtaining, for each respective morphological class in the at least the first subset of morphological classes, a corresponding calculated indication that localizes the one or more objects in the corresponding image that fall within the respective morphological class.

As used herein, an object that falls within a respective morphological class can be considered as belonging to that morphological class. For instance, when the morphological class is an inflammatory marker class, an object that falls within the inflammatory marker class is an inflammatory marker (e.g., MNLs) that can be visualized or otherwise discriminated within the image. As another example, when the morphological class is a tissue compartment class, an object that falls within the tissue compartment class is a tissue structure (e.g., tubules and/or glomeruli) and/or a tissue differentiating feature (e.g., interstitium) that can be visualized or otherwise discriminated within the image.

In some embodiments, the first subset of morphological classes includes at least the first tissue compartment class, the inflammatory mediator class, and/or a second tissue compartment class. Accordingly, in some embodiments, the identifying identifies objects that fall within one or more of first tissue compartment class, the inflammatory mediator class, and the second tissue compartment class (e.g., tubules, glomeruli, interstitium, and/or MNLs).

In some embodiments, the first subset of morphological classes includes each respective morphological class in the plurality of morphological classes, and the identifying identifies objects that fall within each respective morphological class in the plurality of morphological classes (e.g., tubules, glomeruli, interstitium, and MNLs).

In some embodiments, the identifying identifies at least a pixel that corresponds to an object that falls within a respective morphological class.

In some embodiments, the identifying identifies at least a portion of the image that corresponds to an object that falls within a respective morphological class.

In some embodiments, the identifying generates a mask that localizes, within the image, the position of an object that falls within a respective morphological class.

In some embodiments, the identifying identifies a region of interest (ROI) that contains at least a threshold amount (e.g., a proportion and/or density) of objects, within a specified area, that fall within a respective morphological class (e.g., where the first image is segmented into ROIs identified as corresponding to a first morphological class, a second morphological class, etc.).

Identification of objects, masks, and/or regions of interest are illustrated, for example, in FIGS. 4A-D with reference to Example 1 below.

Accordingly, in some embodiments, the model generates, as output, the calculated indications of the corresponding one or more objects represented as one or more pixels (e.g., masks) overlaid onto the first image. In some embodiments, the model generates, as output, the calculated indications of the corresponding one or more objects represented as one or more sets of coordinates that indicate the locations of the one or more objects within the first image.

In some embodiments, the trained model comprises a plurality of component models, where each respective component model in the plurality of component models is trained to identify one or more objects corresponding to a different respective morphological class in the at least the first subset of morphological classes. In some such embodiments, the trained model provides, as output, a respective output corresponding to the respective morphological class for each respective component model in the plurality of component models. In some embodiments, the trained model comprises a plurality of component models, and the trained model provides a single output including the calculated indications for each of the morphological classes in the at least the first subset of morphological classes.

In some embodiments, the trained model is a multi-class model that provides, as output, a plurality of outputs, where each respective output includes the calculated indications for a respective morphological class in the at least the first subset of morphological classes.

In some embodiments, the trained model is a multi-class model that provides, as output, a single output including the calculated indications for each of the morphological classes in the at least the first subset of morphological classes.

In some embodiments, the method further includes combining a plurality of calculated indications for a respective one or more objects corresponding to a respective one or more morphological classes (e.g., overlaying masks into a single representative image and/or combining sets of coordinates into a combined dataset of coordinates).

Additional embodiments for obtaining object indications are further described in Yi et al., "Deep learning identified pathological abnormalities predictive of graft loss in kidney transplant biopsies," Kidney International (2022) 101, 288-298; doi: 10.1016/j.kint.2021.09.028, which is hereby incorporated herein by reference in its entirety.

Digital Features.

Referring to Block 224, the method further comprises generating, for each respective morphological class 132 in the at least the first subset of morphological classes, a corresponding plurality of digital features 136 comprising (i) a first corresponding subset of individual feature scores 138, where each respective individual feature score is obtained using the corresponding one or more objects 134 for the respective morphological class, and (ii) a second corresponding subset of composite feature scores 140, where each respective composite feature score is obtained by combining two or more individual feature scores 138 in the first corresponding subset of individual feature scores.

Thus, in some embodiments, the method comprises generating a digital feature dataset 136 including all of the digital features across all of the morphological classes in the at least the first subset of morphological classes.

In some embodiments, the digital feature dataset includes one or more individual feature scores, composite feature scores, and/or composite class scores.

In some embodiments, a respective digital feature can represent one or more objects, one or more regions of interest within the first image (e.g., a portion of a slide or of the first image thereof), one or more images (e.g., of all or a portion of a slide or of the first image thereof), and/or one or more substrates (e.g., a whole-slide image).

In some embodiments, a respective individual feature score corresponds to a respective morphological class in the plurality of morphological classes. In some embodiments, a respective individual feature score corresponds to a respective morphological class in the at least the first subset of morphological classes.

In some embodiments, the obtaining each respective individual feature score using the corresponding one or more objects for a respective morphological class is performed by determining a number (e.g., a count) of objects for the respective morphological class.

In some embodiments, the obtaining each respective individual feature score using the corresponding one or more objects for a respective morphological class is performed by determining a number of objects, within a specified area within the first image (e.g., a proportion, density, and/or area estimation), that fall within the respective morphological class.

In some embodiments, the specified area within the first image is a region of the first image "windowed" by a convolutional filter, a region of interest (ROI), the entirety of the first image, a portion of the first image, and/or the entirety of the substrate in a whole-slide image.

For instance, referring to Block 226, a respective individual feature score in the first corresponding subset of individual feature scores is selected from the group consisting of a size of an area of the substrate (e.g., a size of a convolutional filter, a size of an ROI, a size of the first image, a size of a portion of the first image (e.g., an image tile), and/or a size of a whole-slide image for the substrate), a number of objects in a corresponding plurality of objects for a respective morphological class within an area of the substrate (e.g., a number of tubules, glomeruli, and/or MNLs within a region of the first image "windowed" by a convolutional filter, an ROI, the first image, a portion of the first image, and/or a whole-slide image for the substrate), and a percentage of a corresponding plurality of objects for a respective morphological class over an area of the substrate (e.g., a percentage of tubules, glomeruli, MNLs, or interstitial area over a region of the first image "windowed" by a convolutional filter, an ROI, the first image, a portion of the first image, and/or a whole-slide image for the substrate). As described above, an object in the one or more objects can be a pixel, an object (e.g., a segmented tissue compartment or morphological structure), and/or a region of interest corresponding to the respective morphological class. See, e.g., the section entitled "Identifying objects," above.

In some embodiments, the digital feature dataset includes one or more digital features that indicate a respective condition (e.g., abnormal or normal) for a corresponding one or more objects, one or more regions of interest within an image (e.g., a portion of a slide or of an image thereof), one or more images (e.g., of all or a portion of a slide or of an image thereof), and/or one or more substrates (e.g., a whole-slide image) corresponding to a respective morphological class in all or the first subset of morphological classes.

For instance, referring to Block 228, in some embodiments, the generating the corresponding plurality of digital features for a respective morphological class further comprises (i) identifying, in the first image, a first region of interest as having a first condition for the respective morphological class, and (ii) assigning the first condition to one or more individual feature scores, in the first corresponding subset of individual feature scores. In some embodiments, the first condition is selected from the group consisting of abnormal and normal. In some embodiments, the method further includes classifying the first region of interest as interstitial or inflammatory.

An example embodiment of determining normal and abnormal features is described below in Example 1. In some such embodiments, the trained model or a component model thereof can identify one or more regions of interest as tissue compartment or inflammatory marker and/or as normal or abnormal. Accordingly, as illustrated in Example 1, the method includes obtaining two masks highlighting an abnormal interstitium area and an abnormal MNL infiltration area, respectively. The method further includes defining abnormal digital features in the digital feature dataset (e.g., abnormal interstitial space, abnormal tubules, and/or MNL, infiltration) over a specified area within the first image (e.g., a region of the first image "windowed" by a convolutional filter, an ROI, the first image, a portion of the first image, and/or the entire substrate), based on the identified regions of interest.

More particularly, referring to Block 230, the identifying the first region of interest as having the first condition (e.g., normal or abnormal) comprises determining a corresponding set of object population statistics for the first region of interest, where each respective object population statistic in the corresponding set of object population statistics is obtained using the corresponding one or more objects for the respective morphological class, and, when each respective object population statistic in the set of object population statistics satisfies a corresponding threshold criterion, classifying the first region of interest as having the first condition.

In some embodiments, a respective object population statistic is a density or a sparsity of one or more objects for the respective morphological class.

For example, in some embodiments, the respective morphological class is a tissue compartment class, and the first region of interest is classified as an "interstitial region of interest" when the one or more objects for the first region of interest, identified by the trained model, indicates a wide interstitial space but a narrow space of background noise and other objects in regions predominantly occupied by tubules. Moreover, in some such embodiments, the first region of interest is classified as an "abnormal interstitial region of interest" when:

$$\text{Sparsity}(I) > 0.35, \text{ Density}(O) < 0.2, \text{ and Density}(B) < 0.2, \text{ where}$$

$$\text{Sparsity}(I) = \frac{\text{area}(InterstitialSpace)}{\text{area}(InterstitialSpace) + \text{area}(\text{Tubule})},$$

$$\text{Density}(O) = \frac{\text{area}(Glomeruli) + \text{area}(OtherGroups)}{\text{area}(RegionofInterest)}, \text{ and}$$

$$\text{Density}(B) = \frac{\text{area}(\text{Background})}{\text{area}(RegionOfInterest)}.$$

In another example, the respective morphological class is an inflammatory marker class, and the first region of interest is classified as an "inflammatory region of interest" when the one or more objects for the first region of interest, identified by the trained model, indicates enrichment of MNLs. In particular, the first region of interest is classified as an "abnormal inflammatory region of interest" when:

$$\text{Density}(MNL) > 43, \text{ where}$$

$$\text{Density}(MNL) = \frac{N(MNL)}{\text{area}(RegionOfInterest)}.$$

In some embodiments, normal and/or abnormal classifications can be determined for individual feature scores, composite feature scores, and/or composite class scores at the intra- or inter-class level.

For example, in some embodiments, an abnormal individual feature score for the interstitium is an estimate of overall percentage of interstitial space over a specified area of the substrate (e.g., WSI area), where $$\text{Abnormal Interstitial Area Percentage} =$$

$$\frac{\text{area}(\text{Interstitial Space within Interstitial } ROI)}{\text{area}(WSI)}.$$

In some embodiments, an abnormal individual feature score for tissue compartments (e.g., tubules) is a summary of a number of abnormal tubules per specified area of the substrate or the first image thereof (e.g., 1000×1000 pixels or WSI), where $$\text{Abnormal Interstitial Area Percentage} = \frac{N(\text{Abnormal Tubules})}{\text{area}(WSI)} \times 10^6.$$

In some embodiments, an abnormal individual feature score for inflammation (e.g., MNLs) is an estimated proportion of an MNL-enriched area over a specified area of the substrate (e.g., WSI area), where $$\text{MNL-enriched Area Percentage} = \frac{\text{area}(\text{Inflammatory } ROI)}{\text{area}(WSI)},$$

In some embodiments, an abnormal individual feature score for inflammation is an average number of MNLs in an inflammatory ROI per specified area of the substrate or the first image thereof (e.g., 1000×1000 pixels or WSI), where $$\text{MNL Density}(infR) = \text{Average } N(MNL) \text{ weighted across Inflammatory ROIs.}$$

In some embodiments, for each respective morphological class in the at least the first subset of morphological classes, the respective plurality of digital features, including individual feature scores, are defined in consideration of two aspects: i) how widespread a given abnormal feature is over the area of a slide (such as Abnormal Interstitial Area Percentage and MNL-enriched Area Percentage); and ii) how dense a given abnormal object is per unit area (such as Abnormal Tubules Density and MNL Density (infR)).

Accordingly, referring to Block 232, a respective individual feature score in the first corresponding subset of individual feature scores is selected from the group consisting of an abnormal interstitial area percentage (e.g., a proportion of total abnormal interstitium area over the whole-slide image, ROI, and/or all or a portion of the first image), a standardized abnormal tubule density, a mononuclear leukocyte-enriched area percentage (e.g., a proportion of the MNL infiltration area over the whole-slide image, ROI, and/or all or a portion of the first image), and a standardized mononuclear leukocyte density.

In some embodiments, for each respective morphological class in the at least a first subset of morphological classes, the method further includes obtaining composite feature scores by combining two or more individual feature scores in the first corresponding subset of individual feature scores.

Referring to Block 234, in some embodiments, a respective composite feature score in the second corresponding subset of composite feature scores is selected from the group consisting of an interstitial and tubule abnormality score (ITAS) obtained by combining the abnormal interstitial area percentage and the standardized abnormal tubule density, and a mononuclear leukocyte infiltration score (MNL-IS) obtained by combining the mononuclear leukocyte-enriched area percentage and the standardized mononuclear leukocyte density.

In some such embodiments, MNL-IS and ITAS are obtained using the following formulas:

$$\text{MNL-IS} = \max(MNL \text{ enriched Area Percentage} \times \log_2(\text{Density}(infR)), 0),$$

$$\text{and}$$

$$\text{ITAS} = \max(\text{Abnormal Interstitial Area Percentage} \times$$

$$\log_2(\text{Abnormal Tubules Density}), 0).$$

In some embodiments, to obtain composite feature scores, individual feature scores are first rescaled through $\log_2$ transformation to correct for skewed distributions of density features.

Advantageously, and without being limited to any one theory of operation, by multiplying the above-referenced coverage-based individual feature scores (area %) by density-based individual feature scores, the composite feature scores Interstitial and Tubular Abnormality Score (ITAS)

and MNL infiltration Score (MNL-IS) better approximate the relative amount of IFTA (Interstitial Fibrosis and Tubular Atrophy) and MNLs. Additionally, in some embodiments, the max(x,0) function shown in the above formulas for MNL-IS and ITAS serves as a gate function to ensure non-negative values.

In some embodiments, the corresponding plurality of digital features is obtained for one or more respective morphological classes in the at least the first subset of morphological classes (e.g., tissue, including tubules, glomeruli, and/or interstitium, and/or inflammation, including MNLs).

In some embodiments, the corresponding plurality of digital features is obtained for each morphological class in the plurality of morphological classes.

In some embodiments, the method further comprises generating a composite class score by combining at least a first composite feature score for a corresponding first morphological class and a second composite feature score for a corresponding second morphological class different from the first morphological class.

For instance, in some such embodiments, a Composite Damage Score (CDS) is obtained by integrating the ITAS and MNL Infiltration Score.

In some embodiments, the CDS is obtained using: CDS=MNL-IS+ITAS.

In some embodiments, the CDS provides an estimation of overall graft damage. In some embodiments, the CDS provides an approximation of interstitial IFTA.

In some embodiments, a respective composite class score is obtained by combining digital features for at least 2, at least 3, at least 4, or at least 5 morphological classes in the at least the first subset of morphological class.

In some embodiments, the digital feature dataset includes at least 1, at least 2, at least 3, at least 4, or at least 5 composite class scores.

In some embodiments, a plurality of images of one or more kidney graft biopsies were obtained for a respective subject (e.g., where patients had multiple segments per slide or re-scanned slides at the time of biopsy, resulting in multiple corresponding images per slide). In some such embodiments, where the plurality of images comprises multiple segments per slide, the method further includes estimating individual feature scores in the plurality of digital features within each segment, weighting each respective individual feature score by relative size of segment using $$\frac{\text{area of segment}(i)}{\text{total area of all segments}},$$

and summing for each type of individual feature score, the plurality of individual feature scores across multiple segments. In some embodiments, where the type of individual feature score is a count of glomeruli, the method includes summing the count of glomeruli across multiple segments without weighting. Accordingly, in some such embodiments, the method includes weighting individual feature scores extracted from large segments more heavily than those from small segments.

In some embodiments, where the plurality of images comprises re-scanned slides, the method further includes estimating individual feature scores in the plurality of digital features within each scan, weighting each respective individual feature score by relative size of slide, and summing, for each type of individual feature score, the plurality of individual feature scores across multiple scans.

Additional embodiments for digital features are further described in Yi et al., "Deep learning identified pathological abnormalities predictive of graft loss in kidney transplant biopsies," Kidney International (2022) 101, 288-298; doi: 10.1016/j.kint.2021.09.028, which is hereby incorporated herein by reference in its entirety.

Determining Risk.

Referring to Block 236, the method further includes comparing, for each respective morphological class 132 in the at least the first subset of morphological classes, a respective digital feature 136 in the corresponding plurality of digital features for the respective morphological class to a reference criterion 144, thereby determining the risk of kidney graft failure for the subject.

In some embodiments, the digital feature used in the comparing is an individual feature score and/or a composite feature score.

In some embodiments, the comparing comprises comparing a digital feature for one or more respective morphological classes in the at least the first subset of morphological classes. In some embodiments, the comparing comprises comparing a digital feature for each morphological class in the at least the first subset of morphological classes. In some embodiments, the comparing comprises comparing a digital feature for each morphological class in the plurality of morphological classes.

Referring to Block 238, the method further includes generating a composite class score by combining at least a first composite feature score (e.g., CDS) for a corresponding first morphological class and a second composite feature score for a corresponding second morphological class different from the first morphological class, where the comparing, for each respective morphological class in the at least the first subset of morphological classes, a respective digital feature in the corresponding plurality of digital features for the respective morphological class to a reference criterion further comprises comparing the composite class score (e.g., CDS) to the reference criterion.

In some embodiments, the comparing comprises comparing a plurality of digital features in the digital feature dataset to the reference criterion. In some embodiments, the comparing comprises comparing one or more digital features in the digital feature dataset to one or more reference criteria in a plurality of reference criteria.

In some embodiments, the comparing comprises comparing a plurality of digital features for all or a portion of the first image (e.g., an object, an area of the image windowed by a convolutional filter, a region of interest, an image tile, and/or a whole-slide image for the first image) to the one or more reference criteria.

Referring to Block 240, in some embodiments, the kidney graft failure is death-censored graft loss, acute cellular rejection, or decline of estimated glomerular filtration rate (eGFR).

In some embodiments, the reference criterion is a reference measure of kidney damage (e.g., a Banff score, a decline in eGFR rate, an acute cellular rejection, Kidney Donor Profile Index (KDPI), death-censored graft loss (DCGL), and/or Chronic Allograft Damage Index (CADI)). In some embodiments, the reference criterion is a threshold for risk stratification.

For instance, in some embodiments, referring to Block 244, the method further comprises determining a correlation between the respective digital feature and a reference measure of kidney damage (e.g., a Banff score, a decline in eGFR rate, an acute cellular rejection, Kidney Donor Profile Index (KDPI), death-censored graft loss (DCGL), and/or Chronic Allograft Damage Index (CADI)).

In some embodiments, the reference measure of kidney damage is graded by expert visual-assessment (e.g., by a clinician, pathologist, and/or medical practitioner) from one or more histologic stains.

In some embodiments, the reference measure of kidney damage is a Banff score selected from the group consisting of interstitial fibrosis (ci), tubular atrophy (ct), total inflammation (ti), interstitial inflammation (i), tubulitis (t), glomerulitis (g), mesangial matrix increase (mm), transplant glomerulopathy (cg), interstitial fibrosis and tubular atrophy (i-IFTA), intimal arteritis (v), arterial fibrous intimal thickening (cv), hyaline arteriolar thickening (ah), calcineurin inhibitor-related arteriolopathy (aah), and/or peritubular capillaritis (ptc and/or C4d). In some embodiments, the reference measure of kidney damage is a composite Banff score including one or more of any of the disclosed Banff scores (e.g., i+t), or any substitutions, modifications, additions, deletions, and/or combinations thereof, as will be apparent to one skilled in the art.

In some embodiments, the reference measure of kidney damage is a post-transplant factor, such as a rate of decline of estimated glomerular filtration rate (eGFR).

In some embodiments, the reference measure of kidney damage is the Kidney Donor Profile Index (KDPI), a composite demographic and clinical factor that is validated for deceased donors.

In some embodiments, the reference measure of kidney damage is death-censored graft loss (DCGL).

In some embodiments, the reference measure of kidney damage is a delayed graft function (e.g., more than 3 months post-transplantation) and/or an early graft damage (e.g., no more than 3 months post-transplantation). In some such embodiments, the reference measure of kidney damage is measured by the Chronic Allograft Damage Index (CADI). In some embodiments, a CADI score indicates damage when the CADI score satisfies a respective CADI threshold value.

In some embodiments, the kidney graft biopsy is obtained pre-implantation, and the CADI score indicates damage when the CADI score satisfies a first CADI threshold value. In some embodiments, the kidney graft biopsy is obtained post-transplantation, and the CADI score indicates damage when the CADI score satisfies a second CADI threshold value.

For example, in some such embodiments, the first CADI threshold value is 2, such that a CADI score>2 indicates kidney damage and a CADI score≤2 indicates no damage for kidney graft biopsies obtained pre-implantation (e.g., at baseline). In some embodiments, the second CADI threshold value is 4, such that a CADI score≥4 indicates kidney damage and a CADI score<4 indicates no damage for kidney graft biopsies obtained post-transplantation (e.g., 12 months post-transplantation).

Referring to Block 242, in some embodiments, the method further comprises using the respective digital feature to categorize the first image into a risk category, based on the comparison with the reference criterion, where the risk category is one of three nonoverlapping stratified risk categories selected from the group consisting of low risk, medium (e.g., intermediate) risk, or high risk.

In some embodiments, the reference criterion is a threshold for risk stratification. In some such embodiments, the reference criterion is determined by stratifying a severity of one or more reference measures of kidney damage (e.g., a Banff score, a decline in eGFR rate, an acute cellular rejection, Kidney Donor Profile Index (KDPI), death-censored graft loss (DCGL), and/or Chronic Allograft Damage Index (CADI)) in at least a first reference cohort of reference subjects.

In some embodiments, the stratifying the severity of one or more reference measures of kidney damage includes (i) determining a respective percentile for low risk, medium risk, and high risk, based on the one or more reference measures of kidney damage, within the first reference cohort, and (ii), for each risk category in the plurality of risk categories, applying the respective percentile to the respective digital feature, in a plurality of digital features, across a second reference cohort. In some embodiments, the first reference cohort and the second reference cohort are the same. In some embodiments, the first reference cohort and the second reference cohort are different.

In some embodiments, the threshold for risk stratification is determined based on the time of kidney graft biopsy acquisition. For instance, in some embodiments, a first threshold for risk stratification is applied for a first kidney graft biopsy, and a second threshold for risk stratification is applied for a second kidney graft biopsy, where the first kidney graft biopsy and the second kidney graft biopsy are obtained at different times. In some embodiments, the first kidney graft biopsy is a pre-implantation biopsy, and the second kidney graft biopsy is a post-transplantation biopsy.

An example implementation is described below in Example 1. For instance, three non-overlapping risk categories were stratified by composite feature score ITAS, including high (ITAS>0.6), intermediate (0.1≤ITAS≤0.6), and low (ITAS<0.1) risk. The threshold of high risk ITAS in baseline kidney graft biopsies was determined according to the percentile of baseline ci+ct>1 in a reference cohort. The threshold for low risk was added to identify healthy donor kidneys with zero or extremely low ITAS (<0.1). In another example, risk categories were stratified by composite class score CDS in order to summarize abnormalities detected in interstitium, tubules, and inflammation for graft loss risk stratification in 12-month post-transplantation kidney graft biopsies. The threshold of 12-month CDS (>1.5) was determined according to the percentile of 12-month CADI≥4 in the GoCAR cohort, as 1-year CADI≥4 is considered a surrogate for high risk of graft loss in patients who received transplants.

In some embodiments, the reference measure of kidney damage is 24-month CADI, and the severity of the reference measure is classified as high when 24-month CADI>2.

In some embodiments, the reference measure of kidney damage is KDPI, and the severity of the reference measure is classified as high when KDPI>85%, intermediate when 20%<KDPI≤85%, and low when KDPI≤20% in a deceased-donor population.

In some embodiments, the reference measure of kidney damage is 3-month to 12-month eGFR decline, and the severity of the reference measure is classified as high when the eGFR decline is >30%. In some embodiments, the reference measure of kidney damage is 6-month to 24-month eGFR decline, and the severity of the reference measure is classified as high when the eGFR decline is >30%.

In some embodiments, the reference measure of kidney damage is acute cellular rejection, and the severity of the reference measure is classified as high when acute cellular rejection (including or excluding borderline cases) is present at 12 months.

In some embodiments, the comparing the respective digital feature to the reference criterion comprises adjusting the respective digital feature by one or more confounders adjustment factors selected from the group consisting of recipient age, sex, race, donor age, number of transplants, kidney diseases, living or deceased donor, human leukocyte antigen mismatch, cold ischemia time (CIT), induction type, baseline donor-specific antibodies, and delayed graft function.

Referring to Block 246, in some embodiments, the first image is of a pre-implantation kidney graft biopsy, and the risk of kidney graft failure is predictive for a period of no more than 1 year post-transplantation. In some such embodiments, the respective digital feature is ITAS.

Referring to Block 248, in some embodiments, the first image is of a post-transplantation kidney graft biopsy, and the risk of kidney graft failure is predictive for a period of 1 year or more post-transplantation. In some such embodiments, the respective digital feature is CDS.

Additional embodiments for determining risk of kidney graft failure are further described in Yi et al., "Deep learning identified pathological abnormalities predictive of graft loss in kidney transplant biopsies," Kidney International (2022) 101, 288-298; doi: 10.1016/j.kint.2021.09.028, which is hereby incorporated herein by reference in its entirety.
Model Training.

Referring to Block 250, in some embodiments, the trained model is obtained by a procedure comprising (a) obtaining, in electronic format, a training dataset comprising, for each respective training sample in a plurality of training samples, (i) a corresponding training image of a training kidney graft biopsy on a substrate, where the corresponding training image represents at least a second subset of morphological classes in a plurality of morphological classes comprising at least the first tissue compartment class and the inflammatory mediator class, and where the corresponding training image comprises a plurality (e.g., at least 10,000) of pixels. In some embodiments, the training dataset further comprises, for each respective training sample in the plurality of training samples, (ii) a corresponding measured indication that localizes one or more objects in the corresponding training image that fall within each respective morphological class in the at least the second subset of morphological classes.

For each respective training sample in a first subset of the plurality of training samples, the corresponding training image is of a kidney graft biopsy obtained pre-implantation, for each respective training sample in a second subset of the plurality of training samples, the corresponding training image is of a kidney graft biopsy obtained post-transplantation, and the plurality of training samples collectively represents each respective morphological class in the plurality of morphological classes.

The procedure further comprises (b) training an untrained or partially trained model comprising a plurality (e.g., at least 10,000) of parameters by a process comprising, for each corresponding training image of each corresponding training sample in the plurality of training samples, (i) inputting the respective image as input to the untrained or partially trained model thereby obtaining a corresponding calculated indication that localizes one or more objects in the corresponding image that fall within each respective morphological class in the at least the second subset of morphological classes. The process further comprises (ii) using at least a difference between the corresponding calculated indication and the corresponding measured indication to update all or a subset of the plurality (e.g., at least 10,000) of parameters, thereby forming the trained model, where the trained model is configured to identify, for each respective morphological class in the plurality of morphological classes, a corresponding one or more objects that fall within the respective morphological class.

In some embodiments, the plurality of training samples comprises at least 1,000 training samples.

In some embodiments, the plurality of training samples comprises at least 20, at least 40, at least 60, at least 80, at least 100, at least 150, at least 200, at least 250, at least 300, at least 350, at least 400, at least 450, at least 500, at least 600, at least 700, at least 800, at least 900, at least 1000, at least 2000, at least 3000, at least 4000, at least 5000, at least 6000, at least 7000, at least 8000, at least 9000, at least 10,000, at least 20,000, at least 50,000, at least 100,000, at least 200,000, at least 500,000, or at least 1 million training samples. In some embodiments, the plurality of training samples comprises no more than 2 million, no more than 500,000, no more than 100,000, no more than 50,000, no more than 20,000, no more than 10,000, no more than 5000, no more than 2000, no more than 1000, or no more than 500 training samples. In some embodiments, the plurality of training samples consists of from 2 to 100,000, from 100 to 500,000, from 10 to 5000, from 10,000 to 50,000, from 100,000 to 1 million, or from 1 million to 2 million training samples. In some embodiments, the plurality of training samples comprises a different range starting no lower than 20 training samples and ending no higher than 2 million training samples.

In some embodiments, the plurality of training samples includes, for each respective training kidney graft biopsy, a subset of training images obtained from a respective training whole-slide image of the respective training kidney graft biopsy. In some such embodiments, a respective training whole-slide image of the respective training kidney graft biopsy is divided into a respective set of image tiles, where each respective image tile in the respective set of image tiles is a different portion of the respective training whole-slide image.

In some embodiments, the model comprises any of the architectures disclosed above (see, e.g., the section entitled "Trained model," above). In some embodiments, the model comprises a plurality of component models, and the training comprises training each of the component models individually or together.

Accordingly, in some embodiments, the model comprises a plurality of component models, and, for each respective component model in the plurality of component models, the plurality of training samples comprises a respective subset of training samples that is used to train the respective component model. In some embodiments, each respective component model is trained using the plurality of training samples in the training dataset.

In some embodiments, the second subset of morphological classes includes at least 1, at least 2, at least 3, at least 4, at least 5, at least 6, at least 7, at least 8, at least 9, or at least 10 morphological classes. In some embodiments, the second subset of morphological classes comprises no more than 20, no more than 10, no more than 8, no more than 5, or no more than 3 morphological classes. In some embodiments, the second subset of morphological classes consists of from 1 to 5, from 2 to 8, from 10 to 20, or from 5 to 15 morphological classes. In some embodiments, the second subset of morphological classes falls within another range starting no lower than 1 morphological class and ending no higher than 20 morphological classes.

In some embodiments, the second subset of morphological classes and the first subset of morphological classes is the same.

In some embodiments, the second subset of morphological classes includes all of the morphological classes in the plurality of morphological classes. Accordingly, referring to Block 252, in some embodiments, each respective training sample in the plurality of training samples comprises, for each respective morphological class in the plurality of morphological classes, a corresponding measured indication that localizes one or more objects in the corresponding image that fall within the respective morphological class.

In some embodiments, the corresponding measured indication indicates the location, within the respective training image, of one or more tissue compartment classes and/or inflammatory marker classes. In some embodiments, the corresponding measured indication indicate the location, within the respective training image, of one or more tubules, glomeruli, interstitium, and/or MNLs. For example, as described below in Example 1, in some embodiments, interstitium is defined as intertubular, nonglomerular space within tissue sections. In some embodiments, abnormal tubules are defined as shrunken tubules with a thickened and wrinkled membrane.

In some embodiments, the corresponding measured indication is obtained using an annotation by one or more clinicians, pathologists, and/or medical practitioners.

In some embodiments, the training the untrained or partially trained model further comprises using at least a difference between the corresponding calculated indication and the corresponding measured indication obtained for each training sample in the plurality of training samples to update all or a subset of the plurality of parameters (e.g., 10,000 or more parameters), thereby training the model to identify, for each respective morphological class in the plurality of morphological classes, a corresponding one or more objects that fall within the respective morphological class.

Generally, training a model (e.g., a neural network) comprises updating the plurality of parameters (e.g., weights) for the respective classifier through backpropagation (e.g., gradient descent). First, a forward propagation is performed, in which input data (e.g., a corresponding image for each respective training sample in a plurality of training samples in the training dataset) is accepted into the model, and an output is calculated based on the selected activation function and an initial set of parameters (e.g., weights and/or hyperparameters). In some embodiments, parameters (e.g., weights and/or hyperparameters) are randomly assigned (e.g., initialized) for the untrained or partially trained model. In some embodiments, parameters are transferred from a previously saved plurality of parameters or from a pretrained model (e.g., by transfer learning).

A backward pass is then performed by calculating an error gradient for each respective parameter corresponding to each respective unit (e.g., for a neural network, each respective unit in each respective layer), where the error for each parameter is determined by calculating a loss (e.g., error) based on the model output (e.g., the predicted value) and the input data (e.g., the expected value or true labels). Parameters (e.g., weights) are then updated by adjusting the value based on the calculated loss, thereby training the model.

For example, in some general embodiments of machine learning, backpropagation is a method of training a network with hidden layers comprising a plurality of weights (e.g., embeddings). The output of an untrained model (e.g., the calculated indication for one or more morphological class objects generated by a neural network) is first generated using a set of arbitrarily selected initial weights. The output is then compared with the original input (e.g., the measured indication for the one or more morphological class objects obtained from the training dataset) by evaluating an error function to compute an error (e.g., using a loss function). The weights are then updated such that the error is minimized (e.g., according to the loss function). In some embodiments, any one of a variety of backpropagation algorithms and/or methods are used to update the plurality of weights, as will be apparent to one skilled in the art.

In some embodiments, the loss function is mean square error, quadratic loss, mean absolute error, mean bias error, hinge, multi-class support vector machine, and/or cross-entropy. In some embodiments, training the untrained or partially trained neural network comprises computing an error in accordance with a gradient descent algorithm and/or a minimization function.

In some embodiments, the error function is used to update one or more parameters (e.g., weights) in a model by adjusting the value of the one or more parameters by an amount proportional to the calculated loss, thereby training the model. In some embodiments, the amount by which the parameters are adjusted is metered by a learning rate hyperparameter that dictates the degree or severity to which parameters are updated (e.g., smaller or larger adjustments). Thus, in some embodiments, the training updates all or a subset of the plurality of parameters (e.g., 10,000 or more parameters) based on a learning rate. In some embodiments, the learning rate is a differential learning rate.

In some embodiments, the training further uses a regularization on the corresponding parameter of each respective unit (e.g., for a neural network, each hidden neuron in the corresponding plurality of hidden neurons). For example, in some embodiments, a regularization is performed by adding a penalty to the loss function, where the penalty is proportional to the values of the parameters in the trained or untrained model. Generally, regularization reduces the complexity of the model by adding a penalty to one or more parameters to decrease the importance of the respective units associated with those parameters. Such practice can result in a more generalized model and reduce overfitting of the data. In some embodiments, the regularization includes an L1 or L2 penalty. For example, in some preferred embodiments, the regularization includes an L2 penalty on lower and upper parameters. In some embodiments, the regularization comprises spatial regularization or dropout regularization. In some embodiments, the regularization comprises penalties that are independently optimized.

Accordingly, in some embodiments, the training (b) is characterized by one or more hyperparameters in the at least 10,000 parameters.

In some embodiments, a respective hyperparameter in the one or more hyperparameters comprises a predetermined number of training epochs. In some such embodiments, the training includes repeating the adjustment of the parameters of the model (e.g., via backpropagation) over a plurality of instances, therefore increasing the model's accuracy in generating calculated indications.

In some embodiments, the plurality of training epochs comprises at least 3, at least 4, at least 5, at least 6, at least 7, at least 8, at least 9, at least 10, at least 50, at least 100, at least 500, at least 1000, at least 2000, at least 3000, at least 4000, at least 5000, or at least 7500 training epochs. In some embodiments, the plurality of training epochs comprises no more than 10,000, no more than 5000, no more than 1000, no more than 500, no more than 100, or no more than 50 training epochs. In some embodiments, the plurality of training epochs consists of from 3 to 10, from 5 to 100, from 100 to 5000, or from 1000 to 10,000 training epochs. In some embodiments, the plurality of training epochs falls within another range starting no lower than 3 training epochs and ending no higher than 10,000 training epochs.

In some embodiments, a respective hyperparameter in the one or more hyperparameters comprises a predetermined batch size, where the size specifies a number of corresponding training images of a predetermined number of training samples in the plurality of training samples.

In some embodiments, the batch size is at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 training images selected from the plurality of training samples. In some embodiments, the batch size is no more than 300, no more than 100, no more than 95, no more than 90, no more than 85, no more than 80, no more than 75, no more than 70, no more than 65, no more than 60, no more than 55, no more than 50, no more than 45, no more than 40, no more than 35, no more than 30, no more than 25, no more than 20, no more than 15, no more than 10, no more than 5 or fewer training images selected from the plurality of training samples. In some embodiments, the batch size is from 3 to 50, from 5 to 40, from 10 to 80, from 20 to 100, or from 50 to 300 training images. In some embodiments, the batch size falls within another range starting no lower than 3 training images and ending no higher than 300 training images.

In some embodiments, a respective hyperparameter in the one or more hyperparameters comprises a predetermined learning rate. In some embodiments, the learning rate is at least 0.0001, at least 0.0005, at least 0.001, at least 0.005, at least 0.01, at least 0.05, at least 0.1, at least 0.2, at least 0.3, at least 0.4, at least 0.5, at least 0.6, at least 0.7, at least 0.8, at least 0.9, or at least 1. In some embodiments, the learning rate is no more than 1, no more than 0.9, no more than 0.8, no more than 0.7, no more than 0.6, no more than 0.5, no more than 0.4, no more than 0.3, no more than 0.2, no more than 0.1 no more than 0.05, no more than 0.01, or less. In some embodiments, the learning rate is from 0.0001 to 0.01, from 0.001 to 0.5, from 0.001 to 0.01, from 0.005 to 0.8, or from 0.005 to 1. In some embodiments, the learning rate falls within another range starting no lower than 0.0001 and ending no higher than 1.

In some embodiments, the model comprises a plurality of component models, where each respective component model in the plurality of component models has the same hyperparameters. In some embodiments, a first respective component model in the plurality of component models has different hyperparameters from a second respective component model in the plurality of component models.

In some embodiments, the training comprises transfer learning. Transfer learning is further described, for example, in the Definitions section (see, "Untrained models," above).

In some embodiments, training the untrained or partially trained model forms a trained model following a first evaluation of an error function. In some such embodiments, training the untrained or partially trained model forms a trained model following a first updating of one or more parameters based on a first evaluation of an error function. In some alternative embodiments, training the untrained or partially trained model forms a trained model following at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million evaluations of an error function. In some such embodiments, training the untrained or partially trained model forms a trained model following at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million updatings of one or more parameters based on the at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million evaluations of an error function.

In some embodiments, training the untrained or partially trained model forms a trained model when the model satisfies a minimum performance requirement. For example, in some embodiments, training the untrained or partially trained model forms a trained model when the error calculated for the trained model, following an evaluation of an error function across one or more training images for a respective one or more training samples, satisfies an error threshold. In some embodiments, the error calculated by the error function across one or more training images for a respective one or more training samples satisfies an error threshold when the error is less than 20 percent, less than 18 percent, less than 15 percent, less than 10 percent, less than 5 percent, or less than 3 percent. Thus, for example, in some embodiments, a trained model is formed when the best performance is achieved (e.g., in some instances, a trained model is selected from an earlier training instance rather than a later training instance, if the earlier training instance resulted in better performance than the later training instance).

In some embodiments, model performance is measured using a training loss metric, a validation loss metric, and/or a mean absolute error. For instance, in some embodiments, model performance is measured by validating the model using one or more validation images in a validation dataset and determined based at least on a difference between a corresponding calculated indication and a corresponding measured indication obtained for each validation image in the one or more validation images in the validation dataset. In some such embodiments, training the untrained or partially trained model forms a trained model when the model satisfies a minimum performance requirement based on a validation training.

In some embodiments, the method comprises any suitable method for validation, including but not limited to K-fold cross-validation, advanced cross-validation, random cross-validation, grouped cross-validation (e.g., K-fold grouped cross-validation), bootstrap bias corrected cross-validation, random search, and/or Bayesian hyperparameter optimization.

In some embodiments, k is 1, 2, 3, 4, 5, 6, 7, 8, 9, or 10. In some embodiments, k is at least 5, at least 10, at least 15, at least 20, or at least 30. In some embodiments, k is no more than 50, no more than 30, no more than 20, or no more than 10. In some embodiments, k is from 5 to 15, from 8 to 12, from 3 to 20, or from 20 to 50. In some embodiments, k falls within another range starting no lower than 1 and ending no higher than 50.

In some embodiments, the validation dataset is a hold-out test set obtained from the training dataset.

Additional embodiments for model training are further described in Yi et al., "Deep learning identified pathological abnormalities predictive of graft loss in kidney transplant biopsies," Kidney International (2022) 101, 288-298; doi: 10.1016/j.kint.2021.09.028, which is hereby incorporated herein by reference in its entirety.

Additional Embodiments

Another aspect of the present disclosure provides a computing system, comprising one or more processors and memory storing one or more programs to be executed by the one or more processor, the one or more programs comprising instructions for a method of identifying a risk of kidney graft failure for a subject. The method comprises obtaining, in electronic format, a first image of a kidney graft biopsy on a substrate, where the first image represents at least a first subset of morphological classes in a plurality of morphological classes comprising at least a first tissue compartment class and an inflammatory mediator class, the first image comprises at least 10,000 pixels, and the graft biopsy originates from the subject. The first image is inputted into a trained model, where the trained model comprises at least 10,000 parameters.

The method includes identifying, as output from the trained model, for each respective morphological class in the at least the first subset of morphological classes, a corresponding one or more objects in the first image that fall within the respective morphological class, where the first subset of morphological classes includes the first tissue compartment class or the inflammatory mediator class. The method further includes generating, for each respective morphological class in the at least the first subset of morphological classes, a corresponding plurality of digital features comprising (i) a first corresponding subset of individual feature scores, where each respective individual feature score is obtained using the corresponding one or more objects for the respective morphological class, and (ii) a second corresponding subset of composite feature scores, where each respective composite feature score is obtained by combining two or more individual feature scores in the first corresponding subset of individual feature scores. For each respective morphological class in the at least the first subset of morphological classes, a respective digital feature in the corresponding plurality of digital features for the respective morphological class is compared to a reference criterion, thereby determining the risk of kidney graft failure for the subject.

Another aspect of the present disclosure provides a non-transitory computer readable storage medium storing one or more programs for identifying a risk of kidney graft failure for a subject, the one or more programs configured for execution by a computer. The one or more programs comprise instructions for obtaining, in electronic format, a first image of a kidney graft biopsy on a substrate, where the first image represents at least a first subset of morphological classes in a plurality of morphological classes comprising at least a first tissue compartment class and an inflammatory mediator class, the first image comprises at least 10,000 pixels, and the graft biopsy originates from the subject. The first image is inputted into a trained model, where the trained model comprises at least 10,000 parameters.

The method includes identifying, as output from the trained model, for each respective morphological class in the at least the first subset of morphological classes, a corresponding one or more objects in the first image that fall within the respective morphological class, where the first subset of morphological classes includes the first tissue compartment class or the inflammatory mediator class. The method further includes generating, for each respective morphological class in the at least the first subset of morphological classes, a corresponding plurality of digital features comprising (i) a first corresponding subset of individual feature scores, where each respective individual feature score is obtained using the corresponding one or more objects for the respective morphological class, and (ii) a second corresponding subset of composite feature scores, where each respective composite feature score is obtained by combining two or more individual feature scores in the first corresponding subset of individual feature scores. For each respective morphological class in the at least the first subset of morphological classes, a respective digital feature in the corresponding plurality of digital features for the respective morphological class is compared to a reference criterion, thereby determining the risk of kidney graft failure for the subject.

Still another aspect of the present disclosure provides a computing system including the above-disclosed one or more processors and memory storing one or more programs that further comprise instructions for performing any of the above-disclosed methods alone or in combination.

Another aspect of the present disclosure provides non-transitory computer-readable storage medium comprising the above-disclosed one or more programs in which the one or more programs further comprise instructions for performing any of the above-disclosed methods alone or in combination. The one or more programs are configured for execution by a computer.

EXAMPLES

Example 1—Applying Artificial Intelligence Techniques to Baseline (Pre-Implantation) and Post-Transplantation Biopsies to Identify Quantitative Digital Features An analysis was performed seeking an objective, quantitative pathological assessment of renal lesions (e.g., interstitial fibrosis, tubular atrophy, and inflammation) to improve predictive utility and to construct a deep-learning-based pipeline recognizing various conditions (e.g., normal vs. abnormal) for morphological classes of kidney biopsies, including kidney tissue compartments and mononuclear leukocyte infiltrates. Periodic acid-Schiff stained slides of graft biopsies (60 training and 33 testing) were used to quantify objects indicative of pathological lesions specific for these classes, including interstitium, tubules and mononuclear leukocyte infiltration. The pipeline was applied to whole-slide images from 789 transplant biopsies (478 baseline [pre-implantation] and 311 post-transplant 12-month protocol biopsies) in two independent patient cohorts (Go-CAR: 404 patients, AUSCAD: 212 patients) of transplant recipients to correlate composite lesion features (e.g., digital features) with graft loss. The constructed model accurately recognized objects within the tissue compartment class (e.g., kidney tissue compartments) and objects within the inflammatory marker class (e.g., mononuclear leukocytes). The digital features significantly correlated with reference measures of kidney damage such as revised Banff 2007 scores but were more sensitive to subtle pathological changes below the thresholds in the Banff scores. A composite feature score, the Interstitial and Tubular Abnormality Score (ITAS), in baseline pre-implantations samples was highly predictive of one-year graft loss, while a composite class score, the Composite Damage Score (CDS), in 12-month post-transplant protocol biopsies predicted later graft loss. ITASs and Composite Damage Scores outperformed reference measures of kidney damage such as Banff scores or clinical predictors with superior graft loss prediction accuracy. High/intermediate risk groups stratified by ITASs or Composite Damage Scores also demonstrated significantly higher incidence of various indicators of kidney graft failure such as estimated glomerular filtration rate (eGFR) decline and subsequent graft damage. Thus, the deep-learning approach disclosed herein accurately detected and quantified pathological lesions from images of baseline or post-transplant kidney graft biopsies using determined digital features and demonstrated superior ability for prediction of post-transplant graft loss using the same, with potential application as a prevention, risk stratification or monitoring tool. See, Yi et al., "Deep learning identified pathological abnormalities predictive of graft loss in kidney transplant biopsies," Kidney International (2022) 101, 288-298; doi: 10.1016/j.kint.2021.09.028, which is hereby incorporated herein by reference in its entirety.

Methods

Study Cohorts and Biopsy Slides

Figure 3A:
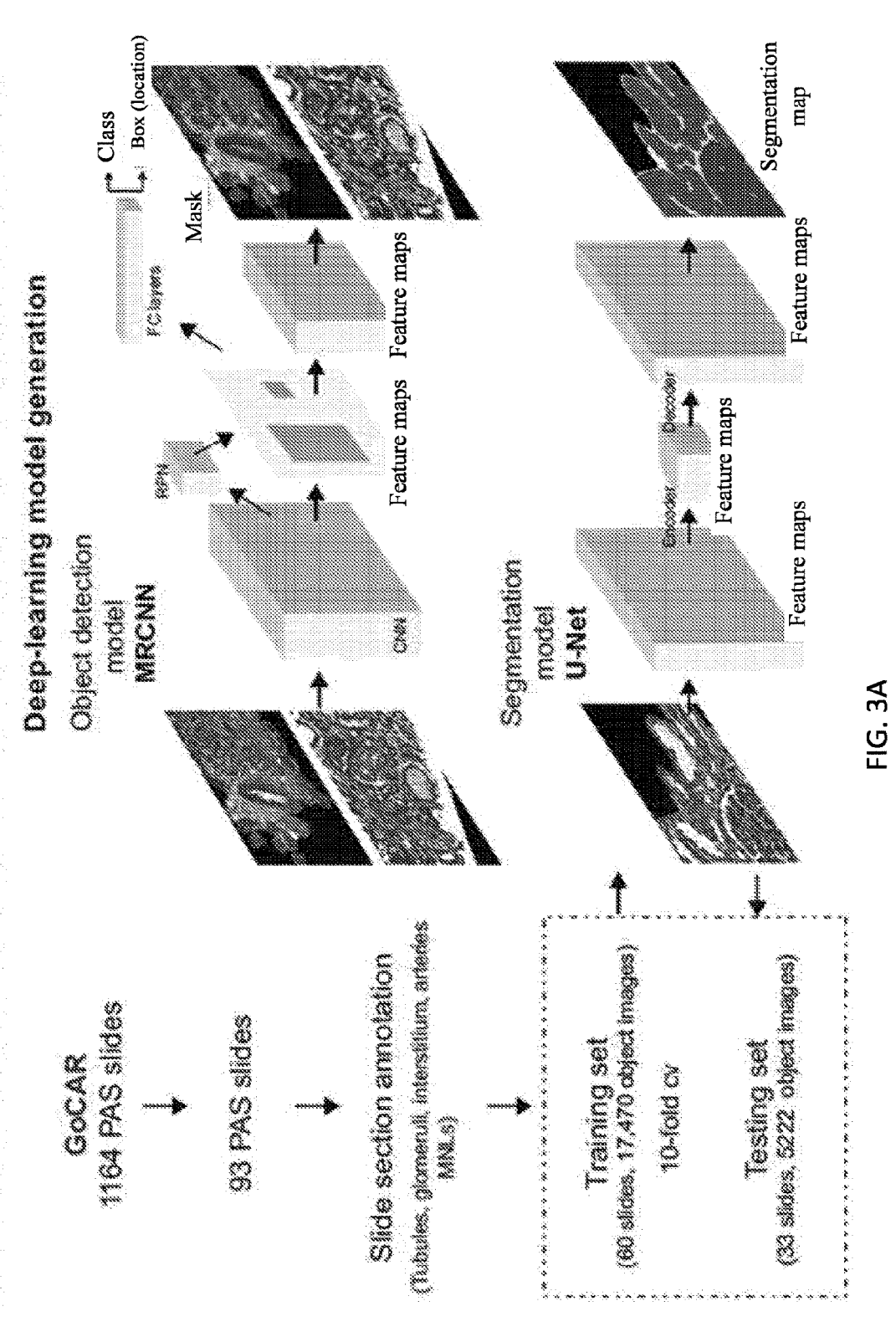
FIGS. 3A and 3B collectively illustrate an example schematic for a study design, in accordance with an embodiment of the present disclosure. The study consists of 2 major stages.
Figure 3B:
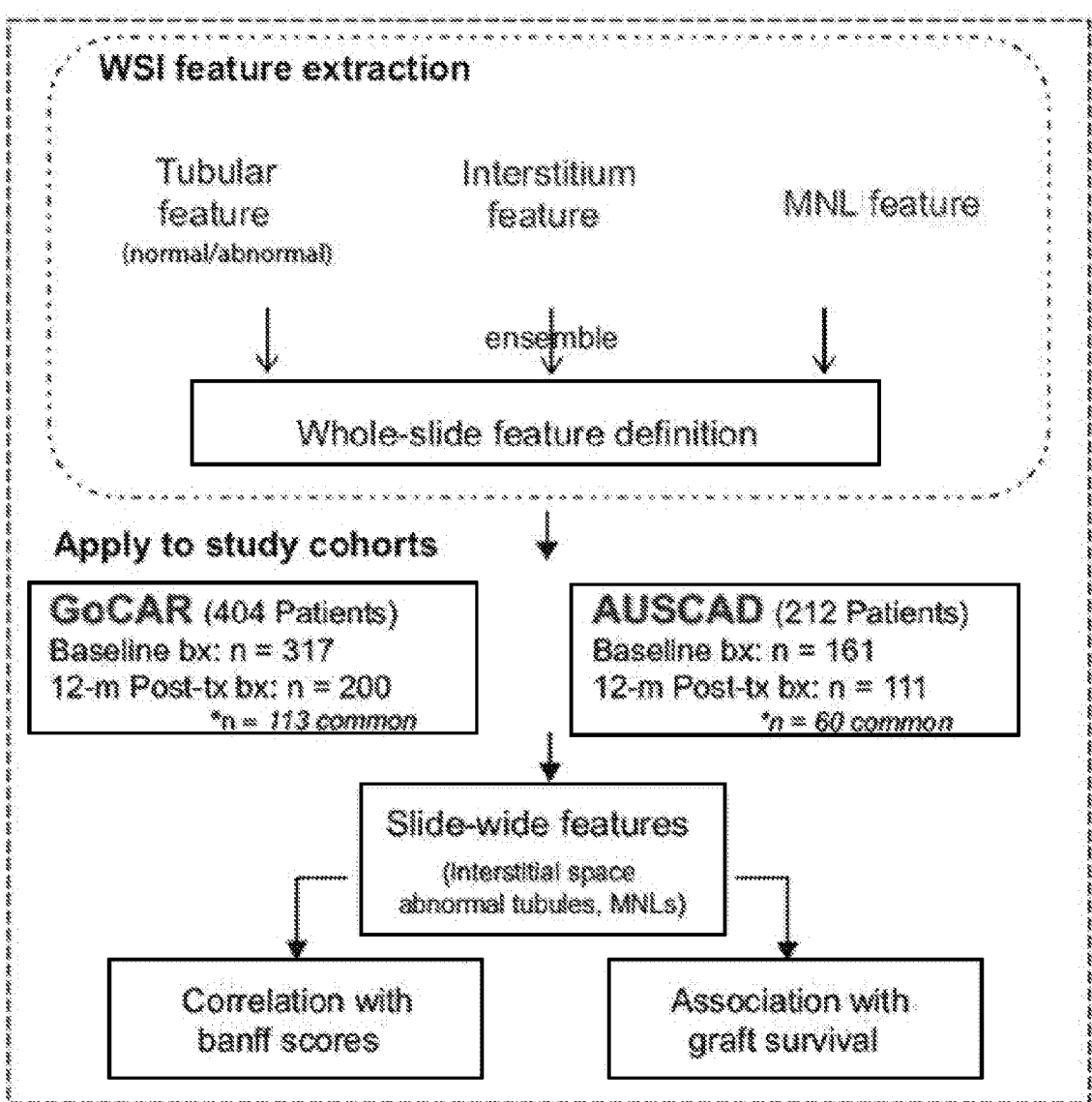

The Genomics of Chronic Allograft Rejection (GoCAR) 22 study is a prospective, multicenter study with patients that have been followed for a median of 5 years. Australian Chronic Allograft Dysfunction (AUSCAD) is an Australia transplant cohort from Westmead Hospital, University of Sydney with patients being followed for a median duration of 4.5 years. Living and deceased-donor recipients between 18 and 75 years old were included and sensitized; patients with multiple organ transplants were excluded in this study. Blood, kidney biopsy specimens, and clinical data were collected at the time of post-transplantation visit. In GoCAR, 2 protocol biopsy samples were taken from baseline (pre-implantation) or various times (3, 12, and 24 months) post-transplantation. One formalin-fixed, paraffin-embedded core was processed for histologic stains, and the image obtained therefrom was scored centrally and agreed by at least 2 pathologists at Massachusetts General Hospital according to revised Banff 2007 classification for renal allograft pathology (23) at the time of biopsy. AUSCAD biopsy samples were formalin-fixed and paraffin-embedded prior to routine histologic staining including periodic acid-Schiff (PAS). Images obtained from these biopsies were scored locally at Westmead according to the revised Banff 2007 classification for renal allograft pathology and reviewed by pathologists at Massachusetts General Hospital to ensure consistency in diagnosis between the 2 centers. GoCAR slides were scanned with Aperio CS scanner at ×20 objective with a×2 magnifier; AUSCAD slides were scanned by scanner from Hamamatsu company with a×20 objective. PAS-stained slides in both cohorts were used in this study (FIGS. 3A-B).

To fully capture abnormalities regarding interstitium, tubules, and inflammation (e.g., objects relating to each of the morphological classes in the plurality of morphological classes including tissue compartment classes and an inflammatory mediator class), a training dataset including kidney graft biopsy images was selected to incorporate all types of abnormal cases covering all 3 aspects. However, due to the various incidences of pathologic lesions observed in 1164 kidney biopsies taken at various time points in the entire GoCAR cohort, a random selection of a subset from these biopsies may miss certain types of abnormal instances. Therefore, each PAS-stained slide was examined and 93 slides that represented the spectrum of histologic lesions (e.g., all of the morphological classes in the plurality of morphological classes) were selected as the training dataset to be used for model construction. Multiple selected regions covering glomeruli, interstitium, tubules, arteries, and MNL infiltration on these slides were annotated under the guidance of pathologists prior to model generation and training. Here, abnormal tubules were defined as shrunken tubules with thickened and wrinkled membrane, while interstitium was defined as intertubular, nonglomerular space within tissue sections. Next, the established whole-slide image (WSI) investigation pipeline was applied to all available PAS-stained slides, including 478 slides at baseline (GoCAR, n=317; AUSCAD, n=161) and 311 slides at 12 months post-transplantation (GoCAR, n=200; AUSCAD, n=111) to extract digital features to be correlated with graft survival. These slides represented 404 patients from the GoCAR cohort and 212 patients from the AUSCAD cohort.

WSI Deep-Learning Analysis

The WSI deep-learning analysis procedure was divided into 2 stages: stage I included development of deep-learning-based component models for morphological class object (e.g., tissue compartment and/or inflammatory mediator) recognition; and stage II included the application of pre-trained component models on WSI to extract slide-wide features to be correlated with graft outcomes (details are depicted in FIGS. 3A-B and FIGS. 7A-B and described in the Supplementary Methods, below). Briefly, at stage I, annotated PAS sections including most tissue compartments were preprocessed into 22,692 fixed-sized image tiles for model generation. The deep-learning model was tuned on training image tiles from 60 slides with 10-fold cross-validation to avoid overfitting and the established model was tested on an independent image tile set from 33 slides for unbiased model evaluation.

Within the model, a component compartment detection model and a component MNL detection model were constructed using Mask R-CNN (20) and a component interstitium estimation model was constructed using U-Net (19). Detailed hyperparameter settings are further described in the Supplementary Methods, below. Prediction results were paired with ground truth annotations that provided measured indications as to the location of one or more objects for the various morphological classes. Accuracies were measured by true positive rate, positive predictive value, and general $F_\beta$ score (weighted harmonic mean between precision and recall) (24), where $\beta=2$.

At stage II, outputs from pretrained morphological class object (e.g., tissue compartment and/or inflammatory mediator) recognition component models were first combined into whole-slide prediction images. A convolutional "window" (e.g., a filter) was used to scan across the entirety of the whole-slide prediction image and thus define interstitial or inflammatory regions of interest (ROI) and slide-wide digital features capturing abnormalities in one or more of the plurality of morphological classes (e.g., objects representing interstitium, tubules, and MNL infiltration). These individual digital features were then summarized into composite features (e.g., composite feature scores and/or composite class scores) reflecting overall kidney damage. This WSI feature extraction process was applied to the 2 independent transplant cohorts (GoCAR and AUSCAD) and the estimated digital features were correlated with Banff scores and graft survival separately.

Statistical Analysis

Quantitative outcomes such as Banff scores or eGFR were treated as continuous variables and used as reference measures of kidney damage, and missing data were excluded for specific analyses. Association of digital features with Banff scores or eGFR were measured by Spearman's correlation. Graft loss was defined as loss of graft function; association with graft loss was assessed by Cox proportional hazards regression; and multiple testing correction was applied. Time-dependent area under the curve (AUC) values were estimated by R package "timeROC" (25), where T denotes follow-up days of a patient. At a certain time point t, a case is defined as patient lost graft at T≤t; a control is defined as patient survived through t (T>t). As for survival confounders adjustment, a series of clinical vial parameters including recipient age, sex, race, donor age, number of transplants, kidney diseases, living or deceased donor, human leukocyte antigen mismatch, cold ischemia time (CIT), induction type, baseline donor-specific antibodies, and delayed graft function were first evaluated with graft loss through univariate analysis. Significant parameters—living or deceased donor, CIT, baseline donor-specific antibodies, human leukocyte antigen mismatch, and induction type—were selected as confounders. Further investigations of graft loss and other graft outcomes among risk groups stratified by composite scores were evaluated by log-rank test and Fisher's exact test, respectively.

Supplementary Methods.

Image Pre-Processing

Multiple sections from 93 GoCAR (S1) PAS-stained slides were annotated for tissue compartment and mononuclear leukocytes (MNL) prediction using ASAP software (computationalpathologygroup.github.io/ASAP/) under the guidance of pathologists. Thus, training images within the training dataset were annotated with measured indications that localized morphological class objects for the tissue compartment and inflammatory marker classes. Each section was outlined by a boundary and the area within boundary but apart from annotated objects were defined as interstitium by default. The raw sections were divided into 22,692 fixed-sized image tiles at 20× objective-power and then transformed by a data augmentation process (S2) including position shifting, rotating, flipping, perspective transforming, color transferring, contrast transforming, or noise feeding. Every fixed-sized image tile was paired with a reference image tile that included a measured indication of morphological class objects in the image tile (e.g., a ground truth classification image labeling group information at the same size) for model evaluation. These two types of images were served as input to the model, for the model training and construction process.

Deep-Learning Model Generation

The 93 slides in the training dataset were divided at roughly a 2:1 ratio into a discovery set (n=60) and a testing set (n=33). The discovery set (e.g., the plurality of training samples) was used for a model training and construction process and the testing set was used for final evaluation and was kept untouched during the training process. 10-fold cross-validation was performed within the discovery set, thus dividing the discovery set into 10 equally sized subsets. During each round of the model training process, 9 out of 10 subsets were used as a training set and the remaining 1 subset, as the left-out subset, was used as a validation set to tune the model. As a result, 10 separate base models were created based on the 10 partitioned subsets and the final prediction was made by aggregating results from each base model.

A plurality of component models were used to generate the final model. Each component model was a convolutional neural network (CNN) structure. A first model architecture segmented images at instance level: Mask Region-based Convolutional Neural Network (Mask R-CNN) (S3). A second model architecture segmented images at pixel level: U-Net (S4). The first model architecture Mask R-CNN first extracts feature maps from input images by a convolutional backbone structure and generates region proposal of given objects through a Region Proposal Network (RPN). Accordingly, these region proposals provide indications as to the location of the one or more objects that fall within respective morphological classes in the plurality of morphological classes including the first tissue compartment class (e.g., tubules and/or glomeruli) and the inflammatory marker class (e.g., MNLs). These proposed regions were later passed through another neural network to generate multi-categorical classes, bounding boxes and masks for objects. The second model architecture U-Net on the other hand makes predictions for each pixel instead of instances on input images. It has a symmetrical "U" shape architecture consisting of an encoder which extracts features from input images by convolution blocks and a decoder which expends contracted vector back to segmentation map at input size. The number of blocks in the encoder step is the same as the number of blocks in the decoder step. Thus, the segmentation map provides the indications as to the locations of the one or more objects, in the image, that falls within a respective morphological class in the plurality of morphological classes including a second tissue compartment class (e.g., interstitium estimation).

A compartment detection model (e.g., tubules, glomeruli) and a MN leukocyte detection model (e.g., MNLs) were constructed using Mask R-CNN structure (S5) and a tissue segmentation model (e.g., interstitium) was constructed using U-net structure (S6). Specifically, the compartment detection model was trained for 90 epochs with a batch size of 10, using input images, for each respective training sample, having a size of 1024×1024 pixels. The MN leukocyte detection model was trained for 250 epochs with a batch size of 6, using input images having a size of 512×512 pixels. The tissue segmentation model was trained for 100 epochs with a batch size of 8, using input images having a size of 512×512 pixels. The detection model used RestNet-101 as a backbone and was tuned based on pre-trained weights from MS COCO dataset (S7). A GSD optimizer was applied with a learning rate of 0.001 and momentum of 0.9. Total loss was calculated as the sum of loss of RPN classifier, RPN bounding box, MR-CNN classifier, MR-CNN bounding box, and MR-CNN mask, where cross-entropy was used for classification problems and smooth L1-loss was used for bounding box refinement. The segmentation model was constructed using 3 down-sampling layers and 3 up-sampling layers and the first layer contained 32 feature maps. The ADAM optimizer was chosen for weight updating at learning rate of 0.001 and cross-entropy was used for loss function. A best epoch/model was determined by evaluating loss from each training and validation partition. Finally, the best model was to the testing dataset for unbiased model evaluation. Accuracies were measured by True Positive Rate (TPR), Positive Predictive Value (PPV) and general $F_\beta$ score (S8), where $\beta=2$.

The GPU machine used was equipped with 36 Intel® Xeon® W-2195 CPUs (18 cores), 128 GB Memory, and 4 GPUs of Quadro RTX 8000. All processes ran on Ubuntu 18.04 system.

Whole Slide Investigation and Digital Feature Definition

The model, including the above three component models, was applied to whole slide images (WSI) and results were assembled into full prediction masks including all tissue compartment objects and MN leukocytes (e.g., all objects that fall within each respective morphological class in the plurality of morphological classes). Since this study focused on the features in cortex, medullar region and adjacent artery along with imperfectly cut or scanned fragments were excluded in the WSI analysis.

Due to the instance and pixel level prediction nature of MR-CNN and U-Net, object counting as well as area estimation could be performed. In general, from WSI prediction, a plurality of basic individual feature scores such as the size of a slide, the number of glomeruli and tubules, the percentage of glomeruli, tubules and interstitial area over slide, as well as a series of abnormal features focusing on interstitial space, abnormal tubules and inflammation were defined.

Figure 7A:
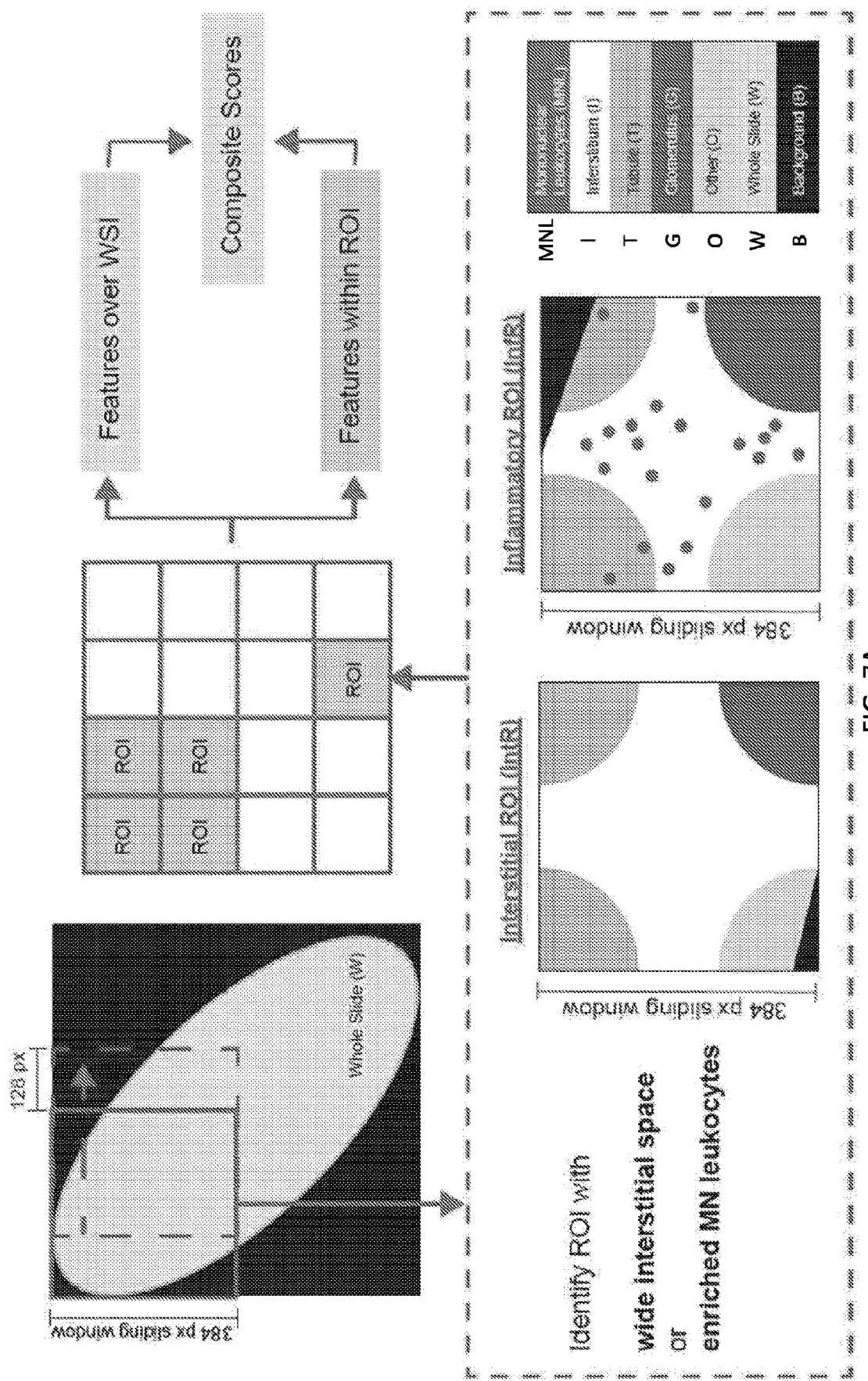
FIGS. 7A and 7B collectively illustrate a schematic for slide-wide digital feature extraction and definition, in accordance with an embodiment of the present disclosure.

To define slide-wide abnormal features, the concept of Region of Interest (ROI) window was introduced to identify local abnormal regions with respect to interstitium and inflammation (FIG. 7A). Given a whole slide prediction image, a 384×384 pixel unit "window" (e.g., a filter) sliding over the image with stride of 128 pixels was applied. Within each unit window, a set of object population metrics including Sparsity(I), Densify(O), Density(B), and Density(MNL) were examined and used to define interstitial ROI and inflammatory ROI.

For example, a unit window was determined as interstitial ROI if it had wide interstitial space but narrow space of background noise in tubule-enriched regions as defined as: Sparsity I>0.35, Density(O)<0.2, and Density(B)<0.2, where $$\text{Sparsity}(I) = \frac{\text{area}(InterstitialSpace)}{\text{area}(InterstitialSpace) + \text{area}(\text{Tubule})} \text{ per unit window,}$$

$$\text{Density}(O) = \frac{\text{area}(Glomeruli) + \text{area}(OtherGroups)}{384 \times 384} \text{ per unit window, and}$$

$$\text{Density}(B) = \frac{\text{area}(\text{Background})}{384 \times 384} \text{ per unit window.}$$

As another example, a unit window was determined to be an inflammatory ROI if it had enriched mononuclear leukocytes (MNL) as Density(MNL)>43, where $$\text{Density(MNL)} = N(\text{MNL}) \text{ per unit window.}$$

For each respective slide in the training dataset, the corresponding image was processed by sliding the unit window (e.g., filter) across the whole-slide image or a region of interest thereof. The pipeline thus generated, for each respective image, two types of ROI masks highlighting abnormal interstitium area and MN leukocytes infiltration area, respectively. Abnormal features were then defined as abnormal individual feature scores for respective morphological classes, including interstitial space, abnormal tubules and MN leukocytes infiltration, at the WSI level or ROI level.

For example, abnormal individual feature scores for the interstitium included an estimate of overall percentage of interstitial space over WSI area, where Abnormal Interstitial Area Percentage =

$$\frac{\text{area}(\text{Interstitial Space within Interstitial } ROI)}{\text{area}(WSI)}.$$

Abnormal individual feature scores for tissue compartments (e.g., tubules) included a summary of a number of abnormal tubules per 1000×1000 unit area, where $$\text{Abnormal Interstitial Area Percentage} = \frac{N(\text{Abnormal Tubules})}{\text{area}(WSI)} \times 10^6.$$

Abnormal individual feature scores for inflammation (e.g., MNLs) included estimated proportion of MN leukocyte enriched area over WSI area, where $$MNL\text{-enriched Area Percentage} = \frac{\text{area}(\text{Inflammatory } ROI)}{\text{area}(WSI)},$$

and average number of MN leukocytes in inflammatory ROI per 1000×1000 unit area, where MNL Density (infR)=Average $N$(MNL) weighted
across Inflammatory ROIs.

Generally, digital features, including individual feature scores, were defined in consideration of two aspects: i) how widespread a given abnormal feature is over the area of a slide (such as Abnormal Interstitial Area Percentage and MNL-enriched Area Percentage); and ii) how dense a given abnormal object is per unit area (such as Abnormal Tubules Density and MNL Density (infR)).

Moreover, individual feature scores were integrated into composite feature scores. To obtain composite feature scores, individual feature scores were first rescaled through $\log_2$ transformation to correct for skewed distributions of density features. By multiplying the above-referenced coverage-based individual feature scores (area %) by density-based individual feature scores, the composite feature scores Interstitial and Tubular Abnormality Score (ITAS) and MNL infiltration Score (MNL-IS) were proposed to approximate the relative amount of IFTA (Interstitial Fibrosis and Tubular Atrophy) and MNLs. The max(x,0) function shown in the below MNL-IS and ITAS serves as a gate function to ensure non-negative values. Additionally, a final composite class score, the Composite Damage Score (CDS) was proposed to integrate abnormality regarding all three morphological classes of interstitium, tissue compartments (e.g., tubules and/or glomeruli), and inflammation (e.g., MNLs). Since the model tended to recognize MNLs within interstitial space, the proposed CDS was assumed to approximate interstitial IFTA at a certain level. Accordingly, MNL-IS, ITAS, and CDS were obtained as follows:

$$MNL\text{-}IS = \max(MNL \text{ enriched Area Percentage} \times \log_2(\text{Density}(infR)), 0),$$

$$ITAS = \max(\text{Abnormal Interstitial Area Percentage} \times$$

$$\log_2(\text{Abnormal Tubules Density}), 0), \text{ and}$$

$$CDS = MNL\text{-}IS + ITAS.$$

In some cases, patients had multiple segments per slide or re-scanned slides at the time of biopsy, resulting in multiple corresponding images per slide. In cases of multiple segments per slide, individual feature scores in the plurality of digital features were first estimated within each segment, weighted by relative size of segment using $$\frac{\text{area of segment}(i)}{\text{total area of all segments}},$$

and summed across multiple segments (except counting of glomeruli which was simply summed across segments). Therefore, individual feature scores extracted from large segments had more weight than those from small segments. In cases of re-scanned slides, a similar weighted average (by relative size of slide) method was performed to obtain features at patient level. Notably, similar feature outputs were observed for several re-scanned slides, which suggested the consistency and reproducibility of the digital feature generation methods disclosed herein, given the same slide.

In summary, the whole slide feature extraction pipeline generated three types of outputs for one WSI: i) whole slide prediction masks demonstrating kidney tissue compartments within a slide; ii) two ROI masks representing interstitium and inflammation abnormality; and iii) a comprehensive data report summarizing individual or composite feature scores.

Results.

Demographic and Clinical Characteristics of Study Cohorts

Machine learning techniques in accordance with an embodiment of the present disclosure were applied to all available PAS-stained slides of kidney donor biopsies taken at baseline (pre-implantation) or 12 months post-transplantation in 404 patients from a multicenter international cohort (GoCAR) (22) and 212 patients from an external Australian cohort (AUSCAD) (FIGS. 3A-B). Among these patients, 113 patients in GoCAR and 60 patients in AUSCAD had biopsies taken at both time points, and others were biopsied at either baseline or 12 months. The 2 populations had similar sex distribution, age, and CIT, but they differed in ethnicity and clinical management protocols (Table 1). Patients from GoCAR had more diverse ethnic backgrounds including African American or Hispanic (25% vs. none in AUSCAD), whereas AUSCAD recorded more deceased donors (78.77% vs. 53.71% in GoCAR). All patients from AUSCAD received induction therapy predominantly with lymphocyte nondepleting agents (93.87%), while among 78.22% of recipients from GoCAR who received induction, lymphocyte-depleting agents (Thymoglobulin or Campath-1) were used in 39.36% and nondepleting agents in 38.86%. Overall, the AUSCAD cohort had a lower graft loss rate (4.72% vs. 12.13% in GoCAR) during slightly shorter follow-up period (median 4.5 years vs. 5 years in GoCAR).

TABLE 1

Demographic and clinical characteristics in 2
independent kidney transplant cohorts.

| Characteristics | GoCAR (n = 404) | AUSCAD[a] (n = 212) | P value[b] |
|---|---|---|---|
| Recipient age, yr | 49.38 ± 13.52 | 48.44 ± 12.11 | 0.381 |
| Recipient sex | | | 0.282 |
| Female | 129 (31.93) | 77 (36.32) | |
| Male | 275 (68.07) | 135 (63.68) | |
| Recipient race | | | 1.7e-19 |
| Caucasian | 261 (64.6) | 177 (83.49) | |
| Asian | 24 (5.94) | 27 (12.74) | |
| African American | 76 (18.81) | 0 (0) | |
| Hispanic | 25 (6.19) | 0 (0) | |
| Other | 18 (4.46) | 8 (3.77) | |
| Dialysis | | | 6.0e-04 |
| No | 89 (22.03) | 23 (10.95) | |
| Yes | 315 (77.97) | 187 (89.05) | |
| Kidney disease | | | 1.3e-05 |
| Diabetes mellitus | 139 (34.41) | 79 (37.98) | |
| Glomerulonephritis | 74 (18.32) | 66 (31.73) | |
| Hypertension | 77 (19.06) | 14 (6.73) | |

TABLE 1-continued

Demographic and clinical characteristics in 2
independent kidney transplant cohorts.

| Characteristics | GoCAR (n = 404) | AUSCAD[a] (n = 212) | P value[b] |
|---|---|---|---|
| Polycystic kidney disease | 41 (10.15) | 20 (9.62) | |
| Other | 73 (18.07) | 29 (13.94) | |
| Donor age, yr | 42.02 ± 15.51 | 45.43 ± 16.8 | 0.019 |
| Donor sex | | | 0.609 |
| Female | 197 (48.76) | 105 (50.97) | |
| Male | 207 (51.24) | 101 (49.03) | |
| Deceased donor | | | 6.5e-10 |
| No | 187 (46.29) | 45 (21.23) | |
| Yes | 217 (53.71) | 167 (78.77) | |
| CIT, min | 530.65 ± 494.21 | 501.06 ± 245.1 | 0.324 |
| HLA mismatch | | | 0.010 |
| 0 | 46 (11.39) | 12 (6.19) | |
| 1-2 | 55 (13.61) | 42 (21.65) | |
| 3-4 | 150 (37.13) | 58 (29.9) | |
| 5-6 | 153 (37.87) | 82 (42.27) | |
| Delayed graft function | | | 9.0e-04 |
| No | 334 (82.67) | 150 (70.75) | |
| Yes | 70 (17.33) | 62 (29.25) | |
| Induction type | | | 5.1e-46 |
| Lymphocyte nondepletion | 157 (38.86) | 199 (93.87) | |
| Lymphocyte depletion | 159 (39.36) | 13 (6.13) | |
| None | 88 (21.78) | 0 (0) | |
| Follow-up, d | 1776.98 ± 660.2 | 1637.39 ± 849.81 | 0.038 |
| Death-censored graft loss | | | 0.002 |
| No | 355 (87.87) | 202 (95.28) | |
| Yes | 49 (12.13) | 10 (4.72) | |

Deep-Learning-Based WSI Investigation Defined Abnormality in Interstitium or Tubules and MNL Infiltration The 2-stage study described above (see, e.g., the section entitled "Methods: WSI deep-learning analysis") first generated a trained model consisting of a deep-learning model detecting tissue compartments and MNLs, and then defined digital features, including slide-wide abnormality features, to be correlated with reference measures of kidney damage, including Banff scores (23) and graft outcomes (FIGS. 3A-B, Supplementary Methods). In stage I, 3 types of models based on 2 deep-learning architectures were built on a plurality of training samples including 17,470 images from 60 slides using 10-fold cross-validation. The models, respectively, identified tissue compartments (tubules, glomeruli, etc.), MNLs (Mask R-CNN), and interstitial area (U-Net). The final model was tested on an independent set of 5,222 images from 33 slides, and accurately recognized 96% of glomeruli and 91% of tubules and differentiated normal and abnormal tubules at true positive rates of 81% and 84%, respectively. On the other hand, the model was able to detect 90% of normal epithelial cells as well as 77% of MNLs at the individual nuclei level. The slightly lower accuracy of MNL detection was reflective of challenges in MNL annotation on PAS slides. Lastly, 85% and 96% of predicted interstitial area and area covered by arteries were correctly identified (Table 2).

TABLE 2

Accuracy summary of kidney tissue
compartment prediction model.

| Group | Area Segmentation | | | Instance Detection | | |
|---|---|---|---|---|---|---|
| | TPR | PPV | F-score | TPR | PPV | F-score |
| Interstitium | 0.73 | 0.85 | 0.75 | — | — | — |
| Glomeruli | 0.94 | 0.87 | 0.93 | 0.96 | 0.97 | 0.96 |
| All Tubule | 0.93 | 0.84 | 0.91 | 0.91 | 0.85 | 0.90 |
| Normal Tubule | 0.92 | 0.79 | 0.89 | 0.81 | 0.77 | 0.80 |
| Abnormal Tubule | 0.79 | 0.78 | 0.79 | 0.84 | 0.76 | 0.82 |
| Artery | 0.84 | 0.96 | 0.86 | 0.75 | 0.89 | 0.77 |
| MN Leukocyte | — | — | — | 0.77 | 0.66 | 0.75 |
| Epithelial cell | — | — | — | 0.90 | 0.67 | 0.84 |

Figure 7B:
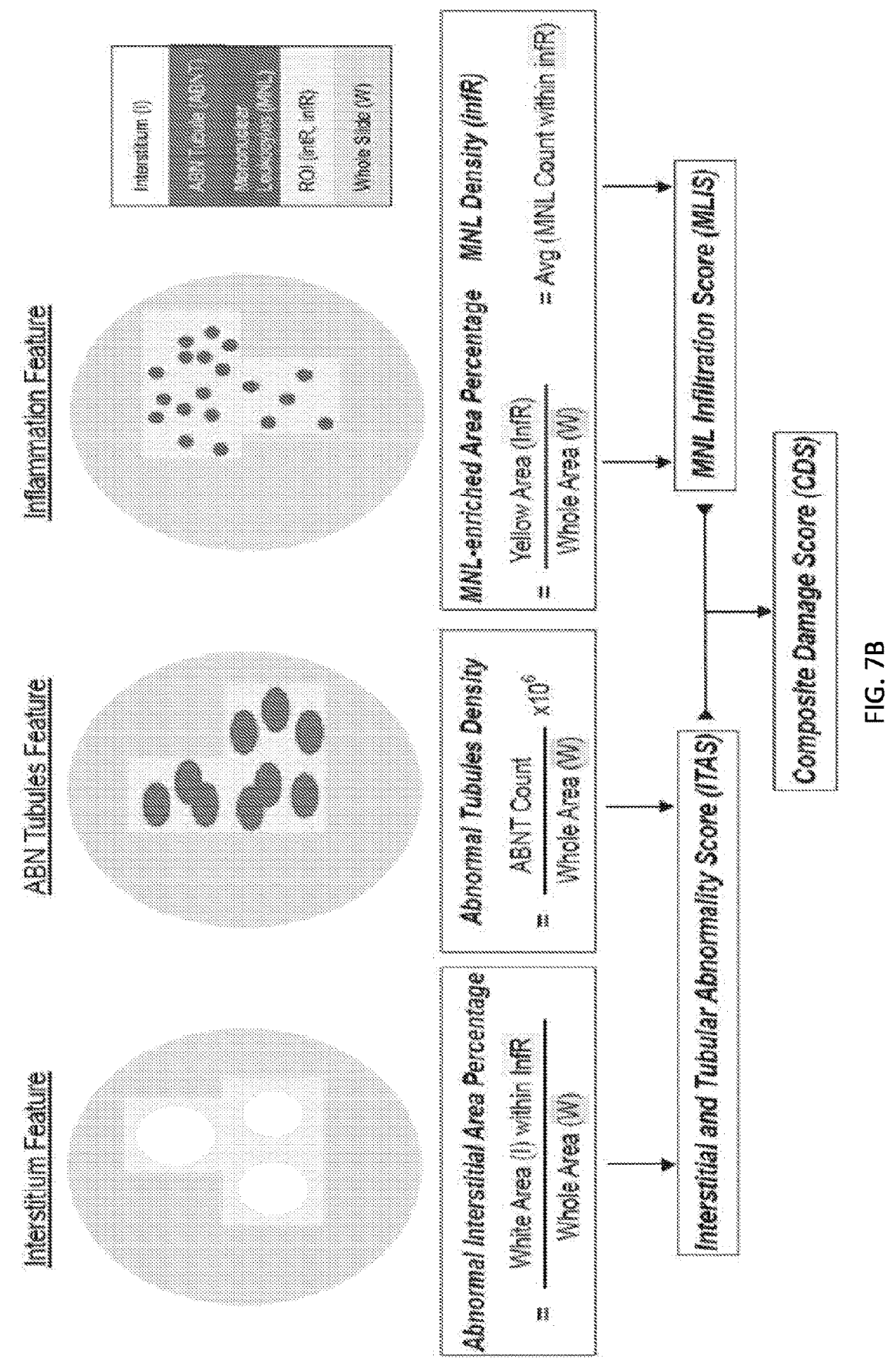

In stage II, the pretrained tissue compartment recognition models were applied to WSIs to extract a series of slide-wide digital features specifically capturing abnormalities within biopsies (FIGS. 7A-B, Supplementary Methods). For quantifying abnormalities in tubules and/or interstitium, a corresponding plurality of digital features for tissue compartment morphological classes, including individual feature scores and composite feature scores, were defined. These digital features included (i) abnormal interstitial area percentage, a proportion of total abnormal interstitium area over WSI; (ii) standardized abnormal tubule density; and (iii) Interstitial and Tubular Abnormality Score (ITAS), a composite score of (i) and (ii). To quantify inflammation in biopsies (e.g., MNL infiltration), a corresponding plurality of digital features for the inflammatory marker morphological class, including individual feature scores and composite feature scores, were defined. These digital features included (iv) MNL-enriched area percentage, a proportion of MNL infiltration area over WSI; (v) standardized MNL density; and (vi) MNL Infiltration Score, a composite score of (iv) and (v). Lastly, the method further included generating a composite class score by integrating both ITAS and MNL Infiltration Score to obtain a Composite Damage Score (CDS), which was defined as the estimation of overall graft damage.

Figures 4A, 4B:
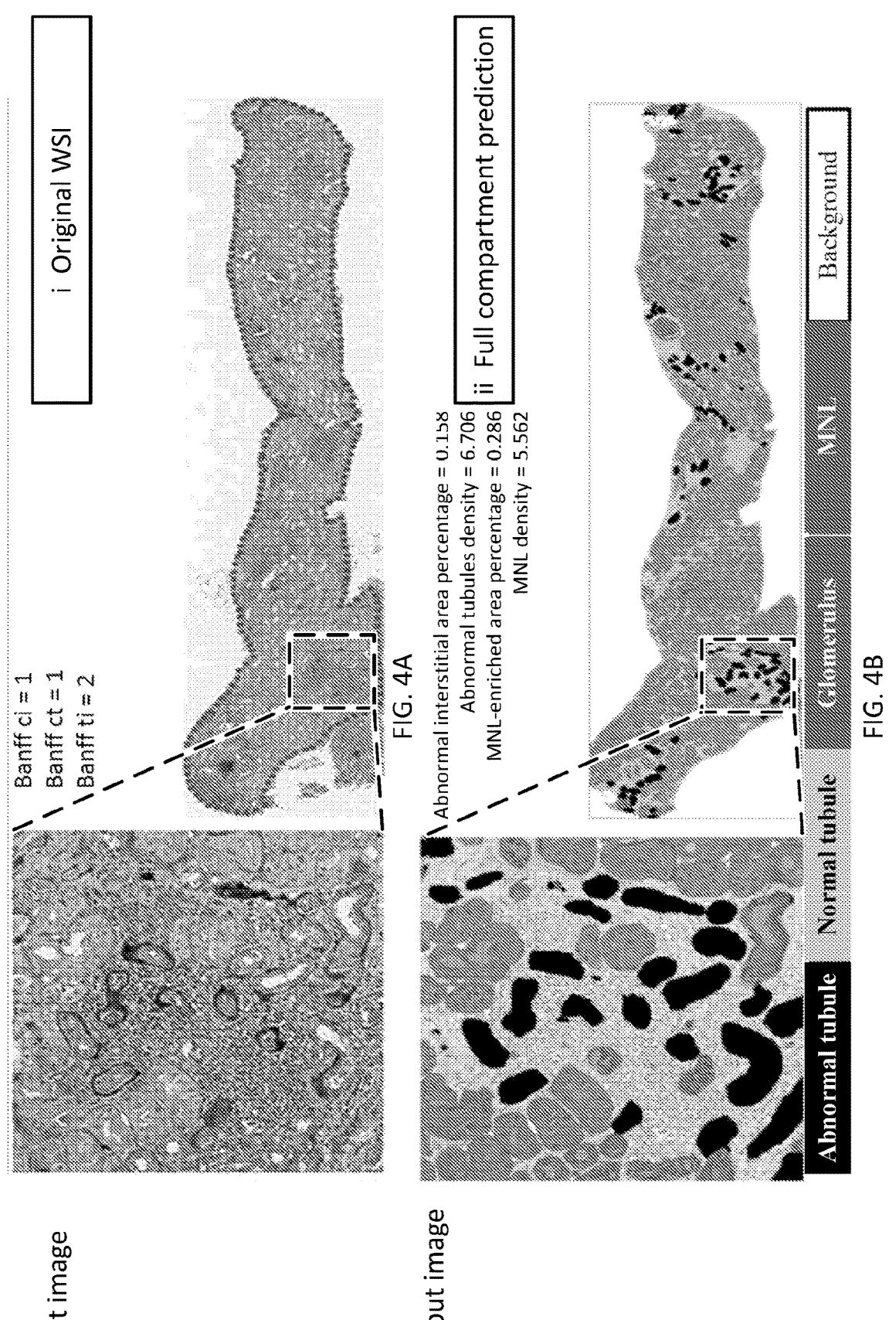

FIGS. 4A-D demonstrates an example application of the pipeline to an abnormal case: FIG. 4A: (i) original WSI, FIG. 4B: (ii) whole-slide prediction, and the masks highlighting FIG. 4C: (iii) abnormal interstitium or tubule regions or FIG. 4D: (iv) MNL infiltration regions that agreed with assessment by pathologists.

Digital Features were Correlated with Banff Scores

Figure 4E:
Figure 4E:
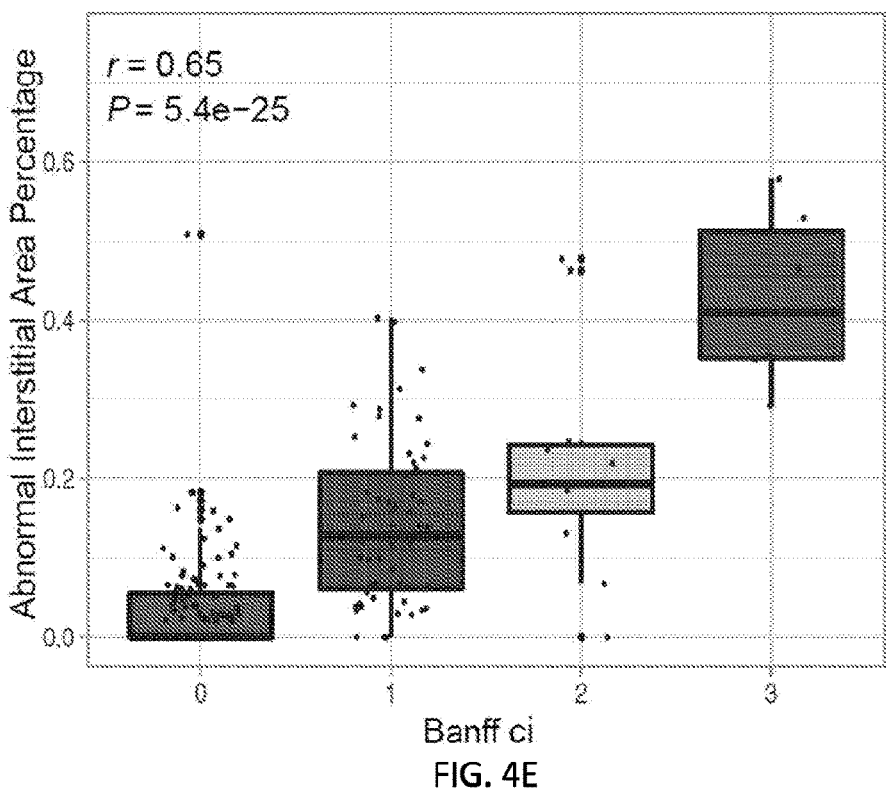
Figure 4F:
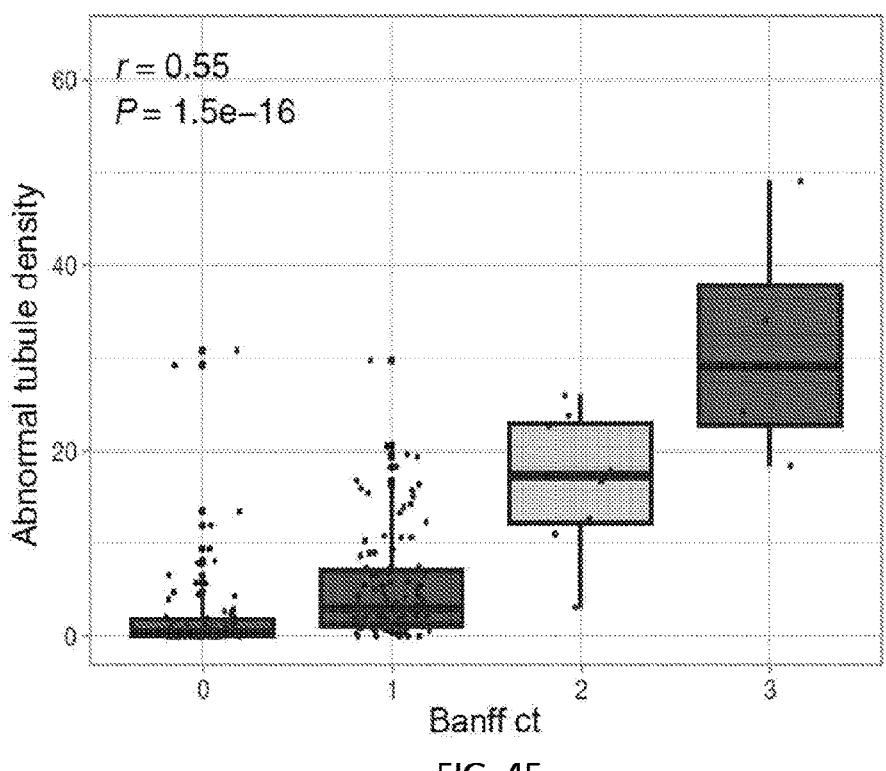
Figure 4G:
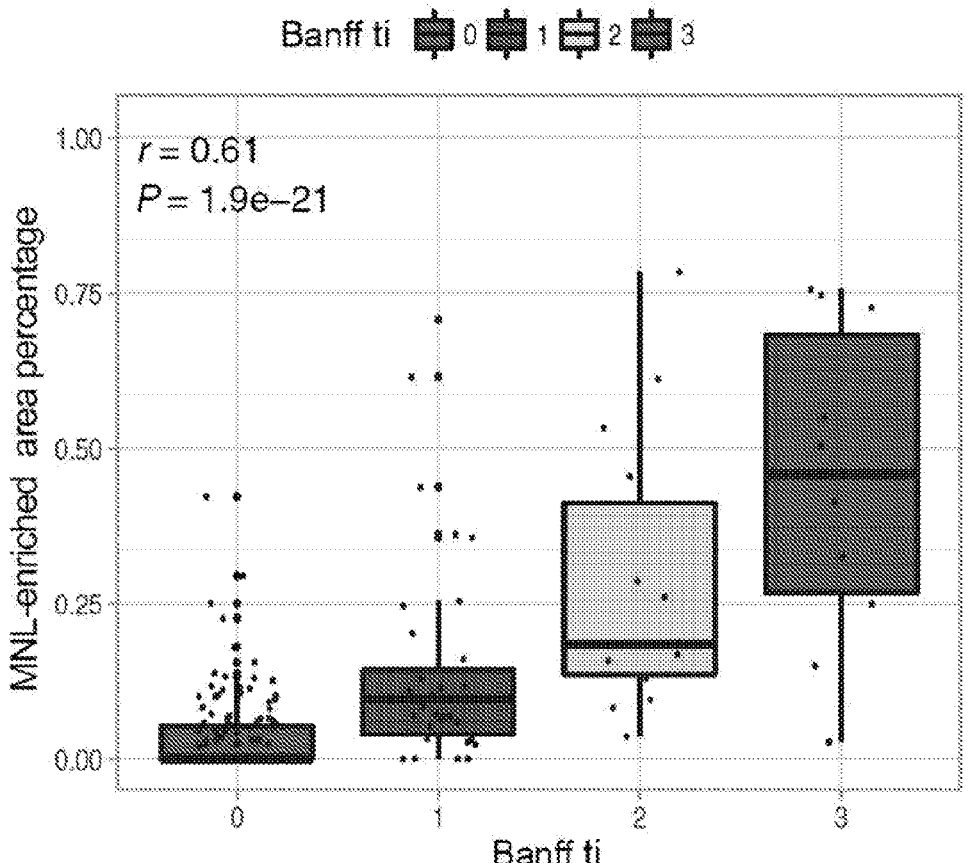
Figure 8A:
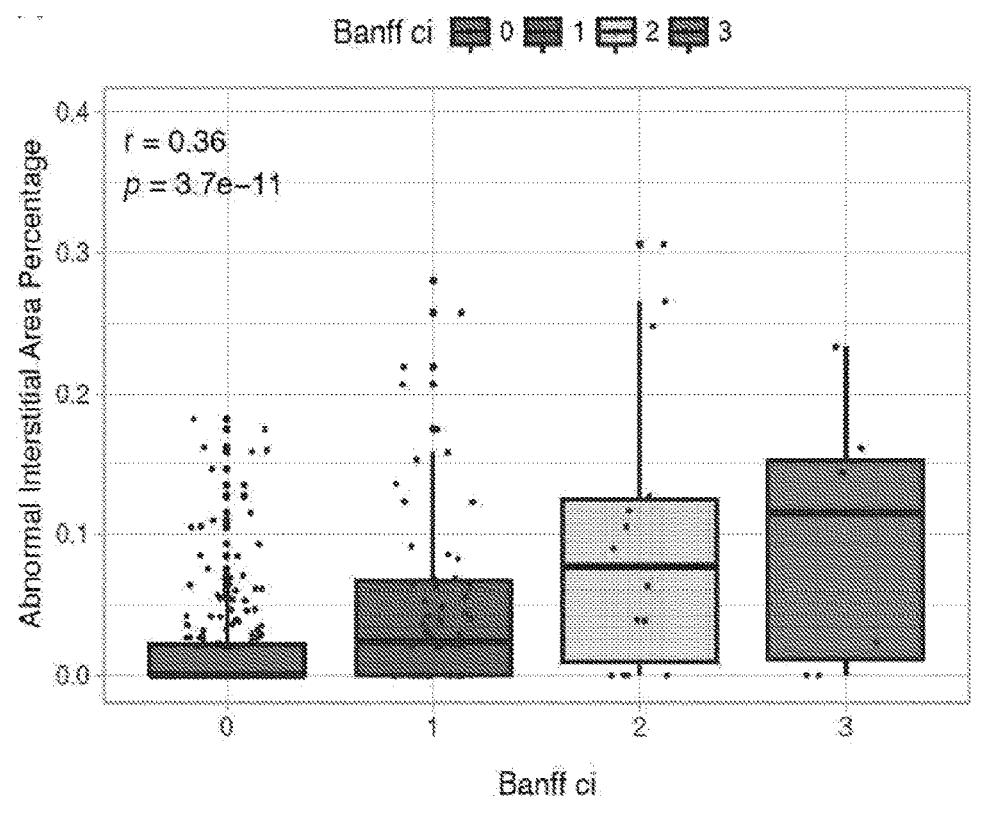
FIGS. 8A, 8B, and 8C collectively illustrate correlation of digital features with corresponding Banff scores, in accordance with an embodiment of the present disclosure.
Figure 8A:
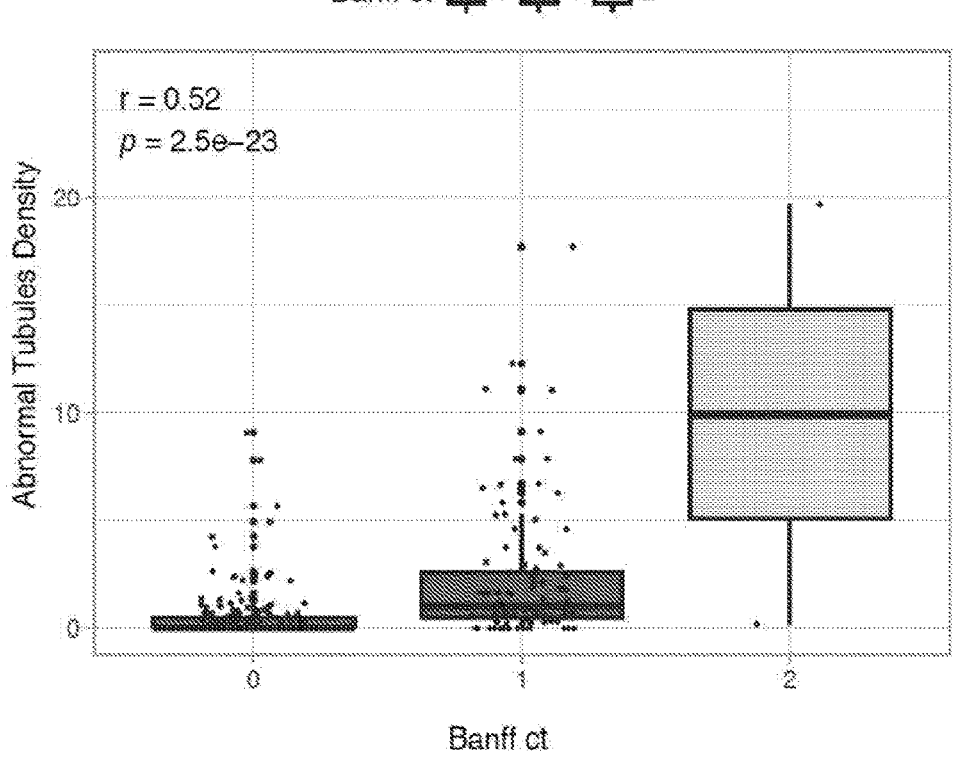
Figure 8B:
Figure 8B:
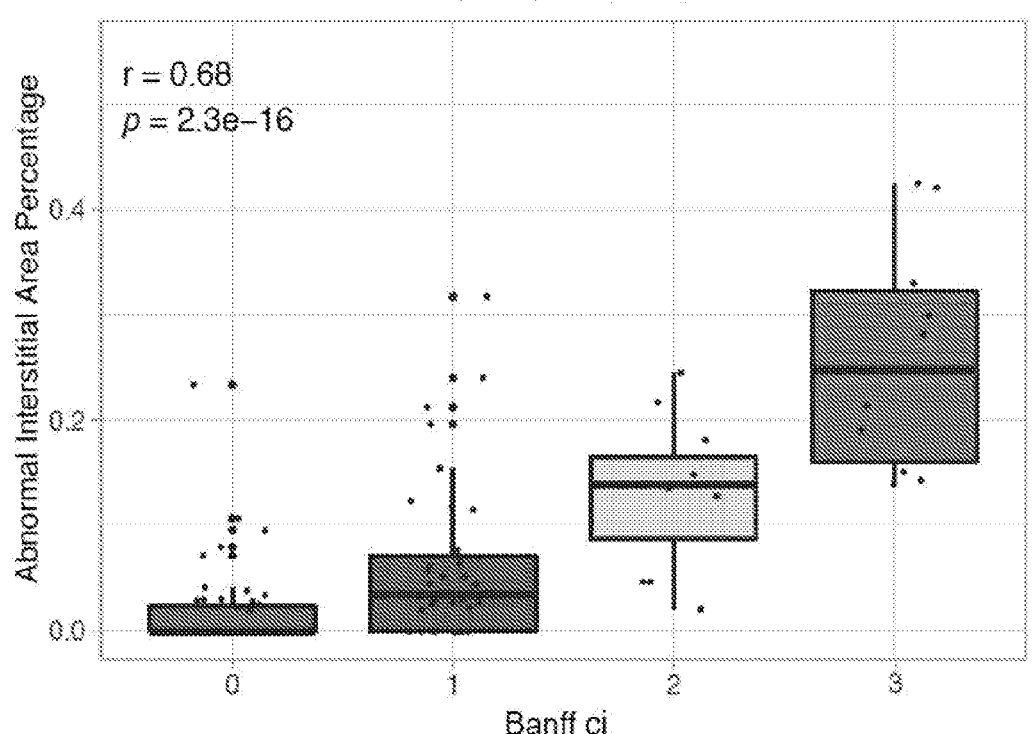
Figure 8B:
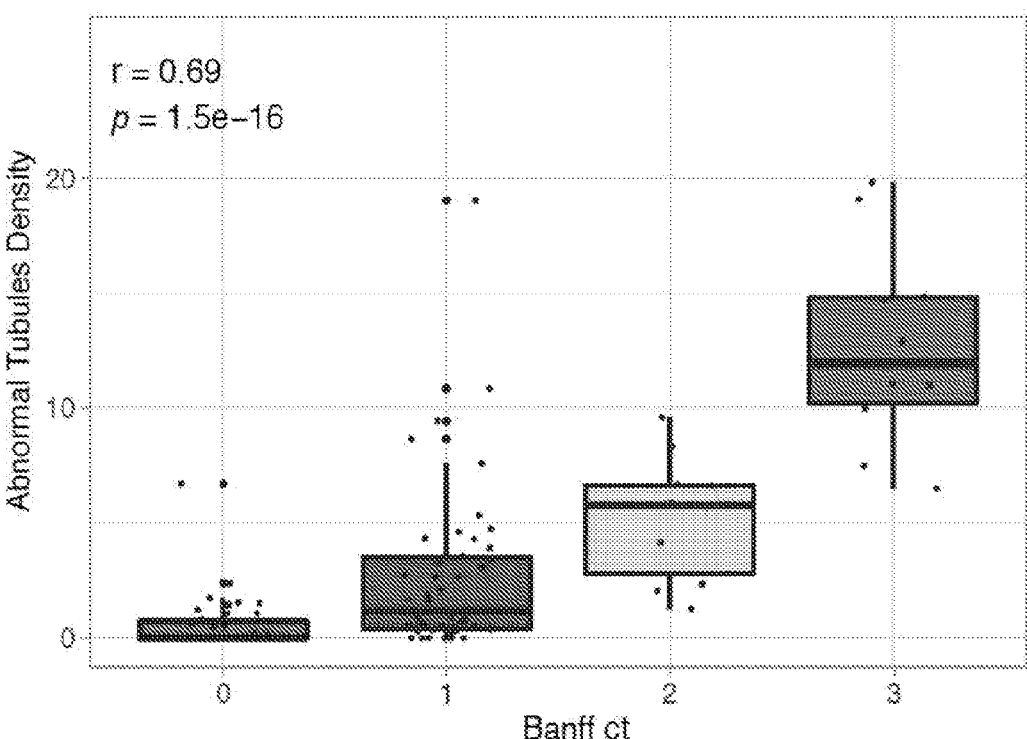
Figure 8C:
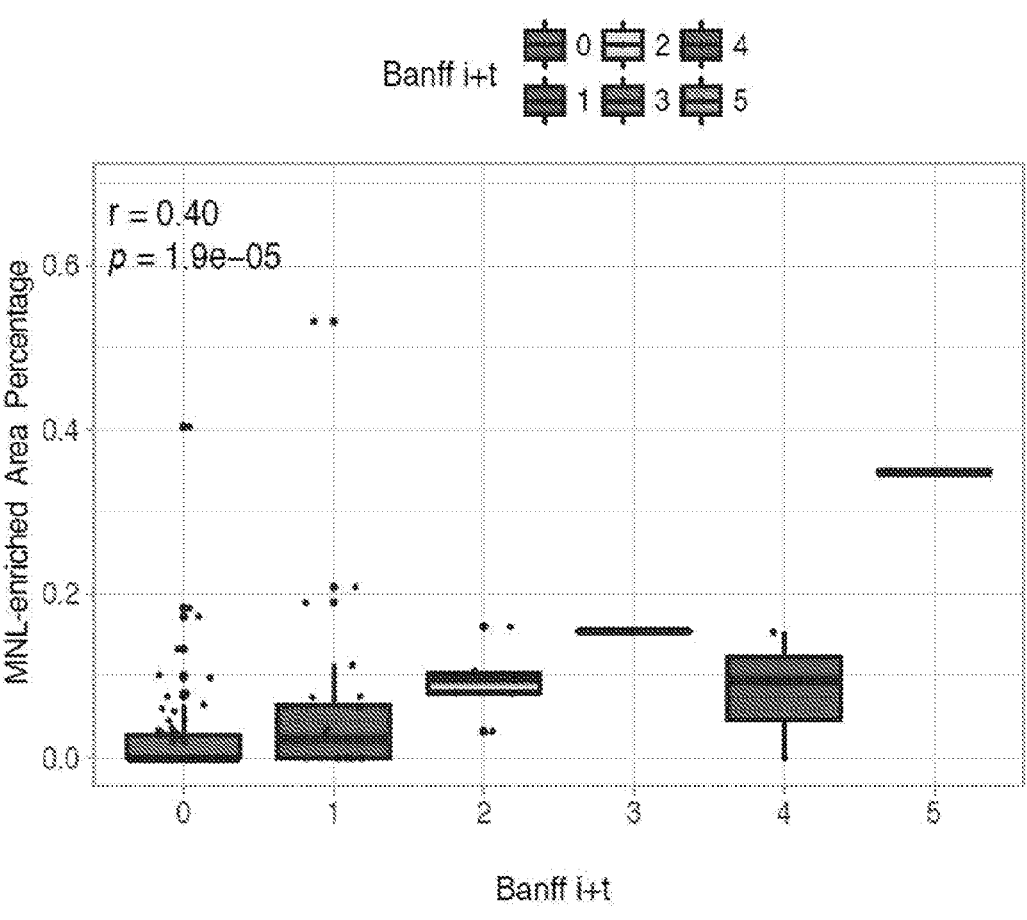

The Banff scores such as interstitial fibrosis (ci), tubular atrophy (ct), and total inflammation (ti) (graded by expert visual-assessment from different histologic stains) were similar in pathologic principle but different in quantification and technique to the PAS-based digital features (as illustrated in FIG. 7B). The relationship between these 2 methods was examined by performing a WSI investigation, extracting digital features in 789 WSIs from biopsies at baseline (n=478) and 12 months post-transplantation (n=311) in both the GoCAR and AUSCAD cohorts. The data indicated that digital features (abnormal interstitial area percentage, abnormal tubules density, and MNL-enriched area percentage) were significantly correlated with respective Banff scores in GoCAR biopsies at baseline (FIG. 8A) and 12 months (FIGS. 4E-G). Similarly, the digital scores were correlated with Banff scores in AUSCAD (12 months) where i+t was used because of unavailability of ti score (FIG. 8B-C). Notably, although MNL detection at the nuclei level yielded a lower accuracy compared to detection of glomeruli or tubules, the inflammatory marker digital features derived from MNLs were strongly correlated with ti scores in GoCAR (P=1.9e-21) and i+t in AUSCAD (P=1.9e-05) at the whole-slide level.

Figure 9A:
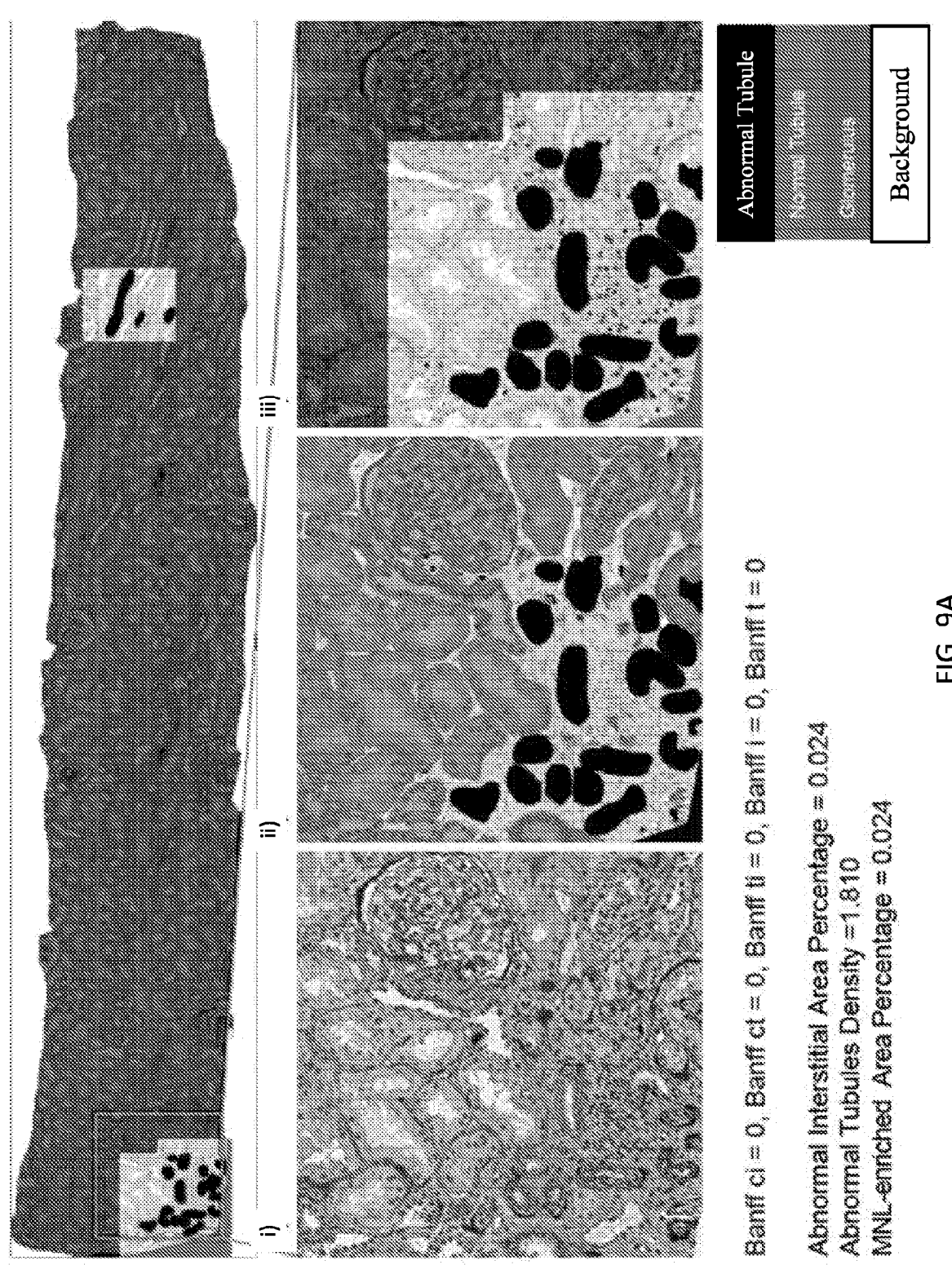
FIGS. 9A, 9B, and 9C collectively illustrate discrepancy between digital features and Banff scores, in accordance with an embodiment of the present disclosure.
Figure 9B:
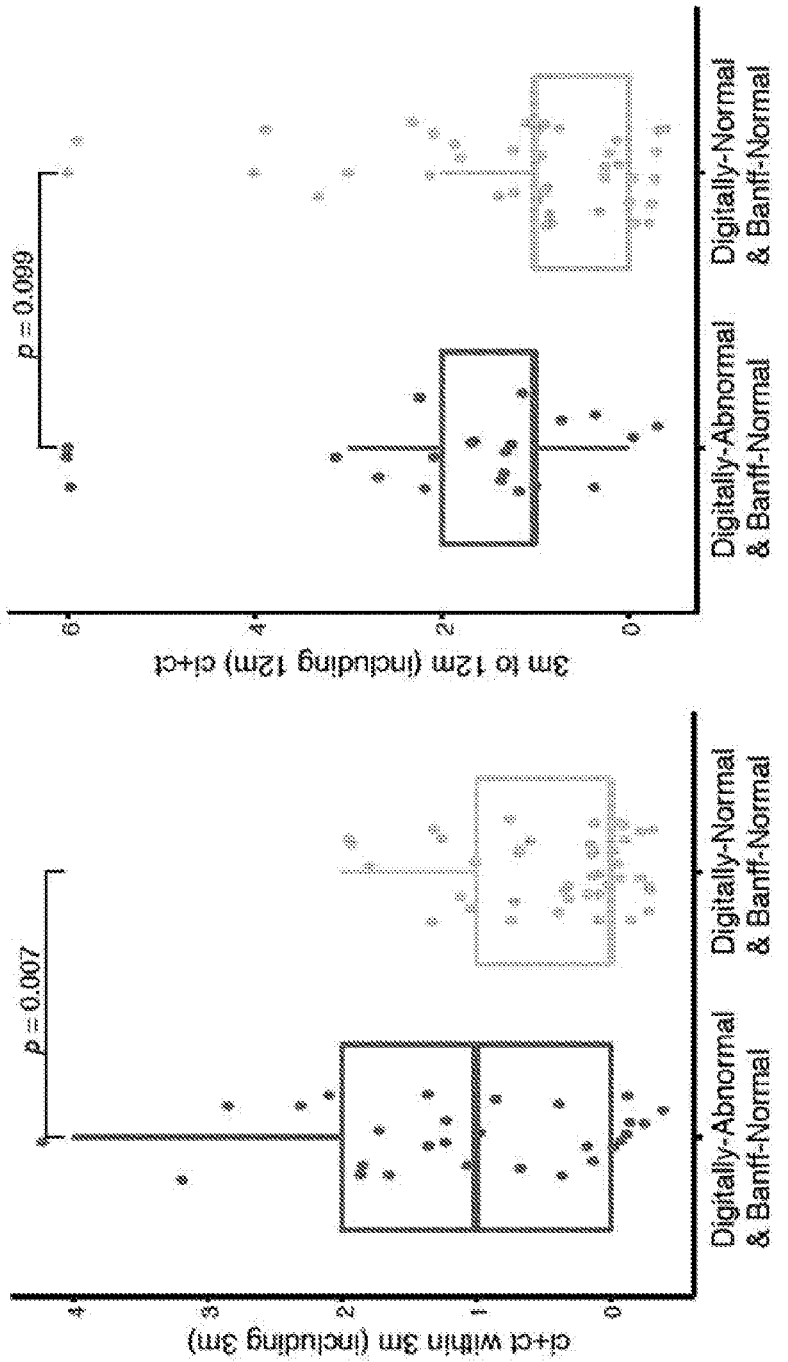
Figure 9C:
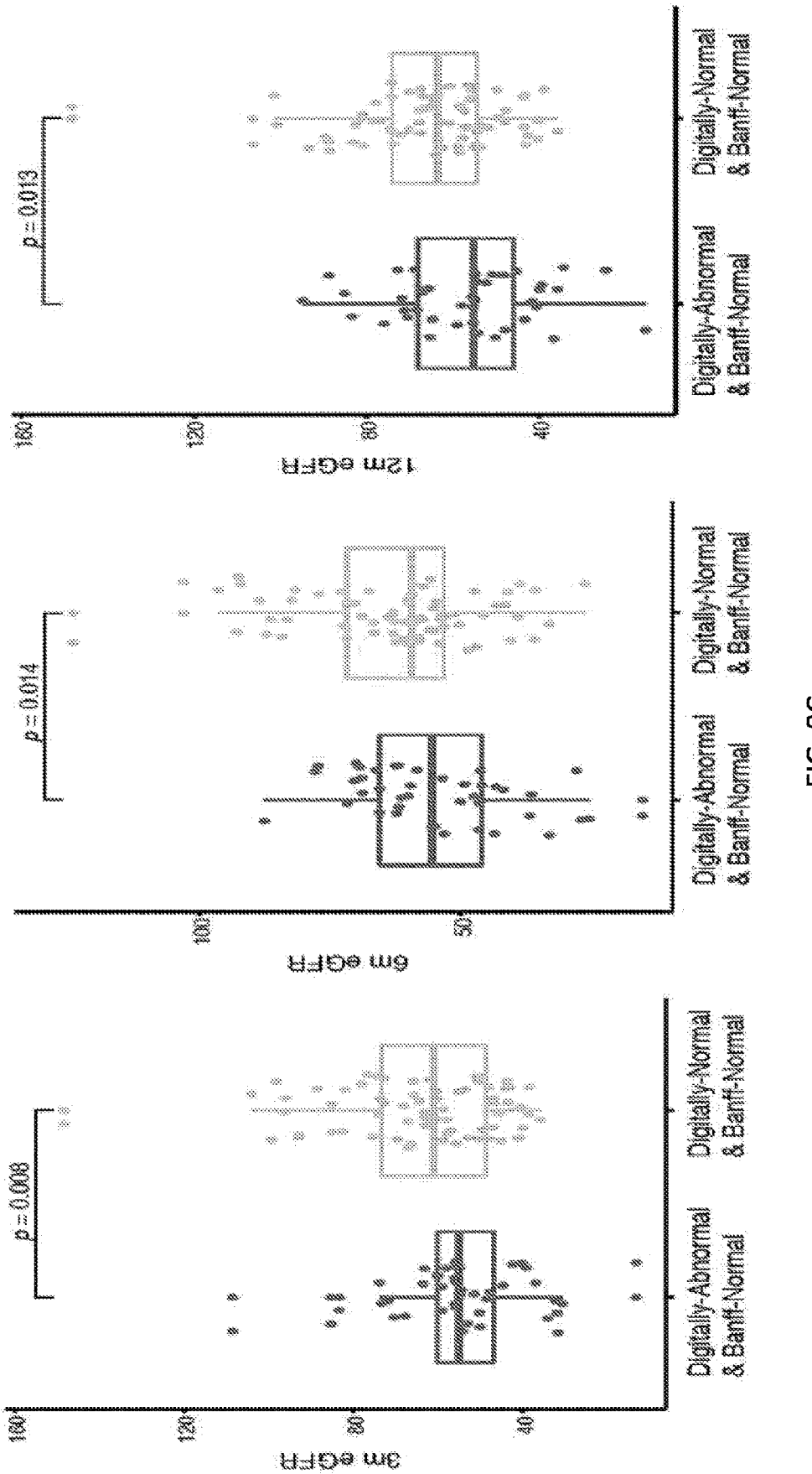

Although highly correlated, discrepancies were nevertheless identified between the 2 scoring systems such as the case demonstrated in FIG. 9A; here, Banff assessment reported all zeros, but digital features indicated abnormal scores (illustrated by small clusters of shrunken tubules and MNLs). All 137 cases classified as normal by Banff criteria (ci, ct, i, t, ti, g, cv=0) from baseline biopsies were then inspected, resulting in the identification of 50 abnormal and 87 normal cases based on digital features. No graft loss by 1 year was observed in these cases, but the baseline digitally abnormal group, compared with the all-normal group, had higher subsequent Banff ci+ct scores early post-transplantation, which were especially significant within the first 3 months (FIG. 9B). Moreover, the digitally abnormal group had a worse subsequent graft function as measured by eGFR within 12 months post-transplantation (FIG. 9C).

Taken together, the above-mentioned data indicate that digital features accurately reflected Banff scores and identified similar histologic lesions. Furthermore, it suggested that in cases of discrepancy, digital quantitative scores offer a more sensitive assessment of graft damage below the Banff threshold.

Figures 10A, 10B:
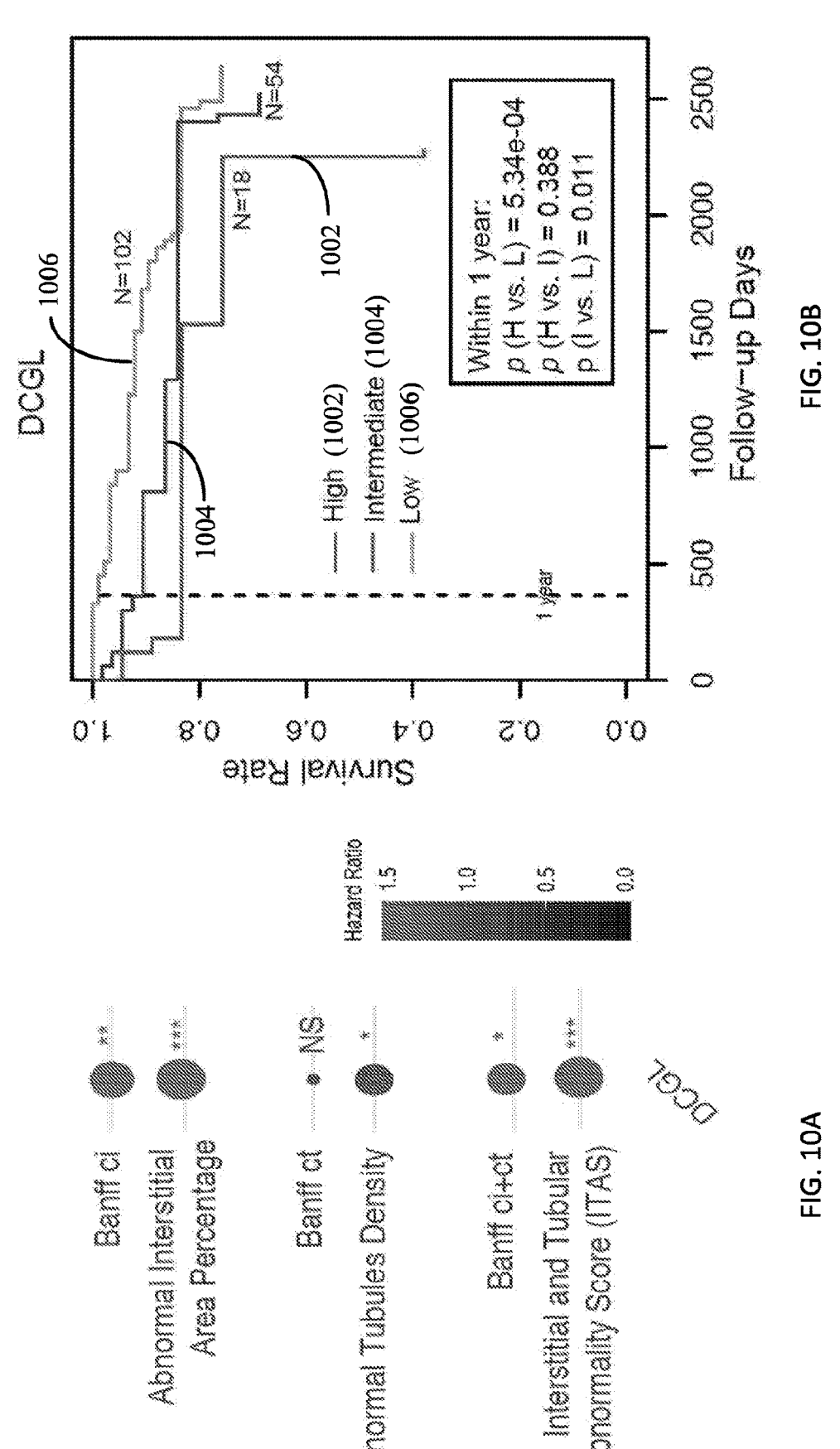
FIGS. 10A, 10B, 10C, and 10D collectively illustrate association of baseline digital features with post-transplant graft outcomes in the Genomics of Chronic Allograft Rejection (GoCAR) cohort, in accordance with an embodiment of the present disclosure.

Baseline Interstitial and Tubular Abnormality Score Predicted Early Grail Damage and 1-Year Graft Loss While the pathologic evaluation of baseline biopsies can be used reveal donor kidney quality, its utility in post-transplant prognosis has been debated (26). To explore a novel application for digital features in baseline biopsies, the association of individual or composite feature scores with post-transplant graft failure was examined and compared with the performance of Banff-based scores. Feature scores were also compared with the Kidney Donor Profile Index (KDPI), a composite demographic and clinical factor that is validated for deceased donors (27-29). In the GoCAR cohort (n=317) (FIG. 10A, Table 3), significant association of individual interstitial or tubular features and composite ITAS with death-censored graft loss (DCGL) was observed in univariate or multivariate Cox models. In the AUSCAD cohort (n=161) (Table 4), the association with graft survival was not confirmed in DCGL, which could be because there were fewer DCGL cases.

TABLE 3

Association of baseline Banff scores and digital features with graft
loss in the Genomics of Chronic Allograft Rejection (GoCAR) cohort.

| Scores | DCGL PH assumption p-value | DCGL p-value | DCGL p-value FDR adjusted | DCGL hazard ratio | DCGL lower CI | DCGL upper CI |
|---|---|---|---|---|---|---|
| a) Association of baseline Banff scores and digital features with death-censored graft loss (DCGL) | | | | | | |
| Banff ci | 0.16 | 5.0e−04 | 1.0e−03 | 1.81 | 1.29 | 2.52 |
| Abnormal Interstitial Area Percentage | 0.65 | 5.7e−05 | 3.4e−04 | 1.08 | 1.04 | 1.13 |
| Banff ct | 0.18 | 8.1e−01 | 8.1e−01 | — | — | — |
| Abnormal Tubules Density | 0.65 | 1.2e−02 | 1.8e−02 | 1.11 | 1.02 | 1.20 |
| Banff ci + ct | 0.17 | 2.8e−02 | 3.4e−02 | 1.38 | 1.04 | 1.84 |
| Interstitial and Tubular Abnormality Score (ITAS) | 0.93 | 1.5e−04 | 4.5e−04 | 3.25 | 1.77 | 5.97 |
| b) Association of baseline Banff scores and digital features with death-censored graft loss (DCGL) after adjusting for clinical confounders. | | | | | | |
| Banff ci | 0.14 | 3.2e−02 | 6.3e−02 | 1.54 | 1.04 | 2.27 |
| Abnormal Interstitial Area Percentage | 0.43 | 8.8e−03 | 3.7e−02 | 1.06 | 1.01 | 1.10 |
| Banff ct | 0.21 | 8.4e−01 | 8.4e−01 | — | — | — |
| Abnormal Tubules Density | 0.73 | 7.0e−02 | 1.1e−01 | — | — | — |
| Banff ci + ct | 0.20 | 2.3e−01 | 2.7e−01 | — | — | — |
| Interstitial and Tubular Abnormality Score (ITAS) | 0.69 | 1.2e−02 | 3.7e−02 | 2.28 | 1.20 | 4.35 |

* Cox p-values are calculated by Wald test from Cox proportional hazards regression. The proportional hazards assumptions are assessed through chi-square goodness of fit test between Schoenfeld residuals and time. Non-significant p-values confirm the assumption. Hazard ratios are not reported if PH assumptions are violated or cox p-values are not significant.

TABLE 4

Association of baseline Banff scores and digital features with graft
loss in the Australian Chronic Allograft Dysfunction (AUSCAD) cohort.

| Scores | DCGL PH Assumption p-value | DCGL p-value | DCGL p-value FDR adjusted | DCGL hazard ratio | DCGL lower CI | DCGL upper CI |
|---|---|---|---|---|---|---|
| a) Association of baseline digital features with death-censored graft loss (DCGL). | | | | | | |
| Abnormal Interstitial Area Percentage | 0.63 | 3.1e−01 | 7.0e−01 | — | — | — |
| Abnormal Tubules Density | 0.24 | 7.6e−01 | 1.0e+00 | — | — | — |
| Interstitial and Tubular Abnormality Score (ITAS) | 0.57 | 3.5e−01 | 7.0e−01 | — | — | — |
| b) Association of baseline digital features with death-censored graft loss (DCGL) after adjusting for clinical confounders. | | | | | | |
| Abnormal Interstitial Area Percentage | 0.63 | 1.8e−01 | 4.4e−01 | — | — | — |
| Abnormal Tubules Density | 0.22 | 4.6e−01 | 6.2e−01 | — | — | — |
| Interstitial and Tubular Abnormality Score (ITAS) | 0.57 | 2.2e−01 | 4.4e−01 | — | — | — |

* Cox p-values are calculated by Wald test from Cox proportional hazards regression. The proportional hazards assumptions are assessed through chi-square goodness of fit test between Schoenfeld residuals and time. Non-significant p-values confirm the assumption. Hazard ratios are not reported if PH assumptions are violated or cox p-values are not significant.

Figure 5A:
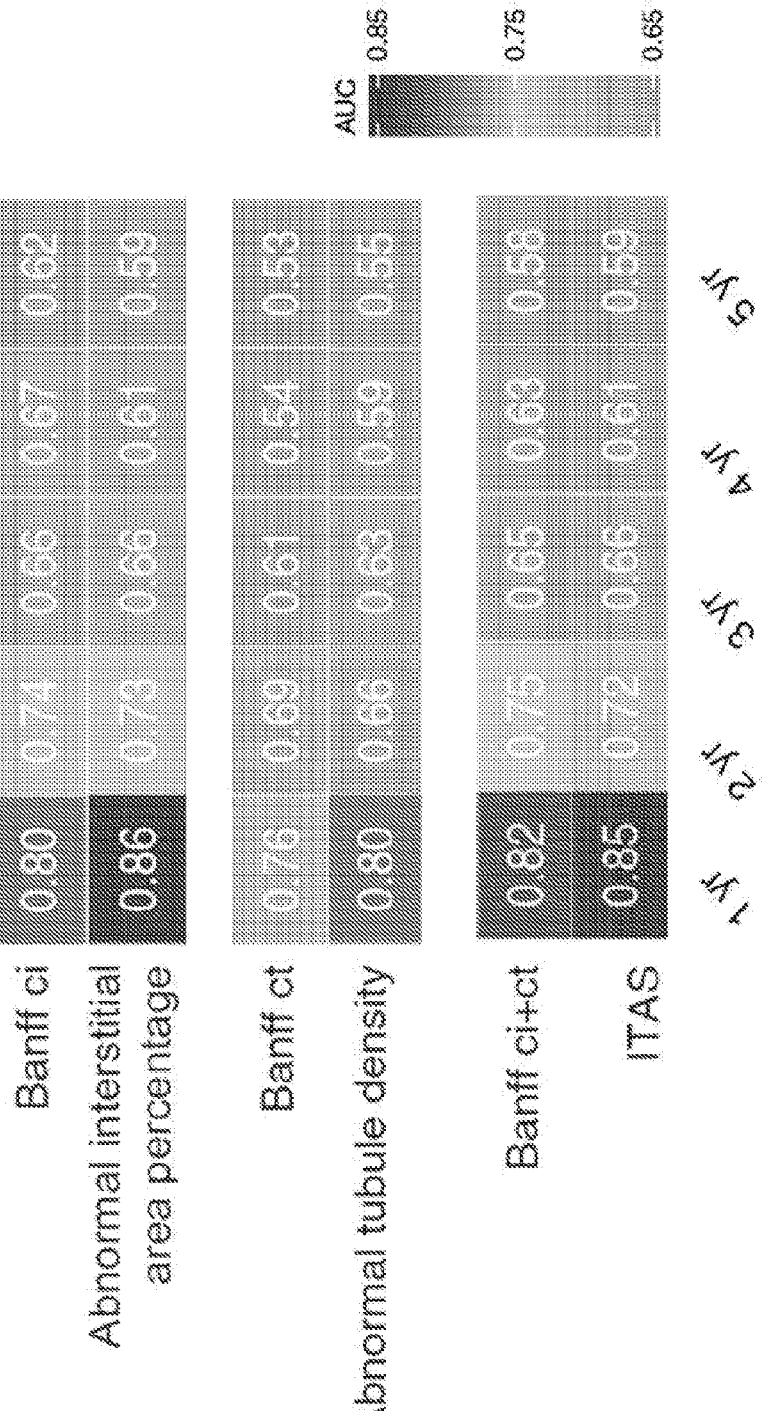
FIGS. 5A, 5B, 5C, and 5D collectively illustrate association of baseline digital features with post-transplant graft outcomes in the Genomics of Chronic Allograft Rejection (GoCAR) cohort, in accordance with an embodiment of the present disclosure.
Figure 5B:
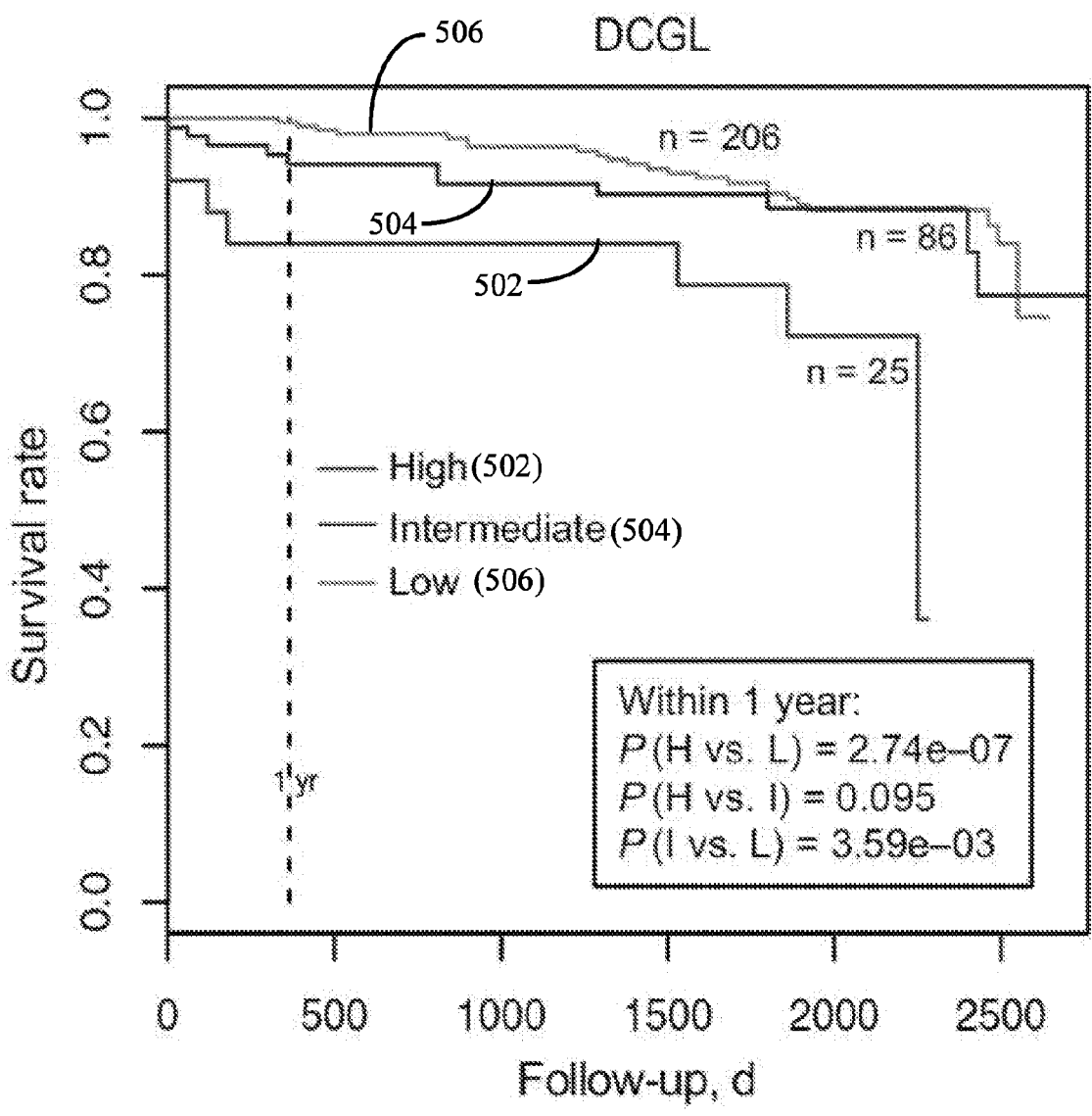

Time-dependent AUC estimation in GoCAR indicated that baseline individual or composite digital features outperformed individual Banff scores or ci+ct, respectively, in prediction of DCGL within 12 months (FIG. 5A). Next, baseline biopsies were stratified into 3 risk groups by composite feature ITAS, including high risk (ITAS>0.6), intermediate risk (0.1≤ITAS≤0.6), and low risk (ITAS<0.1) risk. The threshold for high risk using baseline ITAS was determined according to the percentile of baseline ci+ct>1 in the GoCAR cohort. A second threshold for low risk was added to identify healthy donor kidneys with zero or extremely low ITAS (<0.1). The high and intermediate ITAS risk groups exhibited significantly higher DCGL rates compared with those of the low ITAS risk group over the entire period of follow-up. These differences were most apparent in the first 12 months post-transplantation (P=2.8e-07 for high vs. low and P=3.6e-03 for intermediate vs. low) (FIG. 5B) and in the deceased-donor sub-cohort (P=5.3e-04 for high vs. low and P=0.011 for intermediate vs. low) (FIG.

Figures 10C, 10D:
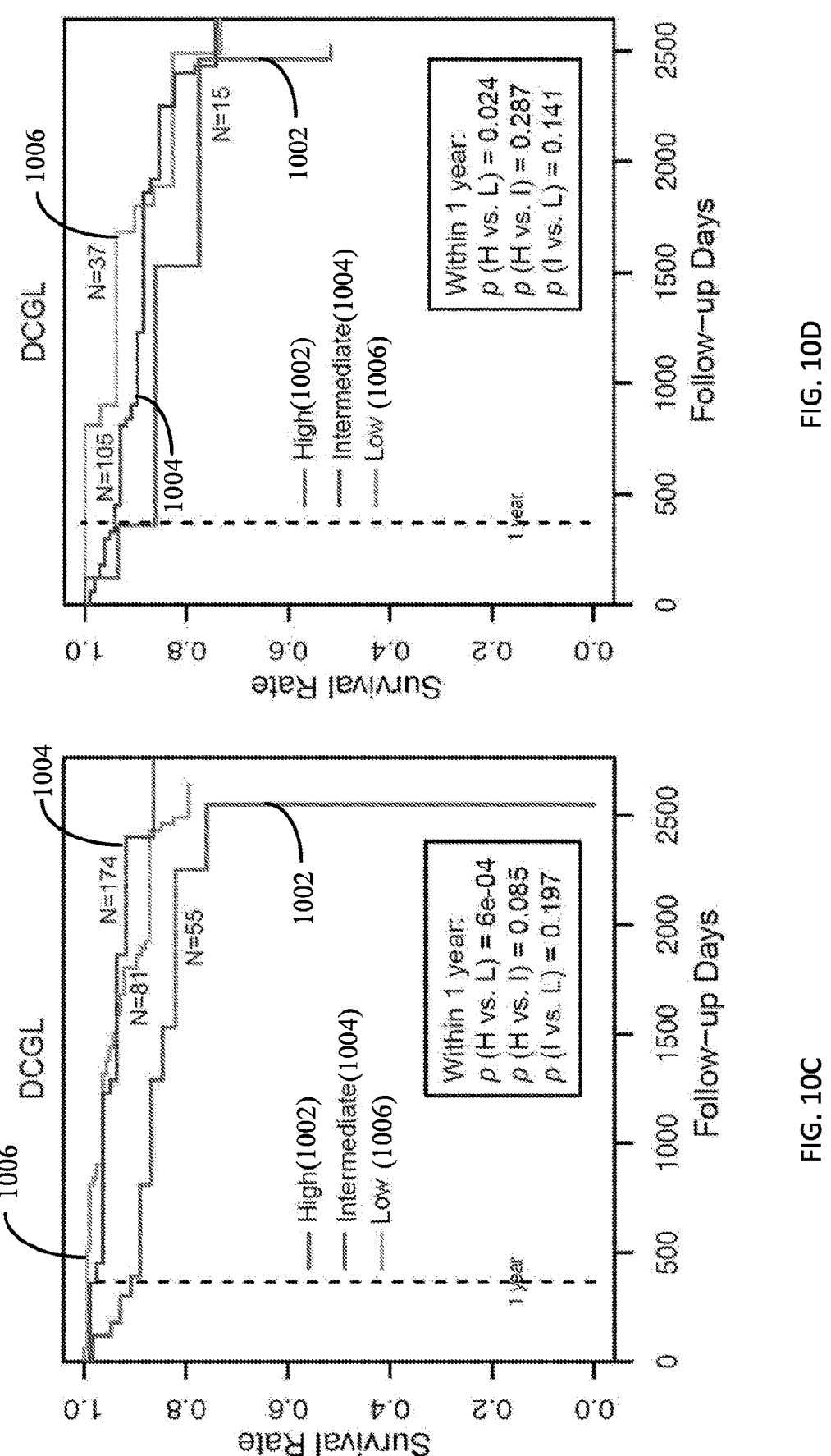
Figure 11A:
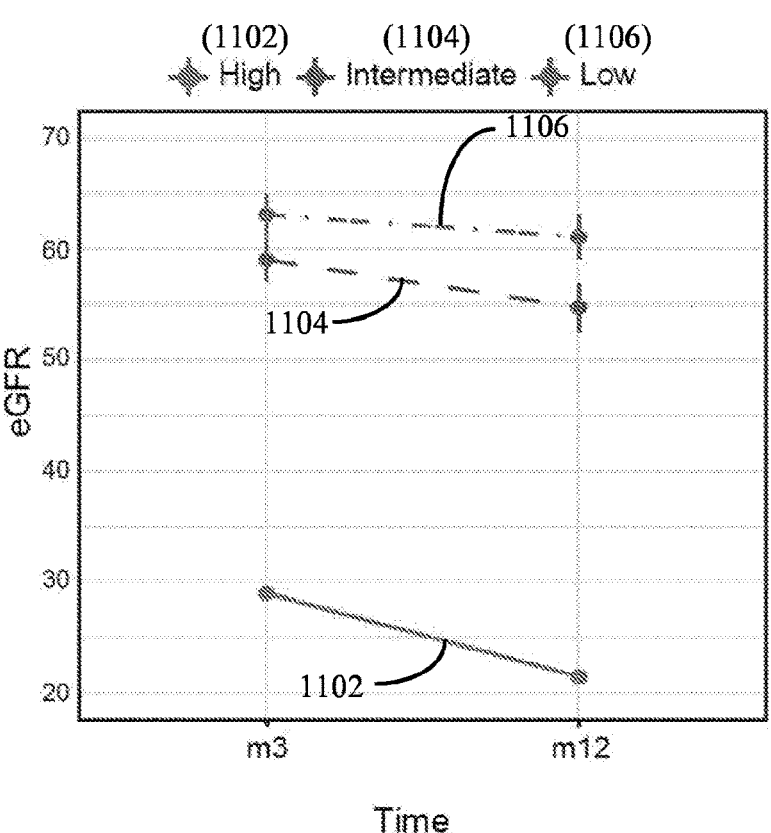
FIGS. 11A and 11B illustrate association of baseline digital features with post-transplant graft outcomes in the Australian Chronic Allograft Dysfunction (AUSCAD) cohort, in accordance with an embodiment of the present disclosure.
Figure 11B:
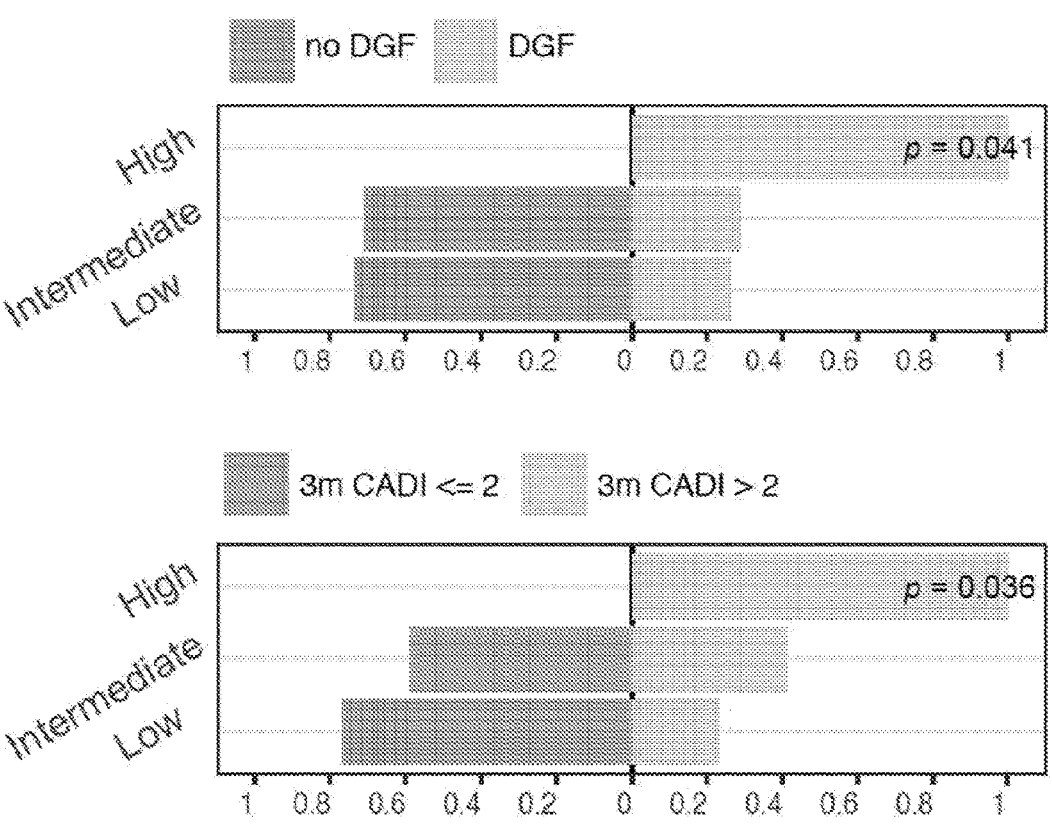

10B). ITAS was superior to ci=ct (P=6.0e-04 for high vs. low and P=0.197 for intermediate vs. low in the entire population) (FIG. 10C) and KDPI (P=0.024 for high vs. low and P=0.141 for intermediate vs. low, KDPI>85%, 20%<KDPI≤85%, KDPI≤20% in deceased-donor population) (FIG. 10D) for risk stratification of DCGL.

Figures 5C, 5D:
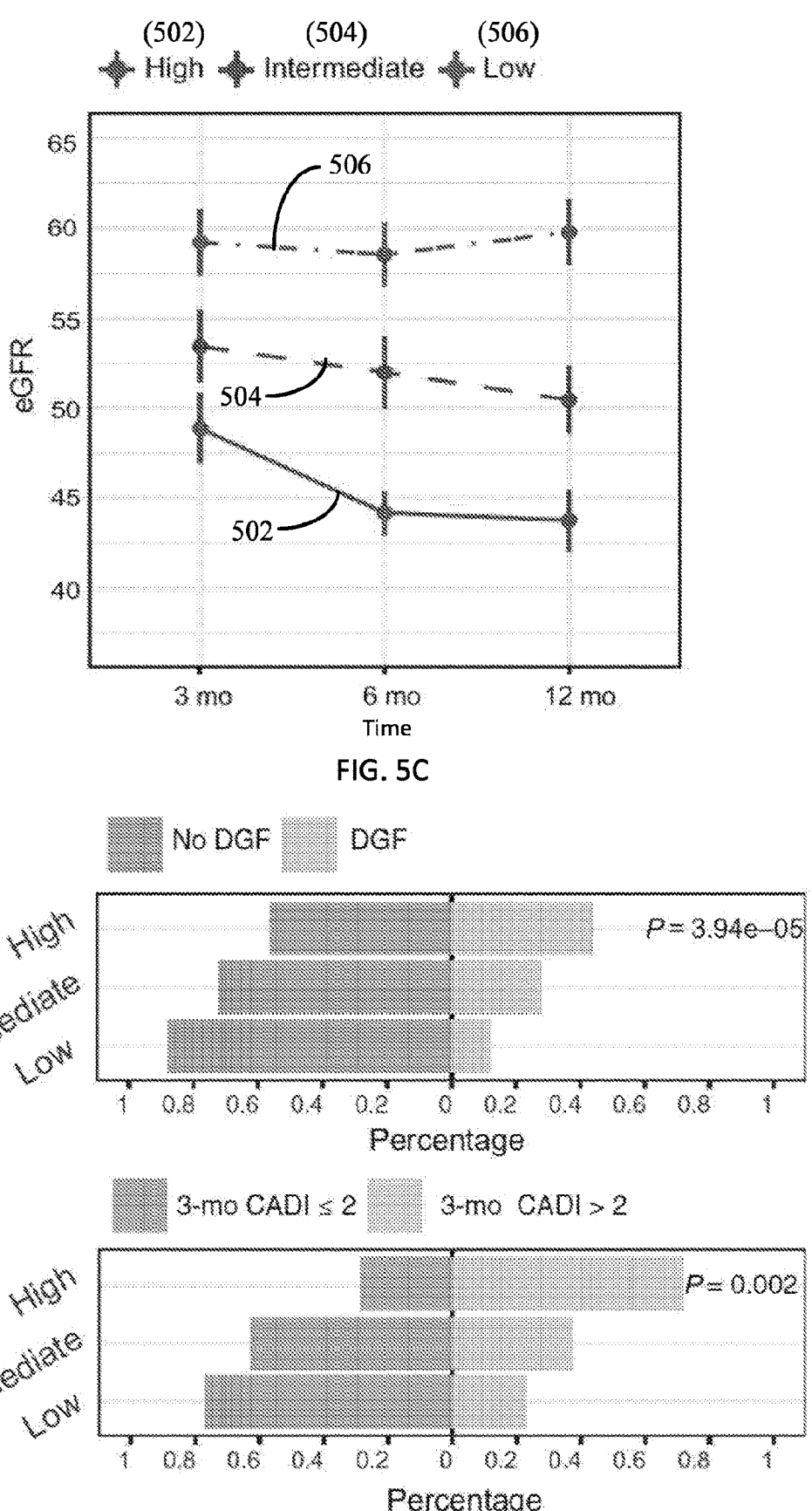

Of note, high and intermediate ITAS risk groups demonstrated a sustained decline in eGFR over the first 12 months post-transplantation (FIG. 5C), which is consistent with incrementally significant correlation of ITAS with post-transplant eGFR at 3 months (P=0.001), 6 months (P=7.6e-05), 12 months (P=1.5-05), and 24 months (P=0.015). A significantly higher incidence of delayed graft function (P=3.9e-05), and early (3 months post-transplantation) graft damage as measured by the Chronic Allograft Damage Index (CADI) score (30)>2 (P=0.002) were observed in high and intermediate ITAS risk groups (FIG. 5D). In the AUSCAD cohort (n=161), the associations of ITAS risk groups with other clinical outcomes were demonstrated in FIGS.

11A-B. To summarize, donor baseline ITAS is strongly associated with early graft function within 1 year post-transplantation, but the degree of association weakens afterward, implicating that recipient factors and post-transplant conditions come into play.

Figure 12:
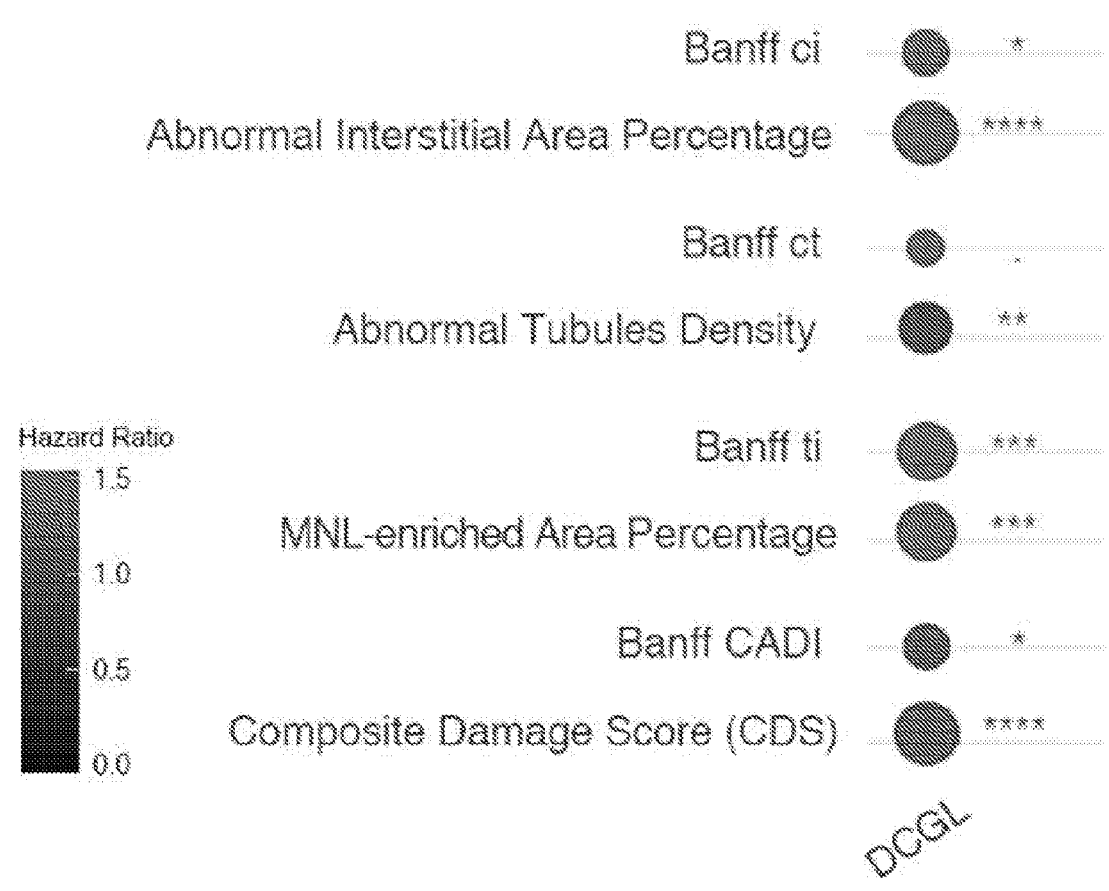
FIG. 12 illustrates association of 12-month post-transplant digital features with post-transplant graft outcomes in the Genomics of Chronic Allograft Rejection (GoCAR) cohort, in accordance with an embodiment of the present disclosure. A dot heatmap of association of Banff scores and digital features with post-transplant death-censored graft loss (DCGL) in 12-month post-transplant biopsy slides (n=200) is shown. The size of dot and number of asterisks indicate significance level (p-value) of association by Cox proportional hazards regression (NS: p≥0.1; .: 0.05≤ p<0.1; *:0.005≤p<0.05; : 5e-04≤p<0.005; *: 5e-05≤p<5e-04; ****:p<5e-05). Shading darkness of dots indicate hazard ratio.

Twelve-Month Post-Transplant Composite Damage Score Predicted Long-Term Graft Loss Because the data showed that composite baseline digital score predicts early but not long-term DCGL, longer term subsequent graft survival was examined using 12-month post-transplant biopsy slides in both cohorts. In GoCAR (n=200) (FIG. 12, Table 5), digital interstitial and tubular features, which are superior to corresponding Banff ci and ct scores, were significantly associated with long-term DCGL with or without adjustment for clinical confounders (living or deceased donor, CIT, baseline donor-specific antibodies, human leukocyte antigen mismatch, and induction type), while the MNL feature was comparable to the Banff ti score in association with DCGL. The associations of 12-month digital features with long-term survival were validated in the AUSCAD cohort (n=111) (Table 6).

TABLE 5

Association of 12-month post-transplant Banff scores and digital features with graft loss in the Genomics of Chronic Allograft Rejection (GoCAR) cohort.

| Scores | DCGL PH Assumption p-value | DCGL p-value | DCGL p-value FDR adjusted | DCGL hazard ratio | DCGL lower CI | DCGL upper CI |
|---|---|---|---|---|---|---|
| a) Association of 12-month Banff scores and digital features with death-censored graft loss (DCGL). | | | | | | |
| Banff ci | 0.37 | 1.6e−02 | 2.1e−02 | 1.74 | 1.11 | 2.73 |
| Abnormal Interstitial Area Percentage | 0.31 | 2.1e−05 | 8.5e−05 | 1.05 | 1.03 | 1.08 |
| Banff ct | 0.48 | 9.6e−02 | 9.6e−02 | — | — | — |
| Abnormal Tubules Density | 0.60 | 1.5e−03 | 2.4e−03 | 1.06 | 1.02 | 1.09 |
| Banff ti | 0.19 | 2.2e−04 | 4.4e−04 | 2.10 | 1.42 | 3.10 |
| MNL-enriched Area Percentage | 0.80 | 1.6e−04 | 4.3e−04 | 1.03 | 1.02 | 1.05 |
| Banff CADI | 0.81 | 2.2e−02 | 2.5e−02 | 1.22 | 1.03 | 1.45 |
| Composite Damage Score (CDS) | 0.90 | 1.8e−05 | 8.5e−05 | 1.30 | 1.15 | 1.47 |
| b) Association of 12-month Banff scores and digital features with death-censored graft loss (DCGL) after adjusting for clinical confounders. | | | | | | |
| Banff ci | 0.17 | 7.7e−02 | 1.0e−01 | — | — | — |
| Abnormal Interstitial Area Percentage | 0.17 | 4.8e−04 | 3.8e−03 | 1.05 | 1.02 | 1.07 |
| Banff ct | 1.00 | 4.0e−01 | 4.0e−01 | — | — | — |
| Abnormal Tubules Density | 0.26 | 1.6e−02 | 2.5e−02 | 1.05 | 1.01 | 1.09 |
| Banff ti | 0.07 | 1.2e−02 | 2.3e−02 | 1.76 | 1.13 | 2.72 |
| MNL-enriched Area Percentage | 0.75 | 7.6e−03 | 2.0e−02 | 1.03 | 1.01 | 1.04 |
| Banff CADI | 0.60 | 2.5e−01 | 2.8e−01 | — | — | — |
| Composite Damage Score (CDS) | 0.64 | 1.5e−03 | 6.1e−03 | 1.25 | 1.09 | 1.43 |

* Cox p-values are calculated by Wald test from Cox proportional hazards regression. The proportional hazards assumptions are assessed through chi-square goodness of fit test between Schoenfeld residuals and time. Non-significant p-values confirm the assumption. Hazard ratios are not reported if PH assumptions are violated or cox p-values are not significant.

TABLE 6

Association of 12-month post-transplant Banff scores and digital features with graft loss in the Australian Chronic Allograft Dysfunction (AUSCAD) cohort.

| Scores | DCGL PH Assumption p-value | DCGL p-value | DCGL p-value FDR adjusted | DCGL hazard ratio | DCGL lower CI | DCGL upper CI |
|---|---|---|---|---|---|---|
| a) Association of 12-month Banff scores and digital features with death-censored graft loss (DCGL). | | | | | | |
| Banff ci | 0.04 | — | — | — | — | — |
| Abnormal Interstitial Area Percentage | 0.46 | 4.9e− 03 | 1.2e−02 | 1.08 | 1.02 | 1.14 |
| Banff ct | 0.03 | — | — | — | — | — |
| Abnormal Tubules Density | 0.58 | 4.2e−02 | 5.6e−02 | 1.10 | 1.00 | 1.20 |
| Banff i + t | 0.79 | 2.2e−03 | 1.2e−02 | 6.32 | 1.94 | 20.60 |
| MNL-enriched Area Percentage | 0.78 | 8.8e−03 | 1.4e−02 | 1.08 | 1.02 | 1.14 |
| Banff CADI | 0.03 | — | — | — | — | — |
| Composite Damage Score (CDS) | 0.75 | 6.1e−03 | 1.2e−02 | 1.71 | 1.16 | 2.50 |
| b) Association of 12-month Banff scores and digital features with death-censored graft loss (DCGL) after adjusting for clinical confounders. | | | | | | |
| Banff ci | 0.03 | — | — | — | — | — |
| Abnormal Interstitial Area Percentage | 0.36 | 1.1e−02 | 4.2e−02 | 1.08 | 1.02 | 1.14 |
| Banff ct | 0.03 | — | — | — | — | — |
| Abnormal Tubules Density | 0.36 | 7.5e−02 | 8.2e−02 | — | — | — |
| Banff i + t | 0.74 | 3.0e−02 | 5.1e−02 | 14.67 | 1.29 | 166.94 |
| MNL-enriched Area Percentage | 0.78 | 3.2e−02 | 5.1e−02 | 1.07 | 1.01 | 1.15 |

TABLE 6-continued

Association of 12-month post-transplant Banff scores and digital features with
graft loss in the Australian Chronic Allograft Dysfunction (AUSCAD) cohort.

| Scores | DCGL PH Assumption p-value | DCGL p-value | DCGL p-value FDR adjusted | DCGL hazard ratio | DCGL lower CI | DCGL upper CI |
|---|---|---|---|---|---|---|
| Banff CADI | 0.04 | — | — | — | — | — |
| Composite Damage Score (CDS) | 0.71 | 2.2e−02 | 5.1e−02 | 1.69 | 1.08 | 2.63 |

*Cox p-values are calculated by Wald test from Cox proportional hazards regression. The proportional hazards assumptions are assessed through chi-square goodness of fit test between Schoenfeld residuals and time. Non-significant p-values confirm the assumption. Hazard ratios are not reported if PH assumptions are violated or cox p-values are not significant.

Figure 6A:
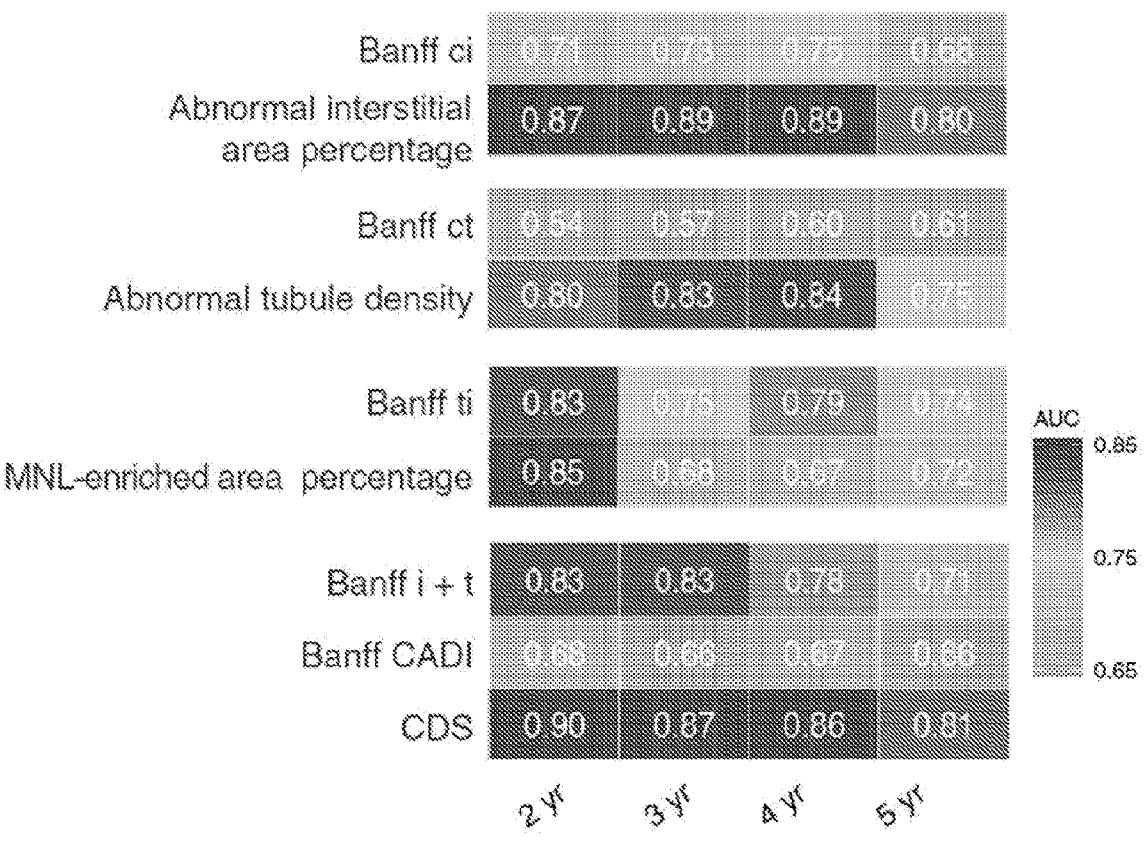
FIGS. 6A, 6B, 6C, and 6D collectively illustrate association of 12-month post-transplant digital features with post-transplant graft outcomes in the Genomics of Chronic Allograft Rejection (GoCAR) cohort, in accordance with an embodiment of the present disclosure.
Figure 6B:
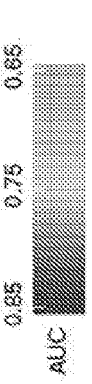
Figure 6C:
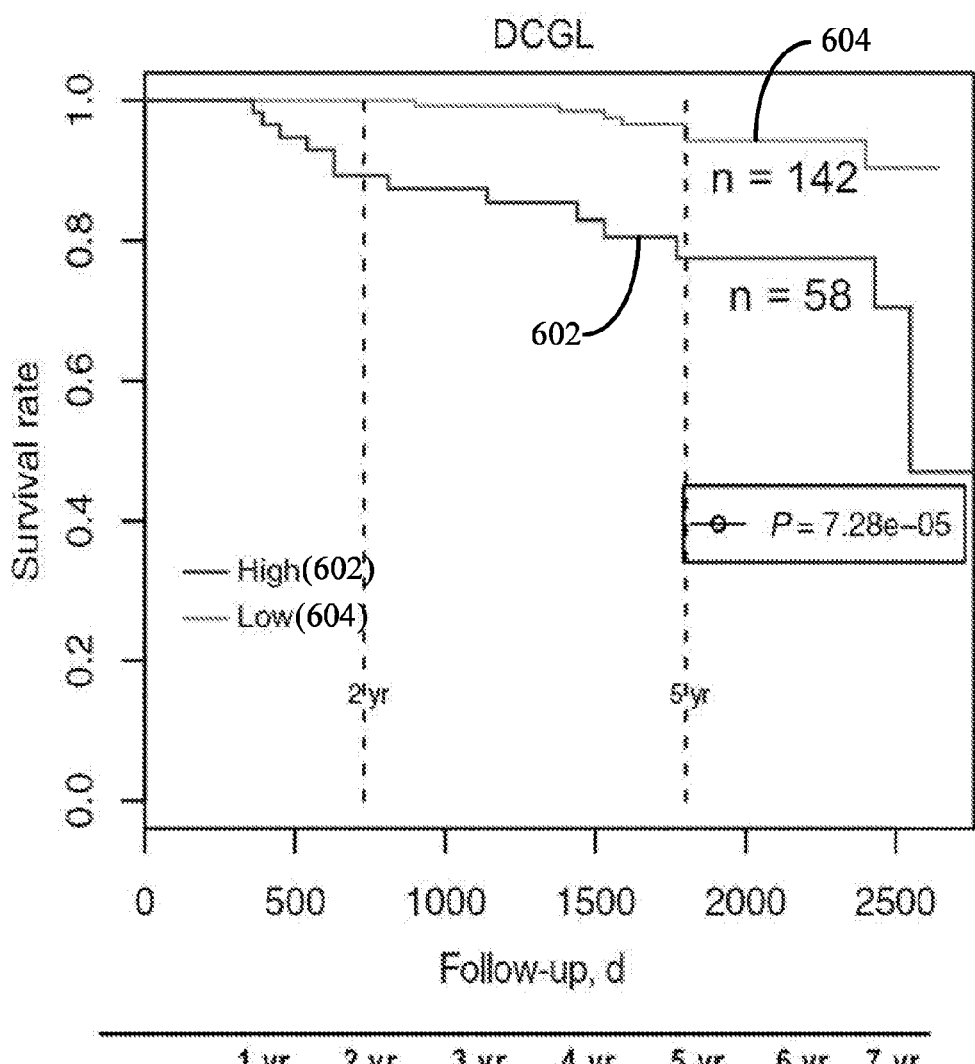
Figure 6D:
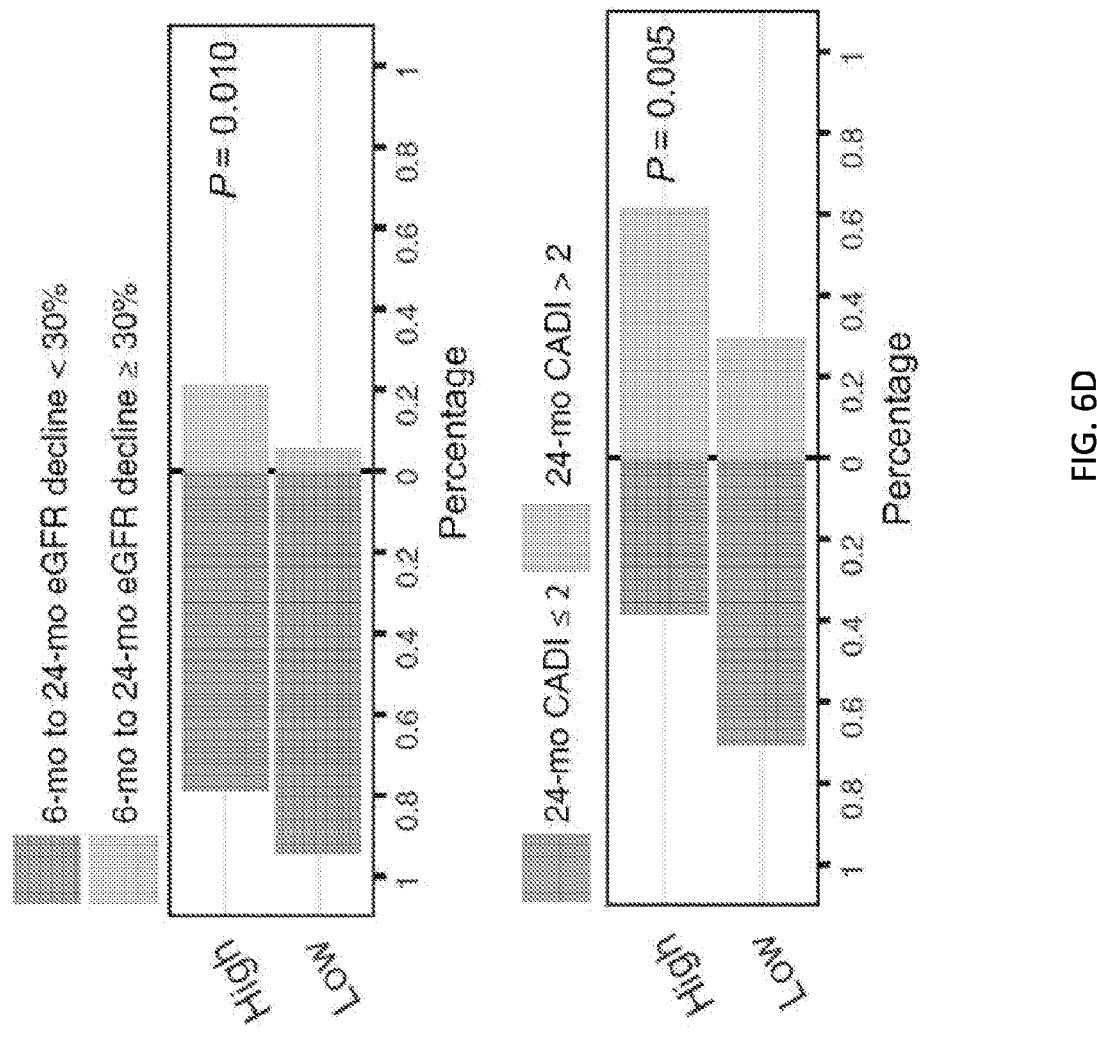
Figure 13A:
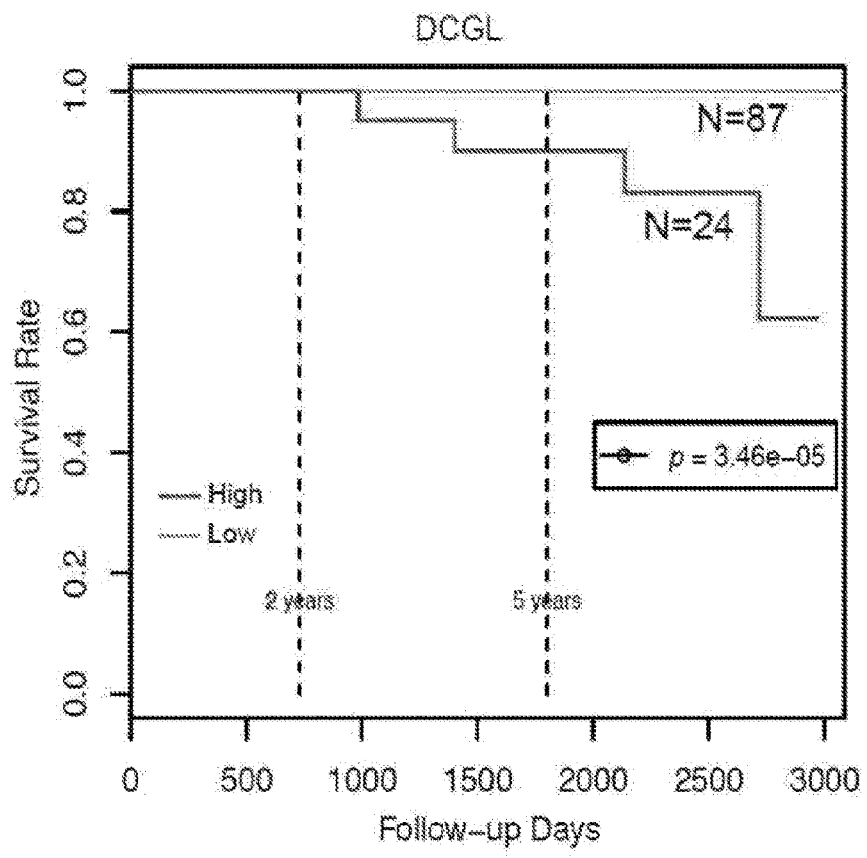
FIGS. 13A and 13B collectively illustrate association of 12-month post-transplant digital features with post-transplant graft outcomes in the Australian Chronic Allograft Dysfunction (AUSCAD) cohort, in accordance with an embodiment of the present disclosure.
Figure 13B:
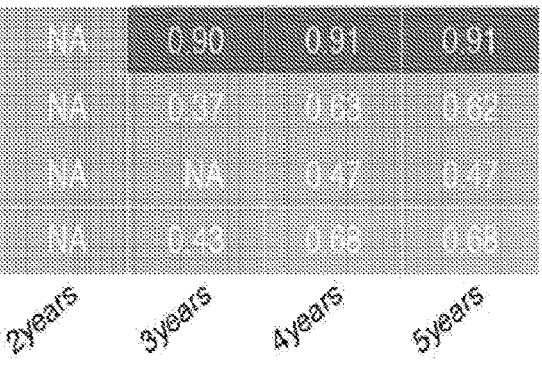
Figure 13B:
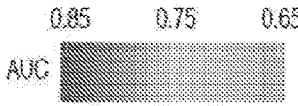

12-month digital features were observed to outperform corresponding Banff scores including CADI in predicting long-term graft loss with superior time-dependent AUCs in the GoCAR cohort (FIG. 6A). The composite class score CDS summarizing abnormalities detected in interstitium, tubules, and inflammation was then used for graft loss risk stratification. The threshold of 12-month CDS (>1.5) was determined according to the percentile of 12-month CADI≥4 in the GoCAR cohort, as 1-year CADI≥4 is considered a surrogate for high risk of graft loss in patients who received transplants (31). A 12-month CDS>1.5 outperformed 12-month CADI≥4, >30% 3-month to 12-month eGFR decline, and acute cellular rejection (including or excluding borderline cases) at 12 months in long term survival prediction, especially for graft survival within 2 years post-transplantation (FIG. 6B). Kaplan-Meier curves of DCGL (P=7.3e-05) (FIG. 6C) confirmed significantly lower survival rate in patients with high 12-month CDS. Significant associations of 12-month CDS risk groups with other published surrogate outcomes including>30% 6-month to 24-month eGFR decline (4,5) (P=0.010) and progressive histologic damage (P=0.005; 24-month CADI>2) were also identified (FIG. 6D). These analyses in the AUSCAD cohort (n=111) also validated the predictive ability of 12-month CDS for long-term survival (FIGS. 13A-B). Thus, high 12-month CDS (>1.5), obtained at 12 months post-transplantation, is an alternative surrogate for long-term graft loss.

Discussion.

A deep-learning-based histopathologic assessment model recognizing and quantifying interstitial, tubular, and inflammatory abnormalities in kidney transplant biopsies was constructed. WSI investigation of baseline and 12-month post-transplant biopsies validated these digital features and further explored potential applications of composite features in clinical practice. The presently disclosed digital features not only exhibited strong correlation with relevant Banff scores, but they also detected subtle changes below the thresholds in Banff scores.

Composite features of baseline ITAS and 12-month CDS were identified to be predictive of early and late graft outcomes, respectively, implying utility in transplant prognosis. Compared to previous investigations in deep-learning-based kidney tissue compartment detection (16-18), the systems and methods of the present disclosure, as described above, advances the field in several ways including: (i) A model incorporating U-Net and a Mask R-CNN architecture provides for more efficient and accurate detection of the normal and abnormal compartments; (ii) As inflammation is another major contributor to graft failure, the Mask R-CNN-based MNL detection model in post-transplant biopsy evaluations, improves graft loss predictive ability; (iii) The slide-wide pathologic lesions were quantified through definition of individual features in interstitium, tubules, and MNL infiltration, respectively, or composite features reflecting overall kidney damage; and (iv) A novel clinical application of developed digital features for graft survival prediction in 2 well-designed cohorts was explored.

Both GoCAR and AUSCAD are large prospective cohorts that collected protocol biopsies pre-implantation and at time points post-transplantation and followed up for medians of 4.5 to 5 years. GoCAR is a multicenter prospective (non-interventional) cohort involving 4 regions in the United States (New York, Michigan, Wisconsin, Illinois) and 1 region in Australia (Sydney). The patients who received kidney transplants are truly heterogeneous, coming from various race or ethnicity backgrounds and using different standard-of-care protocols at different sites. Therefore, the demographic, clinical, and pathologic data in GoCAR were reflective of heterogeneous patients who received transplants and "real-world" clinical management. The models developed from the GoCAR cohort have been validated in the external AUSCAD cohort and are very likely to be applicable to other cohorts.

Although many attempts have been made, no consistent association has been established between baseline histologic findings and post-transplant outcomes among publications (26,32). In comparison with previous studies, the GoCAR cohort obtained superior performance in predicting graft loss with baseline digital features as well as Banff scores. Without being limited to any one theory of operation, such results could be impacted by one or more reasons including: (i) The GoCAR biopsies were collected from multiple centers but were scored centrally by the pathology experts at Massachusetts General Hospital, which minimized the variation from pathology expertise from different centers; (ii) The pre-implanted baseline biopsies were preserved through paraffin embedding rather than freezing procedure. It has been reported that frozen tissue stained with hematoxylin and eosin contain less contrast thus subtle lesions can easily be missed, and the artifacts in frozen sections often cause misdiagnoses (26), leading to poor association with post-transplant outcomes; (iii) Although controversial, a few studies have reported significant associations between interstitial fibrosis- and tubular atrophy-related pathologic features and graft function or survival (33-41). Taken together, the results described herein validate the association of baseline pathologic features with transplant outcomes including graft survival. In particular, a strong prediction power of short-term survival using baseline digital features was demonstrated.

The major limitations of current approaches in pathologic evaluation for baseline biopsies are the variations from slide processing procedure and the expertise in transplant pathologic assessment (32,42). For example, the Banff system itself has limitations by using categories rather than continuous variables (43). Accordingly, the deep-learning-based methods disclosed herein overcome these drawbacks by producing consistent and automated results within 30 minutes from scanned images. As an example, the ITAS at baseline was superior to Banff ci+ct and KDPI and demonstrated a capability for stratifying risk of early graft damage, thus providing early information with utility for post-transplant monitoring, risk stratification, or potential interventional trials. The CDS from 12-month protocol biopsies also predicted long-term graft survival, outperforming histology and clinical factors. Reporting longer-term hard outcomes from prospective trials has been an issue in kidney transplantation research (44). The identification of surrogate end points is a major unmet need that often prevents the design of adequately powered trials. Recent studies proposed using eGFR decline within 24 to 36 months as a long-term graft loss surrogate (4,5). However, such a surrogate has several limitations, including: (i) Creatinine measurement is impacted by a number of factors including timing of collection in the day, diet, and interlaboratory variation (45,46); (ii) eGFR decline has low detection sensitivity because it requires multiple measurements during long-term follow-up, and the ≥40% decline from 6 to 24 months, as suggested by a prior study for graft loss prediction (5), only occurred in 4% of patients in the GoCAR cohort although rates of graft loss were 12% for DCGL. In contrast, 12-month CDS was able to detect 29% of GoCAR and 21% of AUSCAD populations as high risk as early as 12 months while still exhibiting optimal AUCs in long-term graft loss prediction.

These studies focused on investigation of the digital features from protocol biopsies at baseline and 12-month post-transplantation with transplant graft outcomes (particularly graft loss) for prognosis purpose. However, the trained model, which was built from protocol biopsies, is further expected to work on for-cause biopsies as well, because the severity of histologic lesions (such as Banff ct and/or ti scores) relies largely on the amount or density of individual abnormal objects and similarly the slide-wide digital features are summarized from detection of corresponding abnormal objects. Thus, with an accurate detection of individual abnormal objects, slide-wide digital features would be expected to accurately reflect the pathologic lesions regarding interstitium, tubules, and MNL infiltration and correlate with Banff scores in both protocol and for-cause biopsies.

In summary, the deep-learning approach disclosed herein provided a reliable risk stratification of post-transplant graft survival using transplant biopsies at baseline and 12 months post-transplantation. This represents a novel and reproducible approach to facilitate early prevention, risk stratification, or post-transplant monitoring in clinical practice.

REFERENCES

1. Hunsicker L G. A survival advantage for renal transplantation. N Engl J Med. 1999; 341:1762-1763.
2. Parajuli S, Aziz F, Garg N, el al. Histopathological characteristics and causes of kidney graft failure in the current era of immunosuppression. World J Transplant. 2019; 9:123-133.
3. Furness P N, Taub N. Convergence of European Renal Transplant Pathology Assessment Procedures (CERTAP) Project. International variation in the interpretation of renal transplant biopsies: report of the CERTPAP project. Kidney Int. 2001; 60:1998-2012.
4. Clayton P A, Lim W H, Wong G, Chadban S J. Relationship between eGFR decline and hard outcomes after kidney transplants. J Am Soc Nephrol. 2016; 27:3440-3446.
5. Faddoul G, Nadkarni G N, Bridges N D, et al. CTOT-17 Consortium. Analysis of biomarkers within the initial 2 years posttransplant and 5-year kidney transplant outcomes: results from clinical trials in Organ Transplantation-17. Transplantation. 2018; 102:673-680.
6. Lundervold A S, Lundervold A. An overview of deep learning in medical imaging focusing on MRI. Z Med Phys. 2019; 29:102-127.
7. Xue Y, Chen S, Qin J, el al. Application of deep learning in automated analysis of molecular images in cancer: a survey. Contrast Media Mol Imaging. 2017; 2017: 9512370.
8. Janowczyk A, Madabhushi A. Deep learning for digital pathology image analysis: a comprehensive tutorial with selected use cases. J Pathol Inform. 2016; 7:29.
9. Wang S, Yang D M, Rong R, el al. Pathology image analysis using segmentation deep learning algorithms. Am J Pathol. 2019; 189:1686-1698.
10. Bukowy J D, Dayton A, Cloutier D, el al. Region-based convolutional neural nets for localization of glomeruli in trichrome-stained whole kidney sections. J Am Soc Nephrol. 2018; 29:2081-2088.
11. Gallego J, Pedraza A, Lopez S, el al. Glomerulus classification and detection based on convolutional neural networks. J Imaging. 2018; 4:20.
12. Ginley B, Lutnick B, Jen K-Y, el al. Computational segmentation and classification of diabetic glomerulosclerosis. J Am Soc Nephrol. 2019; 30:1953-1967.
13. Kannan S, Morgan L A, Liang B, et al. Segmentation of glomeruli within trichrome images using deep learning. Kidney Int Rep. 2019; 4:955-962.
14. Marsh J N, Matlock M K, Kudose S, et al. Deep learning global glomerulosclerosis in transplant kidney frozen sections. IEEE Trans Med Imaging. 2018; 37:2718-2728.
15. Ginley B, el al. Automated computational detection of interstitial fibrosis, tubular atrophy, and glomerulosclerosis. J AmSoc Nephrol. 2021; 32:837-850.
16. Bouteldja N, Klinkhammer B M, BUlow R D, et at. Deep learning based segmentation and quantification in experimental kidney histopathology. J Ain Soc Nephrol. 2021; 32:52-68.
17. Hermsen M, de Bel T, den Boer M, et at. Deep learning-based histopathologic assessment of kidney tissue. J Ain Soc Nephrol. 2019; 30:1968-1979.
18. Jayapandian C P, Chen Y, Janowczyk A R, el al.; Nephrotic Syndrome Study Network (NEPTUNE). Development and evaluation of deep learning-based segmentation of histologic structures in the kidney cortex with multiple histologic stains. Kidney Int. 2021; 99:86-101.
19. Ronneberger O, Fischer P, Brox T. U-Net: convolutional networks for biomedical image segmentation. 2015. arXiv: 1505.04597.
20. Abdulla W. Mask R-CNN for object detection and instance segmentation on Keras and TensorFlow. GitHub repository 2017.github.com/matterport/Mask_RCNN. Accessed Mar. 31, 2019.
21. Altini N, Cascarano G, Brunetti A, et al. A deep learning instance segmentation approach for global glomerulosclerosis assessment in donor kidney biopsies. Electronics. 2020; 9:1768.
22. O'Connell P J, Zhang W, Menon M C, et at. Biopsy transcriptome expression profiling to identify kidney transplants at risk of chronic injury: a multicentre, prospective study. Lancet. 2016; 388:983-993.

23. Solez K, Colvin R B, Racusen L C, et al. Banff 07 classification of renal allograft pathology: updates and future directions. Ain J Transplant. 2008; 8:753-760.

24. Van Rijsbergen C J. Information Retrieval. 2nd ed. Butterworth-Heinemann; 1979.

25. Blanche P, Dartigues J F, Jacqmin-Gadda H. Estimating and comparing time-dependent areas under receiver operating characteristic curves for censored event times with competing risks. Stat Med. 2013; 32:5381-5397.

26. Naesens M. Zero-time renal transplant biopsies: a comprehensive review. Transplantation. 2016; 100:1425-1439.

27. OPTN. A guide to calculating and interpreting the Kidney Donor Profile Index (KDPI). 2020. optn.transplant.hrsa.gov/media/1512/guide_to_calculating_interpreting_kdpi.pdf Accessed Jun. 5, 2020.

28. OPTN. KDRI to KDPI mapping table. 2018. optn.transplant.hrsa.gov/media/2974/kdpi_mapping_table_2018.pdf. Accessed Jun. 5, 2020.

29. Rao P S, Schaubel D E, Guidinger M K, et al. A comprehensive risk quantification score for deceased donor kidneys: the kidney donor risk index. Transplantation. 2009; 88:231-236.

30. Helanterä I, Ortiz F, Koskinen P. Chronic Allograft Damage Index (CADI) as a biomarker in kidney transplantation. In: Patel V B, Preedy V R, eds. Biomarkers in Kidney Disease. Springer Netherlands; 2016:669-687.

31. Hayry P, Paavonen T, Taskinen E, el al. Protocol core needle biopsy and histological chronic allograft damage index as surrogate endpoint for long-term graft survival. Transplant Proc. 2004; 36:89-91.

32. Wang C J, Wetmore J B, Crary G S, Kasiske B L. The donor kidney biopsy and its implications in predicting graft outcomes: a systematic review. Am J Transplant. 2015; 15:1903-1914.

33. Howie A J, Ferreira M A S, Lipkin G W, Adu D. Measurement of chronic damage in the donor kidney and graft survival. Transplantation. 2004; 77:1058-1065.

34. De Vusser K, Lerut E, Kuypers D, el al. The predictive value of kidney allograft baseline biopsies for long-term graft survival. J Ain Soc Nephrol. 2013; 24:1913-1923.

35. Lopes J A, Moreso F, Riera L, et al. Evaluation of pre-implantation kidney biopsies: comparison of Banff criteria to a morphometric approach. Kidney Int. 2005; 67:1595-1600.

36. Navarro M D, Lopez-Andreu, Rodriguez-Benot A, el al. Significance of preimplantation analysis of kidney biopsies from expanded criteria donors in long-term outcome. Transplantation. 2011; 91:432-439.

37. Hofer J, Regele H, Bohmin G A, el al. Pre-implant biopsy predicts outcome of single-kidney transplantation independent of clinical donor variables. Transplantation. 2014; 97:426-432.

38. Losappio V, Stallone G, Infante B, el al. A single-center cohort study to define the role of pretransplant biopsy score in the long-term outcome of kidney transplantation. Transplantation. 2014; 97:934-939.

39. Kahu J, Kyllonen L, Raisanen-Sokolowski A, Salmela K. Donor risk score and baseline biopsy CADI value predict kidney graft outcome. Clin Transplant. 2011; 25:E276-E283.

40. Heilman R L, Smith M L, Smith B H, el at. Progression of interstitial fibrosis during the first year after deceased donor kidney transplantation among patients with and without delayed graft function. Clin J Am Soc Nephrol. 2016; 11:2225-2232.

41. Arias L F, Blanco J, Sanchez-Fructuoso A, et al. Histologic assessment of donor kidneys and graft outcome: multivariate analyses. Transplant Proc. 2007; 39:1368-1370.

42. Singh P, Farber J L, Doria C, et at. Peritransplant kidney biopsies: comparison of pathologic interpretations and practice patterns of organ procurement organizations. Clin Transplant. 2012; 26:E191-E199.

43. Vasquez-Rios G, Menon M C. Kidney transplant rejection clusters and graft outcomes: revisiting Banff in the era of "big data.". J Ain Soc Nephrol. 2021; 32:1009-1011.

44. Fergusson N A, Ramsay T, Chasse M, et al. Impact of using alternative graft function endpoints: a secondary analysis of a kidney transplant trial. Transplant Direct. 2019; 5:e439.

45. Joffe M, Hsu C, Feldman H I, et at. Variability of creatinine measurements in clinical laboratories: results from the CRIC study. Am J Nephrol. 2010; 31:426-434.

46. Delanaye P, Cavalier E, Pottel H. Serum creatinine: not so simple Nephron. 2017; 136:302-308.

47. Haller M C, Wallisch C, Mjoen G, el at. Predicting donor, recipient and graft survival in living donor kidney transplantation to inform pretransplant counselling: the donor and recipient linked iPREDICTLIVING tool—a retrospective study. Transpl Int. 2020; 33:729-739.

48. Irish W D, Ilsley J N, Schnitzler M A, et at. A risk prediction model for delayed graft function in the current era of deceased donor renal transplantation. Am J Transplant. 2010; 10:2279-2286.

49. Kasiske B L, Israni A K, Snyder J J, et at. A simple tool to predict outcomes after kidney transplant. Ain J Kidney Dis. 2010; 56:947-960.

SUPPLEMENTARY REFERENCES

S1. O'Connell, P. J., el al., Biopsy transcriptome expression profiling to identify kidney transplants at risk of chronic injury: a multicentre, prospective study. Lancet, 2016. 388(10048): p. 983-93.

S2. Shorten, C. and T. M. Khoshgoftaar, A survey on image data augmentation for deep learning. Journal of Big Data, 2019. 6(1): p. 1-48.

S3. He, K., et al. Mask R-CNN. 2017. arXiv:1703.06870.

S4. Ronneberger, O., P. Fischer, and T. Brox U-Net: Convolutional Networks for Biomedical Image Segmentation. 2015. arXiv: 1505.04597.

S5. Abdulla, W. Mask R-CNN for object detection and instance segmentation on Keras and TensorFlow. GitHub repository 2017; Available from: gitliub.com/matterport/Mask_RCNN. S6. Akeret, J., et al., Radio frequency interference mitigation using deep convolutional neural networks. Astronomy and Computing, 2017. 18: p. 35.

S7. Lin, T.-Y., et al. Microsoft coco: Common objects in context. in European conference on computer vision. 2014. Springer.

S8. Van Rijsbergen, C. J., Information Retrieval (2nd ed.). 1979: Butterworth-Heinemann.

CONCLUSION

The terminology used herein is for the purpose of describing particular cases and is not intended to be limiting. As used herein, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the tenets "including," "includes," "having," "has," "with," or variants thereof are used in either the detailed description and/or the claims, such terms are intended to be inclusive in a manner similar to the term "comprising."

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are used to distinguish one element from another. For example, a first subject could be termed a second subject, and, similarly, a second subject could be termed a first subject, without departing from the scope of the present disclosure. The first subject and the second subject are both subjects, but they are not the same subject.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event)" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many alterations, modifications, and variations will be apparent to those skilled in the art in light of the foregoing description without departing from the spirit or scope of the present disclosure and that when numerical lower limits and numerical upper limits are listed herein, ranges from any lower limit to any upper limit are contemplated. The implementations were chosen and described in order to best explain the principles and their practical applications, to thereby enable others skilled in the art to best utilize the implementations and various implementations with various modifications as are suited to the particular use contemplated.

What is claimed:

1. A method for identifying a risk of kidney graft failure for a subject, the method comprising:

at a computer system comprising at least one processor and a memory storing at least one program for execution by the at least one processor, the at least one program comprising instructions for:

obtaining, in electronic format, a first image of a kidney graft biopsy on a substrate, wherein the first image represents at least a first subset of morphological classes in a plurality of morphological classes comprising at least a first tissue compartment class and an inflammatory mediator class, the first image comprises at least 10,000 pixels, and the graft biopsy originates from the subject;

inputting the first image into a trained model, wherein the trained model comprises at least 10,000 parameters;

identifying, as output from the trained model, for each respective morphological class in the at least the first subset of morphological classes, a corresponding one or more objects in the first image that fall within the respective morphological class, wherein the first subset of morphological classes includes the first tissue compartment class or the inflammatory mediator class;

generating, for each respective morphological class in the at least the first subset of morphological classes, a corresponding plurality of digital features comprising:

(i) a first corresponding subset of individual feature scores, wherein each respective individual feature score is obtained using the corresponding one or more objects for the respective morphological class, and (ii) a second corresponding subset of composite feature scores, wherein each respective composite feature score is obtained by combining two or more individual feature scores in the first corresponding subset of individual feature scores; and comparing, for each respective morphological class in the at least the first subset of morphological classes, a respective digital feature in the corresponding plurality of digital features for the respective morphological class to a reference criterion, thereby determining the risk of kidney graft failure for the subject.

2. The method of claim 1, wherein the first image is a whole-slide histological image.

3. The method of claim 1, wherein the first image comprises at least 100,000 pixels.

4. The method of claim 1, wherein the kidney graft biopsy is obtained pre-implantation or post-transplantation.

5. The method of claim 1, wherein the kidney graft biopsy is preserved by paraffin embedding.

6. The method of claim 1, wherein the first tissue compartment class is selected from the group consisting of tubules, glomeruli, and interstitium, and the inflammatory mediator class is mononuclear leukocytes (MNLs).

7. The method of claim 1, wherein the trained model comprises a plurality of component models, comprising:

a compartment detection model trained to identify one or more first corresponding objects in the first image that fall within a first morphological class in the plurality of morphological classes, an inflammation detection model trained to identify one or more second corresponding objects in the first image that fall within a second morphological class in the plurality of morphological classes, and a tissue segmentation model trained to identity one or more third corresponding objects in the first image that fall within a third morphological class in the plurality of morphological classes.

8. The method of claim 1, wherein the trained model comprises a convolutional neural network comprising one or more filters, a respective kernel size, and a respective stride.

9. The method of claim 1, wherein the generating the corresponding plurality of digital features for a respective morphological class further comprises:

(i) identifying, in the first image, a first region of interest as having a first condition for the respective morphological class, and (ii) assigning the first condition to one or more individual feature scores, in the first corresponding subset of individual feature scores, wherein the first condition is selected from the group consisting of abnormal and normal.

10. The method of claim 1, wherein a respective individual feature score in the first corresponding subset of individual feature scores is selected from the group consisting of:

a size of an area of the substrate, a number of objects in a corresponding plurality of objects for a respective morphological class within an area of the substrate, and a percentage of a corresponding plurality of objects for a respective morphological class over an area of the substrate.

11. The method of claim 1, wherein a respective individual feature score in the first corresponding subset of individual feature scores is selected from the group consisting of:

an abnormal interstitial area percentage, a standardized abnormal tubule density, a mononuclear leukocyte-enriched area percentage, and a standardized mononuclear leukocyte density.

12. The method of claim 11, wherein a respective composite feature score in the second corresponding subset of composite feature scores is selected from the group consisting of:

an interstitial and tubule abnormality score (ITAS) obtained by combining the abnormal interstitial area percentage and the standardized abnormal tubule density, and a mononuclear leukocyte infiltration score (MNL-IS) obtained by combining the mononuclear leukocyte-enriched area percentage and the standardized mononuclear leukocyte density.

13. The method of claim 1, further comprising:

generating a composite class score by combining at least a first composite feature score for a corresponding first morphological class and a second composite feature score for a corresponding second morphological class different from the first morphological class, wherein the comparing, for each respective morphological class in the at least the first subset of morphological classes, a respective digital feature in the corresponding plurality of digital features for the respective morphological class to a reference criterion further comprises comparing the composite class score to the reference criterion.

14. The method of claim 1, wherein the kidney graft failure is death-censored graft loss, acute cellular rejection, or decline of estimated glomerular filtration rate (eGFR).

15. The method of claim 1, further comprising using the respective digital feature to categorize the first image into a risk category, based on the comparison with the reference criterion, wherein the risk category is one of three nonoverlapping stratified risk categories selected from the group consisting of low risk, medium risk, or high risk.

16. The method of claim 1, wherein the first image is of a pre-implantation kidney graft biopsy, and the risk of kidney graft failure is predictive for a period of no more than 1 year post-transplantation.

17. The method of claim 1, wherein the first image is of a post-transplantation kidney graft biopsy, and the risk of kidney graft failure is predictive for a period of 1 year or more post-transplantation.

18. The method of claim 1, wherein the trained model is obtained by a procedure comprising:

(a) obtaining, in electronic format, a training dataset comprising:

for each respective training sample in a plurality of training samples:

(i) a corresponding training image of a training kidney graft biopsy on a substrate, wherein the corresponding training image represents at least a second subset of morphological classes in a plurality of morphological classes comprising at least the first tissue compartment class and the inflammatory mediator class, and wherein the corresponding training image comprises at least 10,000 pixels, and (ii) a corresponding measured indication that localizes one or more objects in the corresponding training image that fall within each respective morphological class in the at least the second subset of morphological classes, wherein:

for each respective training sample in a first subset of the plurality of training samples, the corresponding training image is of a kidney graft biopsy obtained pre-implantation, for each respective training sample in a second subset of the plurality of training samples, the corresponding training image is of a kidney graft biopsy obtained post-transplantation, and the plurality of training samples collectively represents each respective morphological class in the plurality of morphological classes;

(b) training an untrained or partially trained model comprising at least 10,000 parameters by a procedure comprising, for each corresponding training image of each corresponding training sample in the plurality of training samples:

(i) inputting the respective image as input to the untrained or partially trained model thereby obtaining a corresponding calculated indication that localizes one or more objects in the corresponding image that fall within each respective morphological class in the at least the second subset of morphological classes, and (ii) using at least a difference between the corresponding calculated indication and the corresponding measured indication to update all or a subset of the at least 10,000 parameters, thereby forming the trained model, wherein the trained model is configured to identify, for each respective morphological class in the plurality of morphological classes, a corresponding one or more objects that fall within the respective morphological class.

19. The method of claim 18, wherein the training (b) is characterized by one or more hyperparameters in the at least 10,000 parameters that is a predetermined number of training epochs, a predetermined batch size, wherein the batch size specifies a number of corresponding training images of a predetermined number of training samples in the plurality of training samples, or a predetermined learning rate.

20. The method of claim 18, wherein the plurality of training samples comprises at least 1,000 training samples.

21. A computer system having one or more processors, and memory storing one or more programs for execution by the one or more processors, the one or more programs comprising instructions for performing a method of identifying a risk of kidney graft failure for a subject, the method comprising:

obtaining, in electronic format, a first image of a kidney graft biopsy on a substrate, wherein the first image represents at least a first subset of morphological classes in a plurality of morphological classes comprising at least a first tissue compartment class and an inflammatory mediator class, the first image comprises at least 10,000 pixels, and the graft biopsy originates from the subject;

inputting the first image into a trained model, wherein the trained model comprises at least 10,000 parameters;

identifying, as output from the trained model, for each respective morphological class in the at least the first subset of morphological classes, a corresponding one or more objects in the first image that fall within the respective morphological class, wherein the first subset of morphological classes includes the first tissue compartment class or the inflammatory mediator class;

generating, for each respective morphological class in the at least the first subset of morphological classes, a corresponding plurality of digital features comprising:
(i) a first corresponding subset of individual feature scores, wherein each respective individual feature score is obtained using the corresponding one or more objects for the respective morphological class, and
(ii) a second corresponding subset of composite feature scores, wherein each respective composite feature score is obtained by combining two or more individual feature scores in the first corresponding subset of individual feature scores; and comparing, for each respective morphological class in the at least the first subset of morphological classes, a respective digital feature in the corresponding plurality of digital features for the respective morphological class to a reference criterion, thereby determining the risk of kidney graft failure for the subject.

22. A non-transitory computer readable storage medium storing one or more programs configured for execution by a computer, the one or more programs comprising instructions for carrying out a method for identifying a risk of kidney graft failure for a subject, the method comprising:

obtaining, in electronic format, a first image of a kidney graft biopsy on a substrate, wherein the first image represents at least a first subset of morphological classes in a plurality of morphological classes comprising at least a first tissue compartment class and an inflammatory mediator class, the first image comprises at least 10,000 pixels, and the graft biopsy originates from the subject;

inputting the first image into a trained model, wherein the trained model comprises at least 10,000 parameters;

identifying, as output from the trained model, for each respective morphological class in the at least the first subset of morphological classes, a corresponding one or more objects in the first image that fall within the respective morphological class, wherein the first subset of morphological classes includes the first tissue compartment class or the inflammatory mediator class;

generating, for each respective morphological class in the at least the first subset of morphological classes, a corresponding plurality of digital features comprising:
(i) a first corresponding subset of individual feature scores, wherein each respective individual feature score is obtained using the corresponding one or more objects for the respective morphological class, and
(ii) a second corresponding subset of composite feature scores, wherein each respective composite feature score is obtained by combining two or more individual feature scores in the first corresponding subset of individual feature scores; and comparing, for each respective morphological class in the at least the first subset of morphological classes, a respective digital feature in the corresponding plurality of digital features for the respective morphological class to a reference criterion, thereby determining the risk of kidney graft failure for the subject.

* * * * *